United States Patent
Escaich et al.

(10) Patent No.: US 8,513,250 B2
(45) Date of Patent: Aug. 20, 2013

(54) IMIDAZOLO-HETEROARYL DERIVATIVES WITH ANTIBACTERIAL PROPERTIES

(75) Inventors: Sonia Escaich, Paris (FR); Alexis Denis, Paris (FR); Vincent Gerusz, Paris (FR); François Moreau, Orsay (FR); Mayalen Oxoby, Paris (FR); Yannick Bonvin, St-Germain en Laye (FR)

(73) Assignee: Laboratoire Biodim, Paris (FR)

( * ) Notice: Subject to any disclaimer, the term of this patent is extended or adjusted under 35 U.S.C. 154(b) by 539 days.

(21) Appl. No.: 12/450,348

(22) PCT Filed: Mar. 21, 2008

(86) PCT No.: PCT/IB2008/051080
§ 371 (c)(1),
(2), (4) Date: Feb. 3, 2010

(87) PCT Pub. No.: WO2008/117225
PCT Pub. Date: Oct. 2, 2008

(65) Prior Publication Data
US 2010/0130489 A1    May 27, 2010

Related U.S. Application Data

(60) Provisional application No. 60/919,840, filed on Mar. 23, 2007.

(30) Foreign Application Priority Data

Mar. 23, 2007  (EP) ................................ 07290356

(51) Int. Cl.
C07D 487/04   (2006.01)
C07D 471/04   (2006.01)
A61K 31/437   (2006.01)
A61K 31/4985  (2006.01)

(52) U.S. Cl.
USPC ............. 514/250; 544/346; 544/333; 546/82; 514/293

(58) Field of Classification Search
None
See application file for complete search history.

(56) References Cited

U.S. PATENT DOCUMENTS
6,124,287 A    9/2000  Ceccarelli

FOREIGN PATENT DOCUMENTS
WO    WO 97/19079    5/1997

OTHER PUBLICATIONS

International Search Report for PCT/IB2008/051080, mailed Sep. 16, 2008.
CAS-RN 887411-96-3, & "Peakdale Screening Library", (Sep. 13, 2006), Peakdale Molecular Ltd., 5 pages.
J. May et al., "Inhibition of the D-alanine:D-alanyl carrier protein ligase from *Bacillus subtilis* increases the bacterium's susceptibility to antibiotics that target the cell wall", FEBS Journal, No. 272, No. 12, (Jun. 2005), pp. 2993-3003.
Corona, Paola et al, "4-Substituted anilino imidazo[1,2-a] and triazolo[4,3-1]quinoxalines. Synthesis and evaluation in vitro biological activity", European Journal of Medicinal Chemistry, vol. 41, No. 9, (Sep. 2006), pp. 1102-1107.
Morjaria, S. et al., "Impairment of TNF-α Production and action by imidazo[1,2- α] quinoxalines, a derivative family which displays potential anti-inflammatory properties", International Journal of Immunopathology and Pharmacology, vol. 19, No. 3, (2006), pp. 525-538.
Dockrell, D.H. et al., "Imiquimod and resiquimod as novel immunomodulators", Journal of Antimicrobial Chemotherapy, vol. 48, No. 6, (Dec. 2001), pp. 751-755.

*Primary Examiner* — Michael Barker
(74) *Attorney, Agent, or Firm* — Nixon & Vanderhye P.C.

(57) ABSTRACT

The invention relates to Imidazolo-heteroaryl derivatives of formula (I). The compounds inhibit the activity of the Dlta enzyme of Gram-positive bacteria and are useful to treat Gram-positive bacterial infections. Furthermore the application discloses method for assessing the Dlta inhibitory activity of tested molecules and a method for measuring the efficacy of molecules in inhibiting bacteria proliferation in vitro.

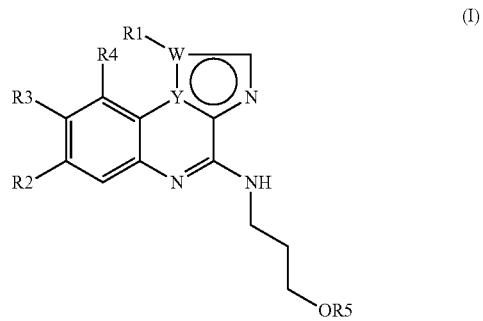

31 Claims, 3 Drawing Sheets

Effect of compound of example 8

Effect of compound example 14

Effect of compound example 16

Effect of compound example 19

IMIDAZOLO-HETEROARYL DERIVATIVES WITH ANTIBACTERIAL PROPERTIES

This application is the U.S. national phase of International Application No. PCT/IB2008/051080, filed 21 Mar. 2008, which designated the U.S. and claims priority to Europe Application No. 07290356.0, filed 23 Mar. 2007; and claims the benefit of U.S. Provisional Application No. 60/919,840, filed 23 Mar. 2007, the entire contents of each of which are hereby incorporated by reference.

The invention relates to imidazolo-heteroaryl derivatives which inhibit the activity of the DltA enzyme of Gram-positive bacteria, and are useful to treat Gram-positive bacterial infections in human and animals.

It more particularly relates to novel imidazolo-quinoxalines and imidazolo-quinolines derivatives having DltA inhibiting properties and a process for their synthesis.

It is known that the extracellular bacteria responsible for serious infections are capable of growth in the blood and are resistant to the bactericidal action of the host innate immunity. This resistance of bacteria to the innate immunity components allows dissemination of the infection, via the blood, to the various tissues of the host's body.

The components of the innate immunity are either circulating molecules such as the complement factors, and the antibacterial peptides such as defensins, which could have bactericidal effects by direct interactions with the bacterium cell wall, or either circulating cells such as the polymorphonuclear leukocytes (PMNs) able to kill invading bacteria after activation induced during the inflammation process.

Among the many virulence factors described to be important for bacteria to resist the innate immunity components are the mechanism involved in resistance to cationic antimicrobial peptides (CAMP). Cationic antimicrobial peptides (CAMP) play a fundamental role in innate immune defences, both through direct antimicrobial activity and through immunomodulatory effects (Boman et al., 2003). The CAMP dominating targets are bacterial membranes and CAMP interacts with negatively charged bacterial surface. One of the main mechanism present in bacteria to decrease the negative charge of the cell wall is the addition of positively charge amino acid on structural element of the cell surface. For example, it was shown in S. agalactiae that the activities of the cationic peptides against the bacteria increase as the bacterial electropositive charge surface decreases (Poyart et al., 2001).

Mutant lacking DltA gene resulted in absence of D-ala ester in the LTA (Poyart et al., 2001) one of the major component of Gram-positive cell wall. As consequence, D-ala deficient LTA bacteria displayed a modification in the net charge of their cell surface and as a result could exhibit a wide range of phenotypic changes.

Defect in D-alanyl LTA synthesis was in particular associated to in vitro increased susceptibility to various bactericidal compounds including cationic antimicrobial peptide. An increased sensitivity to antibiotics that target the cell wall has been observed in bacterial strains with an altered D-ala content due to inactivation of the DltA function.

Survival of bacteria to cell killing as well as cell invasion ability has also been correlated to the D-alanylation of LTA and the involvement of D-alanylation of lipoteichoic acid (LTA) in the pathogenesis of many bacteria has been well documented.

These studies together with the results given in the present application and WO 04 005535 showing a correlation between the sensitivity to cationic peptides and the virulence attenuation of the deletion mutants in the genes of the dlt operon has lead to consider dlt genes and in particular dltA as good target to find inhibitors.

This gene has been described previously and it was demonstrated in several studies to be necessary for virulence of Gram-positive bacteria.

The dltA gene is the first gene of the dlt operon found in S. agalactiae and in other Gram-positive organism. DltA is implicated in the first step of a biological process leading to the modification of LTA by addition of D-ala to the LTA. DltA catalyzes the ligation of the D-ala to an acyl carrier protein (DltC).

Since DltA function is necessary for cationic peptide resistance and considering the role of these peptides in innate immunity, the inventors established methods to develop and synthesize new compounds having the property to inhibit this target and to affect CAMP sensitivity of the bacteria possessing this gene function, and to increase the susceptibility of such bacteria to the killing by the innate immunity of the host.

Because the dlt operon is conserved in many Gram positive bacteria of medical importance, such inhibitors would be useful in rendering invading bacteria sensitive to killing by the innate immunity mechanism of the host, allowing eradication or prevention of the infection by a new mechanism of action when compared to current antibiotic treatment.

These virulence factors inhibitors by making the bacteria more sensitive to the host innate immunity appear to be useful at providing a new mechanism of action for compounds with antibacterial effect in the host, and can be used for treatment of infections due to Gram-positive bacteria, in particular the bacteria resistant to currently used antibiotics.

The new compounds inhibiting d-alanination of LTA have also the property to render the bacteria more sensitive to the activity of classical antibiotics.

Therefore such compounds are useful to synergize the activity of classical antibiotics used to treat gram positive infections.

It is then an object of the invention to provide new molecules capable of inhibiting the gene product of DltA which is necessary for the pathogenicity of Gram-positive bacteria in particular Gram-positive strains responsible for severe infections.

Another object of the invention is to provide drugs containing in their active principle at least one of said inhibitory molecules or one of said inhibitory molecules in combination with an antimicrobial peptide or a natural, hemisynthetic or synthetic antibacterial molecule.

Still another object of the invention is to provide a biochemical HTS assay to measure the efficacy of compounds to be tested in inhibiting the d-alanylation of the LTA in the bacteria in vitro.

The invention relates to molecules having general formula (I)

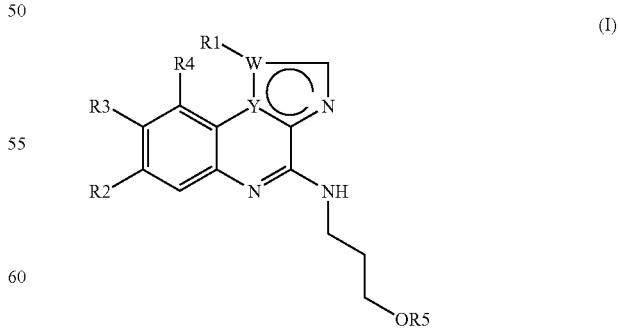

wherein,
Y=N and W is C
or
Y=C and W=N,

R1 is $C_1$-$C_{10}$alkyl, $C_2$-$C_{10}$alkenyl, $C_2$-$C_{10}$alkynyl, $CO_2R_8$, $COR_a$, $CONR_aR_b$, $CR_a$=$NOR_b$, $S(O)_nR_a$, phenyl or heterocycle, all being optionally substituted by one or several identical or different R, or R1 is H, halogen or CN;

R2 is $C_1$-$C_{10}$alkyl, $C_2$-$C_{10}$alkenyl, $C_2$-$C_{10}$alkynyl, $OR_a$, $S(O)_nR_a$, phenyl or heterocycle, all being optionally substituted by one or several identical or different R, or R2 is H or halogen;

R3 is $C_1$-$C_{10}$alkyl, $C_2$-$C_{10}$alkenyl, $C_2$-$C_{10}$alkynyl, $CO_2R_a$, $COR_a$, $OR_a$, $NR_aR_b$, $NR_aCOR_b$, $CONR_aR_b$, $CR_a$=$NOR_b$, $S(O)_nR_a$, $SO_2NR_aR_b$, phenyl or heterocycle, all being optionally substituted by one or several identical or different R, or R3 is H, halogen or CN;

R4 is $C_1$-$C_{10}$alkyl, $C_2$-$C_{10}$alkenyl, $C_2$-$C_{10}$alkynyl, phenyl or heterocycle all being optionally substituted by one or several identical or different R, or R4 is H, halogen or CN;

R5 is H, $COR_a$, $CO_2Ra$, $P(O)(OH)_2$ or $COCHR_aNR_bR_c$;

$R_a$, $R_b$ and $R_c$ identical or different are selected from the group consisting of H, $C_1$-$C_{10}$alkyl, $C_2$-$C_{10}$alkenyl, $C_2$-$C_{10}$alkynyl, phenyl and heterocycle;

R is selected from the group consisting of $C_1$-$C_{10}$alkyl, $C_2$-$C_{10}$alkenyl, $C_2$-$C_{10}$alkynyl, phenyl, heterocycle, $CO_2R_a$, $COR_a$, $CONR_aR_b$, $OCOR_a$, $OR_a$, $NR_aR_b$, $CR_a$=$NOR_b$, $NR_aCOR_b$, $NR_aCOOR_b$, $OCONR_aR_b$, $NR_aCONR_bR_c$, $NR_aSO_2R_b$, $S(O)_nR_a$, and $SO_2NR_aR_b$, all being optionally substituted by one or several identical or different R', or R is halogen, CN or $NO_2$, Ra, Rb and Rc are such as described above;

R' is selected from the group consisting of $C_1$-$C_{10}$alkyl, $CO_2R''$, $COR''$, $CONR''R'''$, $OCOR''$, $OR''$, $NR''R'''$, $CR''$=$NOR'''$, $NR''COR'''$, $NR''COOR'''$, $OCONR''R'''$, $NR''CONR''R'''$, $NR''SO_2R'''$, $S(O)_nR''$, $SO_2NR''R'''$, halogen, CN and $NO_2$;

R'' and R''' being identical or different are H or $C_1$-$C_{10}$alkyl or form together a 3 to 6 membered nitrogenous heterocycle;

n is 0, 1 or 2;

with the proviso that R5 is not H, when R2=F or $SO_2CH_3$; R1, R3 et R4=H; and W=C, and pharmaceutically acceptable salts thereof, In the general formula (I):

"$C_1$-$C_{10}$ alkyl" as applied herein means linear, branched or cyclic hydrocarbon groups having 1 to 10 carbon atoms preferably methyl, ethyl, n-propyl, isopropyl, n-butyl, isobutyl and t-butyl, pentyl, n-pentyl, isopentyl, neopentyl, hexyl, octyl, cyclopropyl, cyclobutyl, cyclopentyl, cyclohexyl;

"$C_2$-$C_{10}$alkenyl" and "$C_2$-$C_{10}$alkynyl" as applied herein means linear, branched or cyclic hydrocarbon groups of 2 to 10 carbon atoms, having at least one double bond or one triple bond and preferably, ethenyl, propenyl, butenyl, cyclohexenyl, ethynyl, propargyl, butynyl; "Halogen" means F, Cl, Br, and I;

"Heterocycle" as applied herein means a 5-10 membered aromatic or non-aromatic mono or bicyclic ring, containing at least one heteroatom selected from N, O and S. Illustrative heterocycles are for example selected in the group comprising benzofuryl, benzimidazolyl, benzopyranyl, benzothienyl, furyl, imidazolyl, indolinyl, morpholinyl, piperidinyl, piperazinyl, pyrrolyl, pyrrolidinyl, pyrazolyl, tetrahydropyridinyl, pyridinyl, thiazolyl, thienyl, quinolinyl, isoquinolinyl, and tetra- and perhydro-quinolinyl and isoquinolinyl, pyrazinyl, pyrazidinyl, triazinyl, triazolyl, tetrazolyl, indolyl, indazolyl, pyrimidinyl, pyridonyl, oxazolyl, isoxazolyl, isothienyl, quinazolinyl, oxadiazolyl, thiadiazolyl;

Also included in the invention are any N-oxide form of the derivatives, as well as the racemic derivatives, all possible forms of pure enantiomers and each unique non racemic (scalemic) mixture of enantiomers, in case the derivatives of formula (I) have one or more chiral centers, both the cis (Z) and trans (E) isomers in case the derivatives of formula (I) have unsaturated carbon carbon double bonds;

Preferred number of substitutions by R or R' for any substituted $C_1$-$C_{10}$ alkyl, $C_2$-$C_{10}$alkenyl, $C_2$-$C_{10}$alkynyl, phenyl, heterocycle or $R_a$, $R_b$, $R_c$, is from 1 to 5.

Advantageously, as illustrated by the Examples, the above defined molecules have measurable $IC_{50}$ values and are therefore of great value for treating Gram positive infections in human and animals.

The invention thus particularly relates to molecules of formula (I), wherein Y=N and W is C and R1 is selected in the group comprising H, halogen, $C_1$-$C_{10}$alkyl, $C_2$-$C_{10}$alkenyl, $C_2$-$C_{10}$alkynyl, $CO_2R_a$, $COR_a$, $CONR_aR_b$, $S(O)_nR_a$ phenyl, R substituted phenyl, 5 or 6-membered membered heterocycle, R substituted heterocycle, with R and Ra being such as above defined, or Y=C and W is N and R1 is selected in the group of $C_1$-$C_{10}$alkyl, R substituted alkyl, phenyl and R substituted phenyl, with R being such as above defined.

In the following, several groups will be distinguished for R1, when Y=N and W is C, their numbering being not linked to their therapeutical interest.

Thus, in group 1, R1 is H;

in group 2, R1 is $C_1$-$C_{10}$ alkyl;

in group 3, R1 is $C_2$-$C_{10}$ alkenyl;

in group 4, R1 is $C_2$-$C_{10}$ alkynyl;

in group 5, R1 is an halogen selected between Br and I;

in group 6, R1 is phenyl;

in group 7, R1 represents a phenyl group substituted by R which is selected in the group comprising $C_1$-$C_{10}$alkyl-CO—NH—, $NH_2$—$SO_2$—, $C_1$-$C_{10}$—O—, $C_1$-$C_{10}$ alkyl-$SO_2$—NH, non aromatic heterocycle, $C_1$-$C_{10}$alkyl-NH—CO—, HO—$C_1$-$C_{10}$-alkyl-, $NH_2$—$C_1$-$C_{10}$alkyl-, or R1 is a phenyl group substituted by two R such as above defined;

in group 8, R1 is an heterocycle selected in the group comprising pyrazolyl, triazolyl, pyridyl, pyrimidinyl;

in group 9, R1 is an aromatic or non aromatic heterocycle such as above defined substituted by R which is selected in the group comprising $C_1$-$C_{10}$alkyl-O—, $NH_2$, $C_1$-$C_{10}$alkyl-CO—, $C_1$-$C_{10}$alkyl-$SO_2$—, Cl-$C_1$-$C_{10}$alkyl-O—$C_6H_4$—, heterocycle such as pyridyl, $C_6H_4$—$CH_2$— or $R_aOOC$—, with Ra being such as above defined;

in group 10, R1 is CHO—;

in group 11, R1 is $COOR_a$—;

in group 12, R1 is $CONR_aR_b$—;

in group 13, R1 is $S(O)_nR_a$—.

Several groups will be also distinguished for R1, when Y=C and W is N, their numbering being not linked to their therapeutical interest;

in group 14, R1 is H or $C_1$-$C_{10}$alkyl substituted by R, with R being such as above defined;

in group 15, R1 represents a phenyl group substituted or not by R, with R being such as above defined.

In the above defined groups, when Y=N and W is C or Y=C and W=N, R3 is advantageously H, $NR_aR_b$, halogen, $C_1$-$C_{10}$alkyl, with $R_a$ and $R_b$ being such as above defined.

In the above defined groups, when Y=N and W is C or Y=C and W=N, R4 is advantageously H or a phenyl substituted by R, with R being such as above defined.

In the above defined groups, in more preferred molecules, R2 is $CF_3$, $CF_3O$, $CF_3$—$C_6H_4$, $CH_3S$, $CH_3$—$CH_2$—S, Br or H, In the above defined groups, in more preferred molecules, R5 is H.

In the above defined groups, when —Y=N and W is C or Y=C and W=N, R1, R2, R3 and R4 being such as above defined, R5 is advantageously $COR_a$, $CO_2Ra$, $P(O)(OH)_2$ or $COCHR_aNR_bR_c$.

The invention more particularly relates to derivatives with $IC_{50}$ lower than or equal to 2.5 µM.

Illustrative of this embodiment are derivatives wherein:
R1=H, I, Br, CH2=CH—, phenyl, phenyl substituted by $CH_3$—CO—NH—, $NH_2$—$SO_2$—, $CH_3O$—, $CH_3$—$SO_2$—NH—, morpholino, $CH_3$—NH—CO—, $HOCH_2$—, $NH_2$—$CH_2$—, both $NH_2$— and $CH_3$—O—, or R1 is pyrazolyl, pyrazolyl substituted by $CH_3$—O—$C_6H_4$—, pyridyl substituted by $CH_3$—O—, triazolyl, triazolyl substituted by $C_6H_4$—$CH_2$—, pyrimidinyl substituted by $NH_2$ or R1 piperazinyl substituted by $CH_3SO_2$—, $CH_3CO$;
R2=$CF_3$, $CF_3$—$C_6H_4$—, $CF_3$—O—;
R3=R4=R5=H;
Y=N et W=C The derivatives of the invention are further characterized by the following properties: they are able to inhibit the activity of de DltA enzyme and they are able to render resistant bacteria sensitive to antibacterial cationic peptides and peptides mimicking said cationic peptides such as colistin in vitro; they are active in preventing bacterial multiplication in an experimental model of infection in mice model by rendering the bacteria avirulent.

The invention thus also relates to a composition comprising at least a derivative of formula (I) such as above defined for use as drug.

It particularly relates to a composition for use as antibacterial agent against Gram-positive bacteria, such as bacteria of the genus *Staphylococcus, Bacillus, Listeria, Enterococcus, Streptococcus, Mycobacterium, Bacteroides* and *Clostridium*. Such a composition is particularly efficient to treat infections due to *Staphylococcus aureus Enterococcus faecalis, Enterococcus faecium, Mycobacterium tuberculosis, Streptococcus pyogenes, Streptococcus pneumoniae, Streptococcus agalactiae, Bacteroides fragilis,* and *Clostridium difficile*.

It also relates to a pharmaceutical composition comprising an effective amount of at least a derivative of formula (I) such as above defined, in combination with a pharmaceutically acceptable carrier.

Said pharmaceutical compositions are formulated to be administered for example under oral, injectable, parenteral routes, with individual doses appropriate for the patient to be treated.

The invention also relates to a method of treatment of microbial infections which comprises administering to a patient in need thereof an efficient amount of a pharmaceutical composition such as above defined.

The method for assessing the Dlta inhibitory activity of the tested molecules in vitro is also covered by the invention.

Said method comprises:
pre-incubating in a buffer the compound to be assessed, a recombinant Dlta enzyme, and
starting the catalysed reaction by addition of D-alanine, ATP and a thiol selected in the group comprising DTT, coenzyme A and N-acetylcysteamine, used as enzyme substrate instead of the natural substrate DltC protein, or alternatively adding the thiol at the pre-incubation step, adding the revelation agents reagents of the luminescent or fluroresent assays to detect the ATP used or the AMP produced during the DltA enzymatic reaction.

Alternatively, the thiol is added at the pre-incubation step.

The luminescent assay is carried out with luciferase, D-luciferin and N-acetylcysteamine, the luminescence intensity being measured and the variation of intensity induced by the compound effect is converted into inhibition percentage.

The fluorescent assay is carried out with adenylate kinase, pyruvate Kinase, phosphoenolpyruvate, lactate deshydrogenase and NADH, these revelation agents being either added with the substrates to follow the reaction in real time, or at the end of the incubation time to get endpoint data, the fluorescence intensity of NADH being measured and the variation of intensity induced by the compound effect is converted into inhibition percentage.

The invention also relates to a method for measuring the efficacy of molecules in inhibiting bacteria proliferation in vitro, which comprises each of the following steps:

measuring the Minimum Inhibitory Concentration (MIC) of the compounds for the considered bacteria, according to the Clinical and Laboratory Standards Institute (CLSI) guidelines;

measuring the minimal concentration of the compound at which no visible bacterial growth is observed in the presence of an antibacterial peptide or a peptide mimicking such a peptide at a sub-inhibitory concentration, which is called Minimum Antivirulence Concentration (MAC);

comparing the MIC (pure antibiotic properties) of studied compound to its MAC (Antivirulence, or effective sensitizing concentration of said compound);

selecting the antivirulence molecules as being capable of inhibiting bacterial growth in presence of an antibacterial peptide or a peptide mimicking its effect and not inhibiting the growth in the absence of said peptide.

The invention also relates to a process for the synthesis of the above defined molecules of formula (I).

Said process comprises making compounds of formula (I) by derivatization of the R1, R2, R3, R4 or R5 groups of other compounds of formula (I) by known methods for the one skilled in the art.

As illustrative and non restrictive examples: R1 being $C_2$-$C_{10}$alkynyl can be transformed into R1=heterocycle being optionally substituted by one or several R by known cycloaddition methods using an azide or a diazonium derivative. R1 being $C_2$-$C_{10}$alkenyl can be oxidized into R1=$COR_a$ by known oxidation methods using as a non restrictive example, $NaIO_4$ and osmium salts; R5 being H can be acylated to R5=$COR_a$, $CO_2R_a$ or $COCHR_aNR_bR_c$ by known acylation methods.

Thus, compounds of formula (I) can be obtained by derivatizating the R1 groups,
into an optionally substituted heterocycle by cycloaddition methods using an azide or a diazonium derivative when R1 is $C_2$-$C_{10}$alkynyl;
into R1=$COR_a$, by oxidation methods using salts such as $NaIO_4$ and osmium salts when R1 is $C_2$-$C_{10}$alkenyl.

According to an embodiment of the invention, compounds of formula (I) in which Y=N and W=C are obtained by adding a compound of formula (II) to a derivative of formula (III) according to scheme 1:

Scheme 1

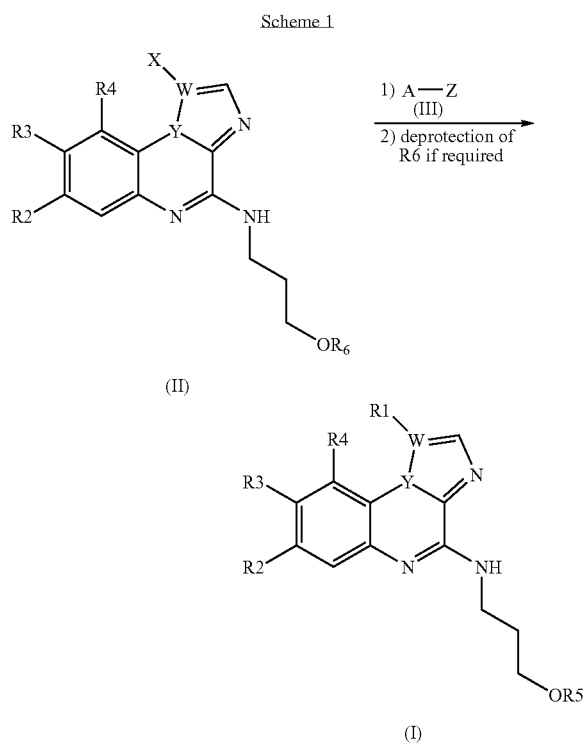

wherein
Y=N and W=C
X=Cl, Br, I
A=$C_2$-$C_{10}$alkenyl, $C_2$-$C_{10}$alkynyl, CN, COR$_a$, phenyl or heterocycle, all being optionally substituted by one or several R or optionally substituted by a silyl group
Z=Cl, Br, I, H, optionally substituted boron, optionally substituted tin or optionally substituted zinc
R6=R5 or suitable protecting group such as silyl or tetrahydro-2H-pyran-5-yloxy
R, Ra, R1, R2, R3, R4, R5 being such as above defined.

When Z is Cl, Br or I, compounds of formula (I) can be prepared by stirring compound of formula (III) (1 eq), bis(pinacolato)diboron (1-2 eq), a suitable base, usually potassium acetate (1-6 eq), a suitable palladium catalyst with its ligands (usually Pd(dppf)Cl$_2$.DCM 1-30 mol %) in a degassed solvent (usually dimethylformamide) at 60-120° C. for 1-16 h under inert atmosphere, then cooling down to room temperature, adding compound of formula (II) (0.5-2 eq) with base (usually an aqueous solution of sodium or potassium carbonate, 1-6 eq) and a suitable palladium catalyst with its ligands (usually Pd(PPh$_3$)$_4$ 1-30 mol %) and stirring under inert atmosphere at 60-120° C. for 2 to 48 h.

When Z is Cl, Br, I or H, compounds of formula (I) can be prepared by stirring compound of formula (II) in appropriate conditions with an alkyl lithium reagent, non restrictive examples being n-BuLi, s-BuLi or t-BuLi, then adding optionally a transmetalating agent based on a zinc, magnesium, copper, tin or boron reagent, non restrictive examples being ZnCl$_2$, MgBr$_2$, MgCl$_2$, B(OMe)$_3$, bis(pinacolato)diboron, and finally adding compound of formula (III) in appropriate conditions with the optional use of a suitable palladium catalyst with its ligands, non restrictive examples being Pd(PPh$_3$)$_4$ or Pd(dppf)Cl$_2$.DCM.

When Z is H and A is $C_2$-$C_{10}$alkenyl or $C_2$-$C_{10}$alkynyl, compounds of formula (I) can be prepared by stirring compound of formula (II) (1 eq), a suitable palladium catalyst and/or copper catalyst (1-30 mol %) with its ligands, compound of formula (III) (1-3 eq), and a suitable base (usually sodium or potassium carbonate, 1-6 eq) in a degassed solvent or solvent mixture at 20-120° C. for 1 to 48 h under inert atmosphere.

When Z is an optionally substituted boron, tin or zinc, compounds of formula (I) can be prepared by stirring compound of formula (II) (1 eq), a suitable palladium catalyst (1-30 mol %) with its ligands, compound of formula (III) (1-3 eq), and a suitable base (usually sodium or potassium carbonate, 1-6 eq) in a degassed solvent or solvent mixture at 20-120° C. for 1 to 48 h under inert atmosphere.

When R1 is $CO_2R_a$ or $CONR_aR_b$, compounds of formula (I) can be obtained directly from compounds of formula (II) under known carbonylation conditions using one or several atmospheres of carbon monoxide with a suitable palladium catalyst with its ligands, non restrictive examples being Pd(OAc)$_2$ with diphenylphosphinoferrocene or PdCl$_2$(rac-BINAP).

When R6 is a protecting group; it can be deprotected by known methods. As a non restrictive example, when R6 is a silyl group, it can be converted into H by using a suitable fluoride reagent or suitable acidic conditions.

In another embodiment of the invention, compounds of formula (I) can also be obtained by reacting compounds of formula (IV) with compounds of formula (III) according to scheme 2, in a process similar to the ones described above for scheme 1:

Scheme 2

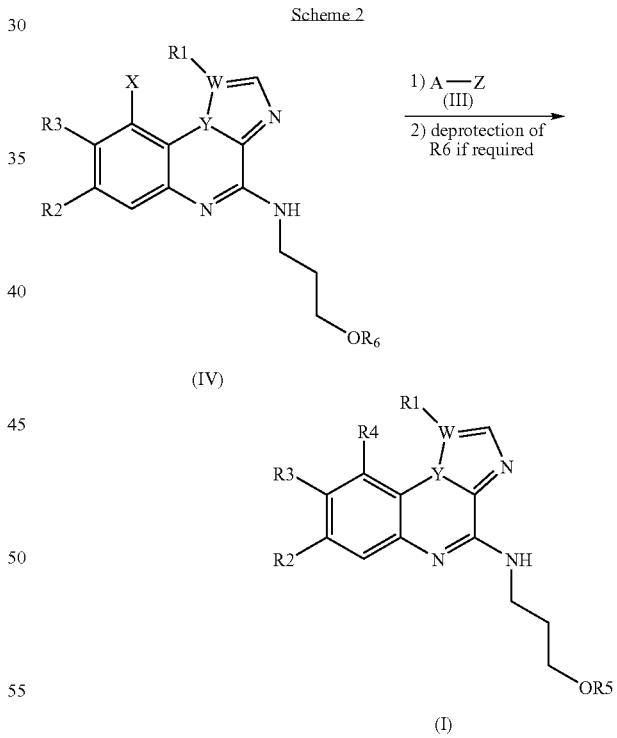

wherein
Y=N and W=C
X=Cl, Br, I
A=$C_2$-$C_{10}$alkenyl, $C_2$-$C_{10}$alkynyl, CN, COR$_a$, phenyl or heterocycle, all being optionally substituted by one or several R or optionally substituted by a silyl group
Z=Cl, Br, I, H, optionally substituted boron, optionally substituted tin or optionally substituted zinc,
R6=R5 or suitable protecting group such as silyl,
R, Ra, R1, R2, R3, R4, R5 being such as above defined.

In still another embodiment, compounds of formula (I) can also be obtained by reacting compounds of formula (V) with compounds of formula (III) according to scheme 3, in a process similar to the ones described above for scheme 1:

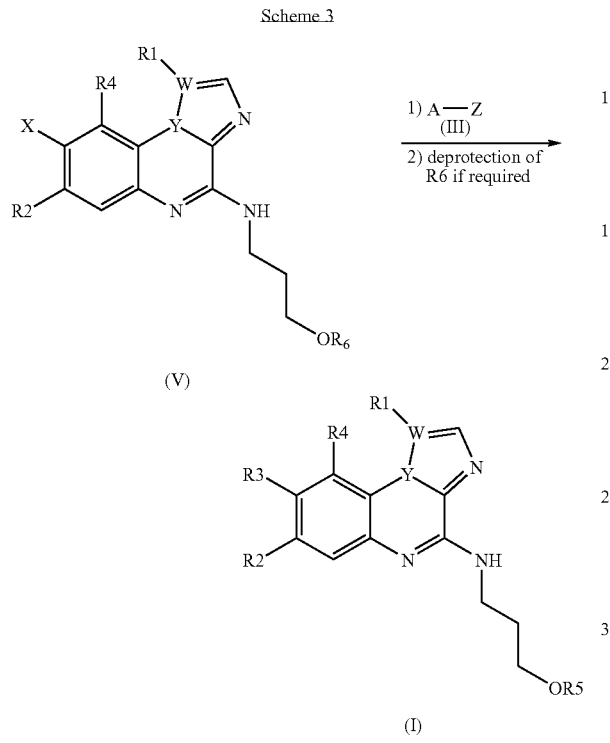

(V)

(I)

wherein
Y=N and W=C
X=Cl, Br, I
A=$C_2$-$C_{10}$alkenyl, $C_2$-$C_{10}$alkynyl, CN, COR$_a$, phenyl or heterocycle, all being optionally substituted by one or several R or optionally substituted by a silyl group
Z=Cl, Br, I, H, optionally substituted boron, optionally substituted tin or optionally substituted zinc,
R6=R5 or suitable protecting group such as silyl,
R, R$_a$, R1, R2, R3, R4, R5 being such as above defined.

In another embodiment, compounds of formula (I) can also be obtained by reacting compounds of formula (VI) with compounds of formula (III) according to scheme 4, in a process similar to the ones described above for scheme 1:

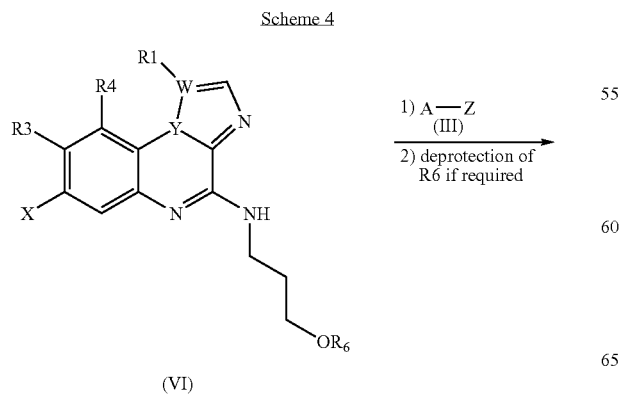

(VI)

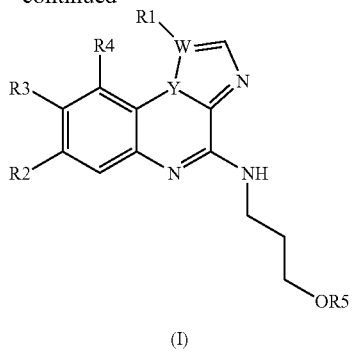

(I)

wherein
Y=N and W=C
X=Cl, Br, I
A=$C_2$-$C_{10}$alkenyl, $C_2$-$C_{10}$alkynyl, CN, COR$_a$, SR$_a$, phenyl or heterocycle, all being optionally substituted by one or several R or optionally substituted by a silyl group
Z=Cl, Br, I, H, optionally substituted boron, optionally substituted tin or optionally substituted zinc,
R6=R5 or suitable protecting group such as silyl,
R, Ra, R1, R2, R3, R4, R5 being such as above defined.

Compounds of formula (II) can be obtained by halogenating compounds of formula (VII) according to scheme 5:

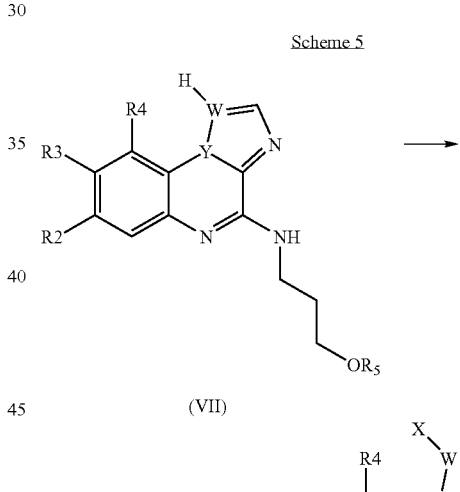

(VII)

(II)

wherein
Y=N and W=C
X=Cl, Br, I
R2, R3, R4, R5 being such as above defined.

Known halogenation reagents can be advantageously used here, such as N-chlorosuccinimide, N-bromosuccinimide, N-iodosuccinimide or Selectfluor™ with iodide.

Alternatively, compounds of formula (II) can also be obtained by reacting compounds of formula (VIII) with propanolamine derivatives of formula (IX) according to scheme 6:

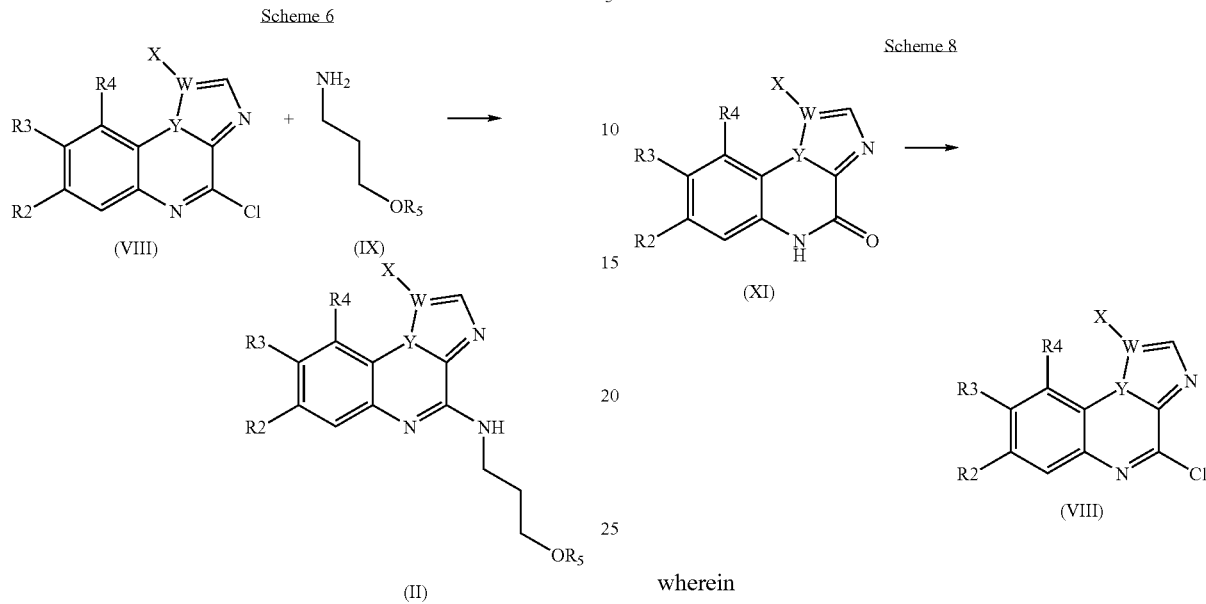

wherein
Y=N and W=C
X=Cl, Br, I
R2, R3, R4, R5 being such as above defined.

This reaction is advantageously carried out under classical nucleophilic substitution conditions in the presence of a suitable solvent and a suitable base.

Compounds of formula (VIII) can themselves be obtained by halogenating the corresponding 4-chloroimidazo[1,2-a]quinoxaline (X) by known halogenation methods including the use of N-chlorosuccinimide, N-bromosuccinimide, N-iodosuccinimide or Selectfluor™ with iodide according to scheme 7:

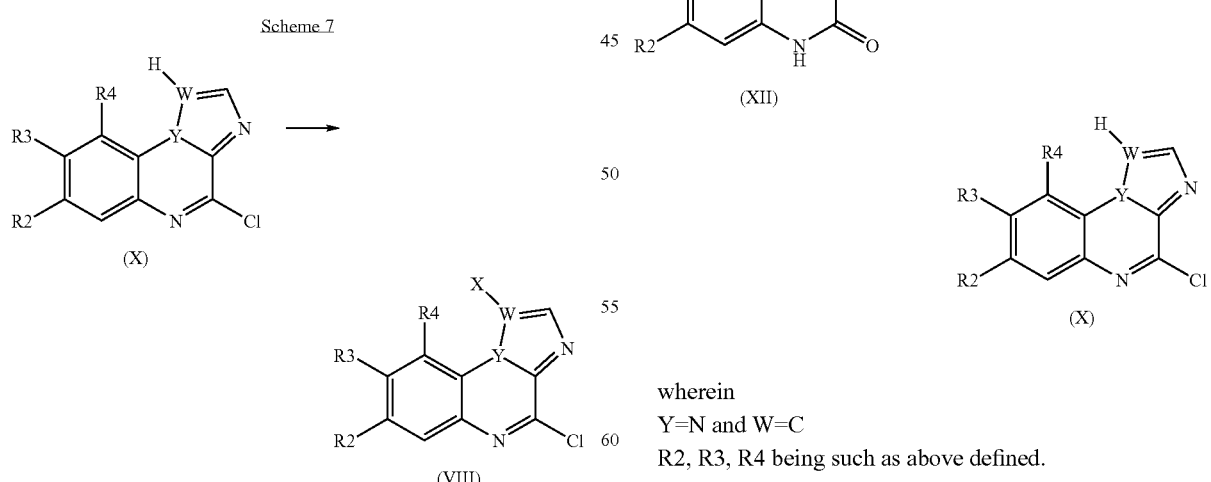

wherein
Y=N and W=C
X=Cl, Br, I
R2, R3, R4 being such as above defined

Alternatively, compounds of formula (VIII) can also be obtained by reacting the corresponding imidazo[1,2-a]quinoxalin-4-one (XI) by known halogenation methods including the use of phosphorus oxychloride according to scheme 8:

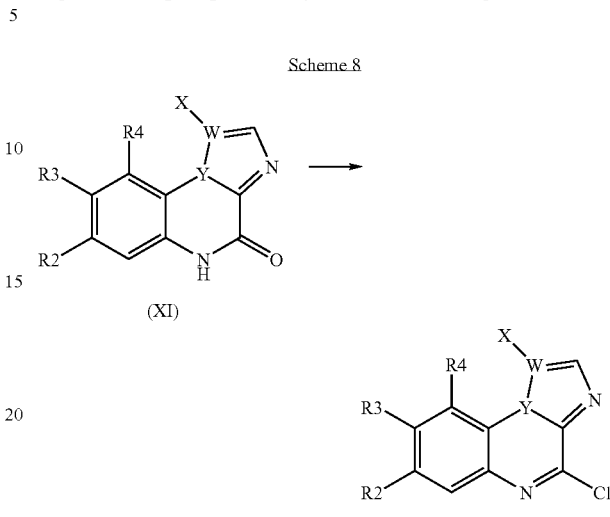

wherein
Y=N and W=C
X=Cl, Br, I
R2, R3, R4 being such as above defined.

Compounds of formula (X) can themselves be obtained by reacting the corresponding imidazo[1,2-a]quinoxalin-4-one (XII) by known halogenation methods including the use of phosphorus oxychloride according to scheme 9:

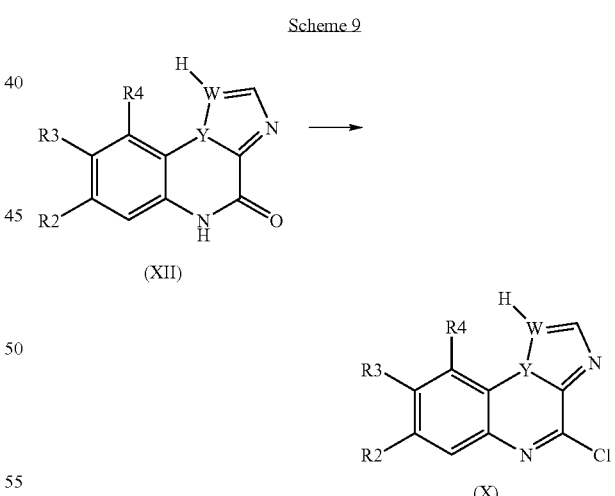

wherein
Y=N and W=C
R2, R3, R4 being such as above defined.

Compounds of formula (XI) can themselves be obtained by halogenating the corresponding imidazo[1,2-a]quinoxalin-4-one (XII) by known halogenation methods including the use of N-chlorosuccinimide, N-bromosuccinimide, N-iodosuccinimide or Selectfluor™ with iodide according to scheme 10:

Scheme 10

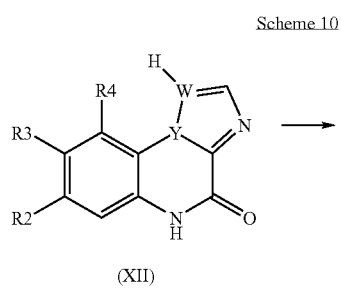

(XII)

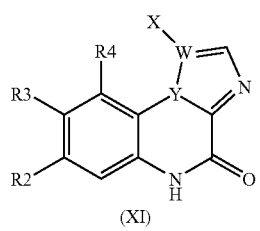

(XI)

wherein
Y=N and W=C
X=Cl, Br, I
R2, R3, R4 being such as above defined.

Compounds of formula (I) can also be obtained according to scheme 11 from imidazo[1,2-a]quinoxalin-4-ones of formula (XIII) either directly by reacting under appropriate conditions such as the ones described in Eur. J. Med. Chem. 1998, 33, 943 hexamethyldisilazane, ammonium sulfate and a propanolamine derivative of formula (IX), or in two steps by known halogenation, mesylation or tosylation of imidazo[1,2-a]quinoxalin-4-ones of formula (XIII) followed by classical nucleophilic substitution with a propanolamine derivative of formula (IX):

Scheme 11

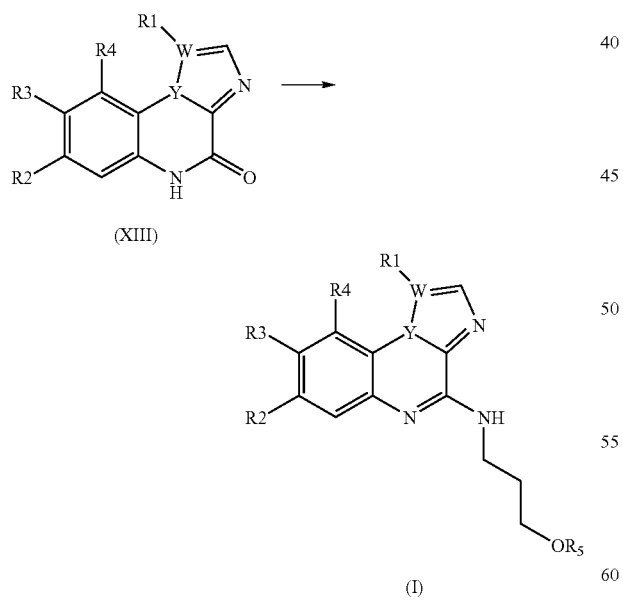

wherein
Y=N and W=C
R1, R2, R3, R4, R5 being such as above defined.

Imidazo[1,2-a]quinoxalines of formula (IV, V, VI and VII) can be obtained from imidazo[1,2-a]quinoxalin-4-ones of formula (XII) by suitable mesylation, tosylation or halogenation such as the one described in scheme 9 followed by classical nucleophilic substitution with the appropriate amine such as the one described in scheme 6.

Imidazo[1,2-a]quinoxalin-4-ones of formula (XII or XIII) can be obtained by methods known to the art, such as the non-limiting ones published in J. Med. Chem. 1991, 34, 2571, J. Med. Chem. 1997, 40, 2053 and J. Med. Chem. 1999, 42, 4362.

Compounds of formula (I) in which Y=C and W=N can be obtained according to scheme 12 by substituting amines of formula (XIV) to 2,4-dichloro-3-nitroquinolines of formula (XV) using methods known to the art, such as the non-limiting ones published in J. Med. Chem. 1975, 18, 726 and Bioorg. Med. Chem. 2003, 11, 2541:

Scheme 12

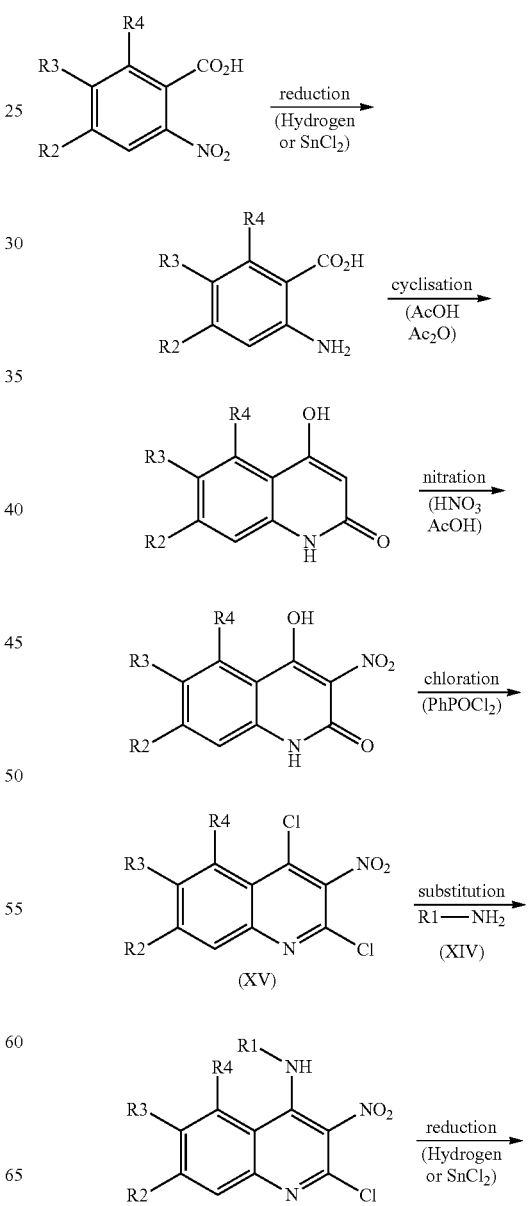

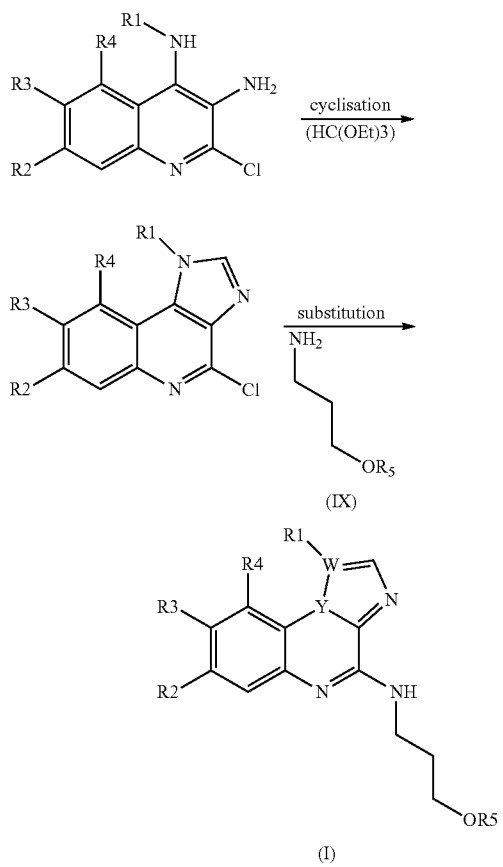

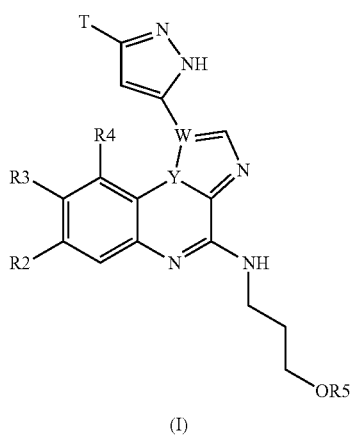

wherein

Y=C and W=N

R1, R2, R3, R4, R5 being such as above defined

Compounds of formula (I) in which Y=N, W=C and R1=pyrazolyl can be obtained according to scheme 13 by substituting alkynes of formula (XVI) with chlorocarbonyls of formula (XVII) in the presence of a suitable copper or palladium catalyst and subsequently cyclizing with hydrazine using methods known to the art, such as the non-limiting ones published in J. Org. Chem. 1983, 48, 4887:

wherein

Y=N and W=C

T is selected from the group consisting of $C_1$-$C_{10}$alkyl, $C_2$-$C_{10}$alkenyl, $C_2$-$C_{10}$alkynyl, phenyl and heterocycle; all being optionally substituted by one or several identical or different R, R, R2, R3, R4 being such as above defined with respect to formula (I).

R6=R5 or suitable protecting group such as silyl or tetrahydro-2H-pyran-5-yloxy

Compounds of formula (I) in which Y=N, W=C and R1=pyrazolyl can be obtained according to scheme 14 by substituting alkynes of formula (XVIII) with diazomethane derivatives of formula (XIX) in the presence of a fluoride source when V is a silyl group using methods known to the art, such as the non-limiting ones published in J. Org. Chem. 1990, 55, 5535:

Scheme 13

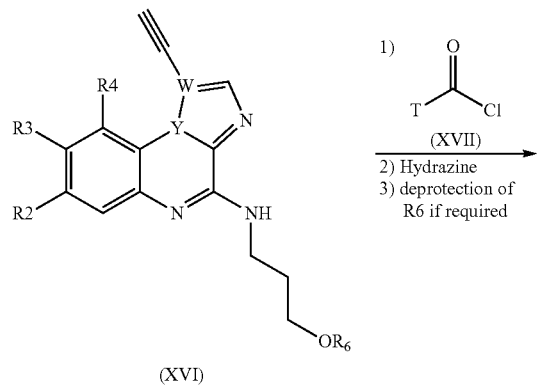

Scheme 14

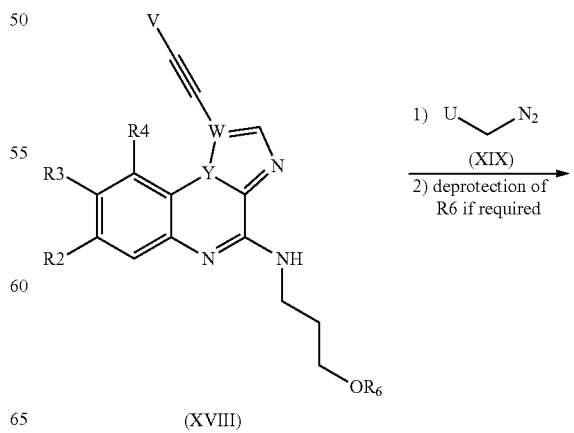

-continued

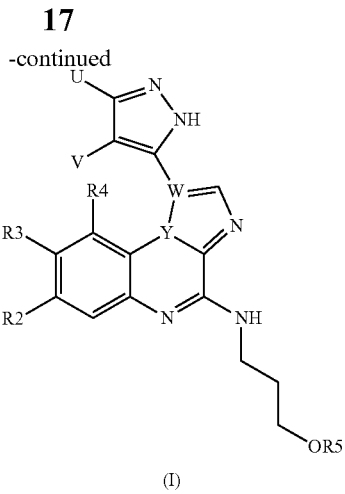

(I)

wherein
Y=N and W=C
V=H, Cl, Br, I, Ra, CORa, CO2Ra, CONRaRb or a silyl group
U=H, CORa, CO2Ra, CONRaRb or a silyl group
Ra, Rb, R2, R3, R4, R5 being such as above defined with respect to formula (I).
R6=R5 or a suitable protecting group such as silyl or tetrahydro-2H-pyran-5-yloxy Other characteristics and advantages of the invention are given in the following examples to illustrate the invention, without limiting its scope.

Figure 1A:
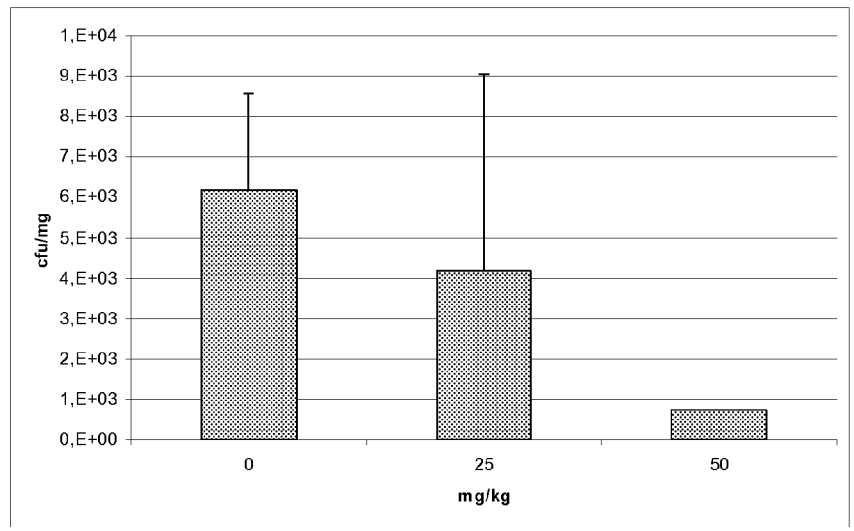
FIG. 1A shows the effect of the quinoxaline derivative of example 8 in an in vivo assay with the experimental model of systemic infection by S. agalactiae.
Figure 1B:
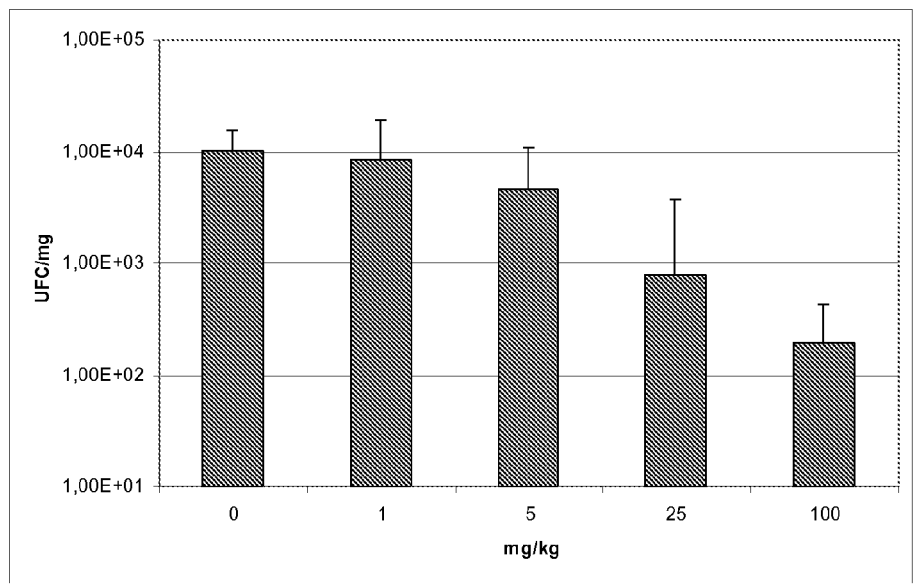
FIG. 1B shows the effect of the quinoxaline derivative of example 14 in an in vivo assay with the experimental model of systemic infection by S. agalactiae.
Figure 1C:
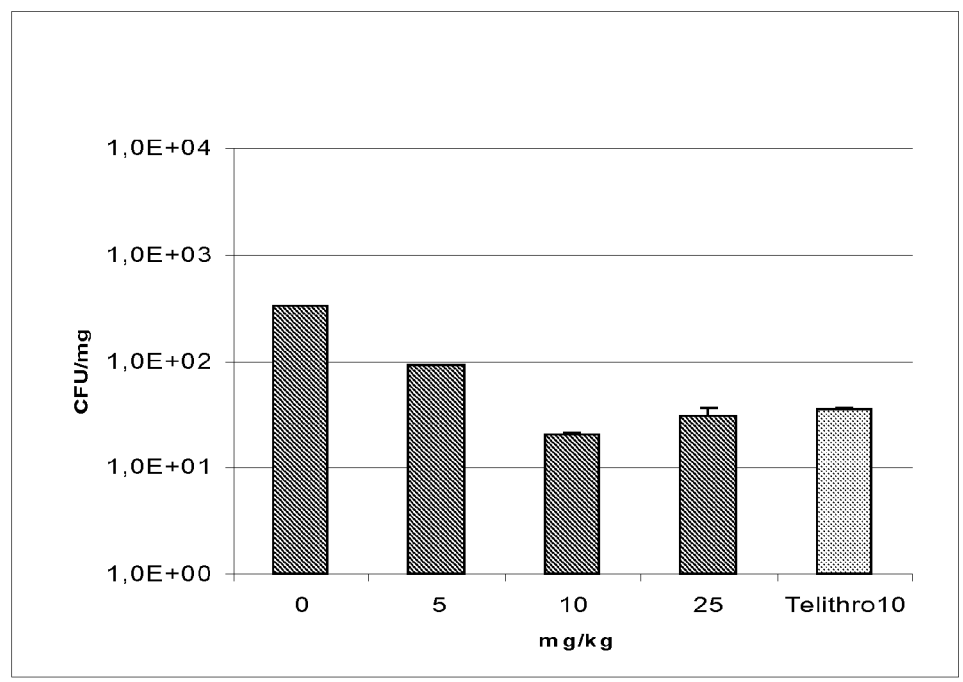
FIG. 1C shows the effect of the quinoxaline derivative of example 16 in an in vivo assay with the experimental model of systemic infection by S. agalactiae.
Figure 1D:
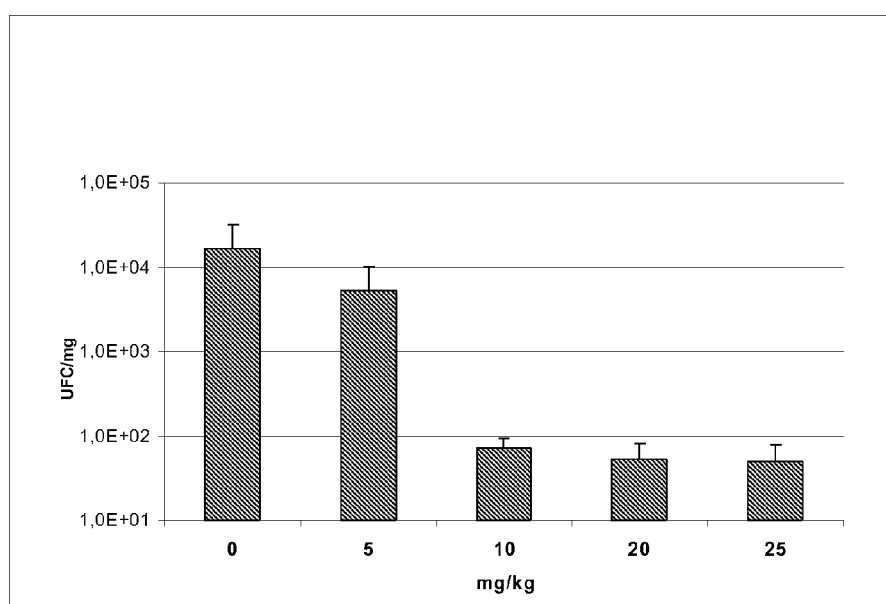
FIG. 1D shows the effect of the quinoxaline derivative of example 19 in an in vivo assay with the experimental model of systemic infection by S. agalactiae.

In these examples, it is referred to FIG. 1A to 1C, which represent the effect of a quinoxaline derivative of the invention on the bacteraemia due to GBS.

Proton nuclear magnetic resonance ($^1$H NMR) spectra were recorded at either 300 or 400 MHz, and chemical shifts are reported in parts per million (δ) downfield from the internal standard tetramethylsilane (TMS). Abbreviations for NMR data are as follows: s=singlet, d=doublet, t=triplet, q=quadruplet, qt=quintuplet, se=sextuplet, m=multiplet, dd=doublet of doublets, dt=doublet of triplets, br=broad. J indicates the NMR coupling constant measured in Hertz. CDCl₃ is deuteriochloroform, DMSO-d$^6$ is hexadeuteriodimethylsulfoxide, and CD₃OD is tetradeuteriomethanol. Mass spectra were obtained using either electrospray (ESI) or atmospheric pressure photoionization (APPI) techniques. Analtech Silica Gel GF and E. Merck Silica Gel 60 F-254 thin layer plates were used for thin layer chromatography. Flash chromatography was carried out on Flashsmartpack cartridge, irregular silica 40-60 μm or spherical silica 20-40 μm.

Certain compounds are abbreviated herein. Selectfluor™ refers to 1-chloromethyl-4-fluoro-1,4-diazoniabicyclo[2.2.2]octane bis(tetrafluoroborate), Pd/C refers to a palladium on carbon catalyst.

TLC refers to thin layer chromatography, MS refers to mass spectra, HPLC refers to high pressure liquid chromatography, NMR refers to nuclear magnetic resonance, APT refers to attached proton test, HSQC refers to heteronuclear single quantum correlation, NOESY refers to nuclear Overhauser enhancement spectroscopy.

PART A

Synthesis

Examples 1 to 59 illustrate methods of synthesis of derivatives according to the invention.

Example 1

3-{[7-(trifluoromethyl)imidazo[1,2-a]quinoxalin-4-yl]amino}propan-1-ol

Step 1: Synthesis of 1-[2-nitro-4-(trifluoromethyl)phenyl]-1H-imidazole

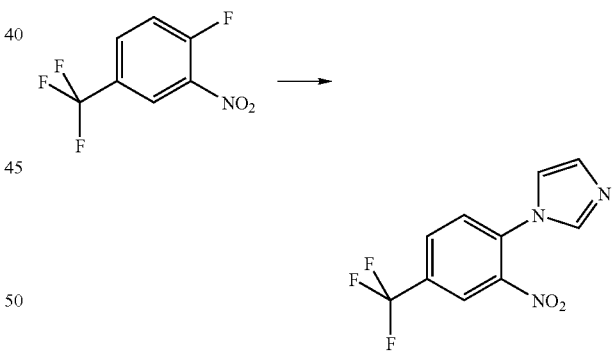

To a solution of 1-fluoro-2-nitro-4-(trifluoromethyl)benzene (15.00 g; 71.8 mmol; 1 eq) and diisopropylethylamine (12.5 mL; 71.8 mmol; 1 eq) in anhydrous acetonitrile (650 mL), imidazole (4.88 g; 71.8 mmol; 1 eq) is added under argon. The reaction mixture is allowed to stir under reflux for 20 hours until 1-fluoro-2-nitro-4-(trifluoromethyl)benzene has completely reacted. The crude mixture is concentrated under vacuum and the resulting powder dissolved in ethyl acetate (250 mL). The organic phase is then washed with water (100 mL), brine (100 mL) and dried over sodium sulfate to provide an orange powder after concentration under vacuum. Further purification by flash chromatography on silica gel (ethyl acetate/cyclohexane 5:5) afforded the title compound (17.7 g; 68.5 mmol; 96%) as a brown powder.

$^1$H NMR (CDCl$_3$), δ (ppm): 8.59 (s, 1H), 8.29 (dd, J=8.3 and 1 Hz, 1H), 7.99 (s, 1H), 7.97 (d, J=8.3 Hz, 1H), 7.49 (d, J=1 Hz, 1H), 7.14 (s, 1H).

Step 2: Synthesis of
2-(1H-imidazol-1-yl)-5-(trifluoromethyl)aniline

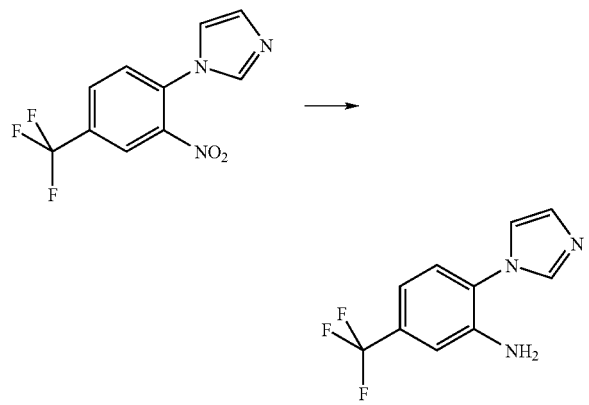

To a solution of 1-[2-nitro-4-(trifluoromethyl)phenyl]-1-imidazole (20.0 g; 77.8 mmol; 1 eq) in ethanol (600 mL) dehydrated tin chloride (87.7 g; 388.8 mmol; 5 eq) is added. The resulting reaction mixture is allowed to stir under reflux for 2 hours until completion of the reaction. The crude reaction mixture is then concentrated under vacuum and the resulting residue is dissolved in water (500 mL). The aqueous phase is basified until pH 9 is reached with solid hydrogen carbonate. The aqueous phase is then extracted twice with ethyl acetate (2×500 mL). The organic phases are combined, dried over sodium sulfate and concentrated under vacuum to provide a beige powder. Purification by chromatography on silica gel (cyclohexane/ethyl acetate 1:9), afforded the title compound (17.3 g; 76.2 mmol; 98%) as a white powder.

$^1$H NMR (DMSO-d$_6$), δ (ppm): 8.64 (d, J=1 Hz, 1H), 7.38 (t, J=1.5 Hz, 1H), 7.26 (d, J=7.8 Hz, 1H), 7.20 (d, J=2 Hz, 1H), 7.14 (d, J=1 Hz, 1H), 6.93 (dd, J=7.8 and 2 Hz, 1H), 5.50 (br s, 2H)

Step 3: Synthesis of 7-(trifluoromethyl)imidazo[1,2-a]quinoxalin-4(5H)-one

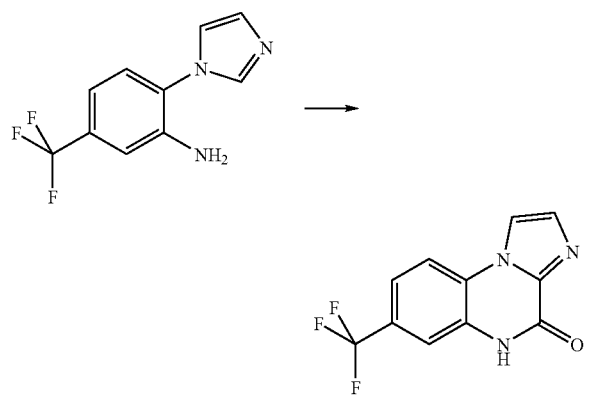

To a solution of 2-(1H-imidazol-1-yl)-5-(trifluoromethyl) aniline (17.00 g; 74.8 mmol; 1 eq) in anhydrous 1,2-dichlorobenzene (375 mL), commercially available carbonyldiimidazole (24.72 g; 149.7 mmol; 2 eq) is added under an argon atmosphere. This reaction mixture is allowed to stir under reflux for 2 hours. The expected quinoxalinone precipitates as a grey powder during the reflux. The initial crystal clear solution quickly turns black after heating and becomes non homogeneous. This crude reaction mixture is allowed to precipitate at 4° C. during 48 hours. The grey powder formed is then filtered off on a fritted glass. This solid is transferred in a 1 L flask, diluted in fresh ethyl acetate (500 mL) and heated to gentle reflux for two hours. Hot filtration and then several washings of the solid with diethyl ether afforded the title compound (14.28 g; 56.4 mmol; 75%) as a grey powder.

$^1$H NMR (DMSO-d$_6$), δ (ppm): 12.06 (br s, 1H), 6.64 (m, 1H), 8.34 (d, J=8.8 Hz, 1H), 7.66 (m, 3H)

Step 4: Synthesis of 4-chloro-7-(trifluoromethyl) imidazo[1,2-a]quinoxaline

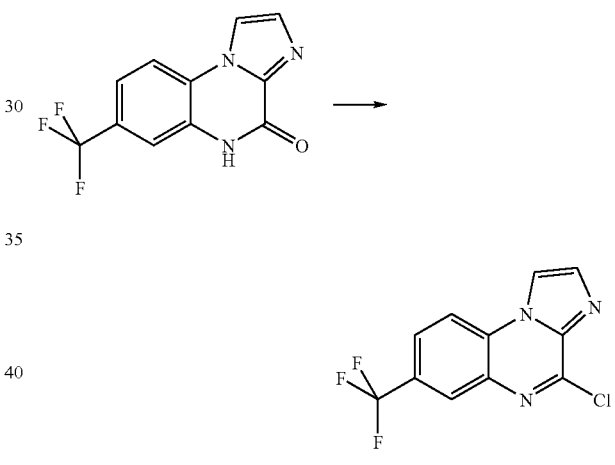

To a suspension of 7-(trifluoromethyl)imidazo[1,2-a]quinoxalin-4(5H)-one (5.00 g; 19.75 mmol; 1 eq) in phosphorus oxychloride (130 mL) is added under argon dimethylaniline (14.2 mL). The reaction mixture is allowed to stir for 1 h30 under reflux. The reaction mixture becomes homogeneous but turns black. The phosphorus oxychloride is evaporated under argon and the viscous residue is diluted in ethyl acetate (200 mL) and concentrated under vacuum. This operation is repeated twice until a grey powder is obtained. This powder is then dissolved in hot ethyl acetate (200 mL), washed with brine (100 mL), dried over sodium sulfate and concentrated under vacuum to provide a yellowish powder (8.50 g). Further purification by flash chromatography on silica gel (chloroform 100%) afforded the title compound (3.80 g; 13.5 mmol; 68%) The beige powder obtained is engaged as such without further purification.

$^1$H NMR (DMSO-d$_6$), δ (ppm): 9.05 (d, J=1 Hz, 1H), 8.63 (d, J=8.8 Hz, 1H), 8.35 (m, 1H), 8.13 (dd, J=8.8 and 2 Hz, 1H), 7.94 (m, 1H)

Step 5: Synthesis of 3-{[7-(trifluoromethyl)imidazo[1,2-a]quinoxalin-4-yl]amino}propan-1-ol

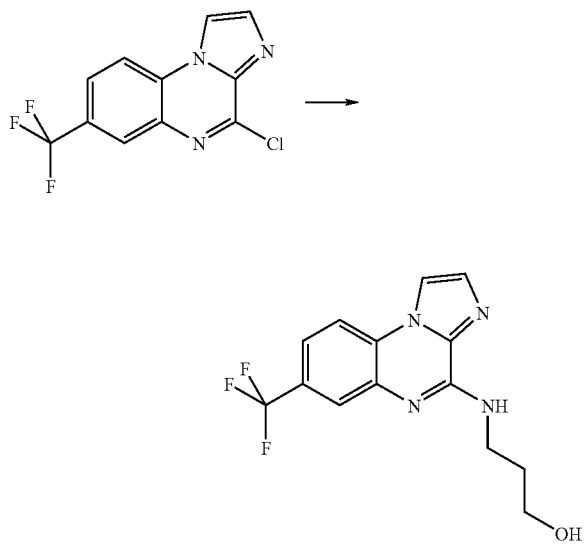

To a solution of 4-chloro-7-(trifluoromethyl)imidazo[1,2-a]quinoxaline (2.00 g; 7.36 mmol; 1 eq) in anhydrous dioxane (250 mL), 3-aminopropanol (6.2 mL; 81.0 mmol; 11 eq) is added, under argon atmosphere. Complete conversion was achieved after 17 hours of stirring under reflux. The initially cloudy yellow solution turns first orange and then becomes translucid. The reaction mixture is cooled to room temperature and diluted in ethyl acetate (500 mL). The organic phase is washed three times with a solution of saturated sodium hydrogenocarbonate (3×330 mL). The organic phases are combined, dried over sodium sulfate and concentrated under vacuum to provide pure title compound (1.94 g; 6.25 mmol; 85%) as a grey powder.

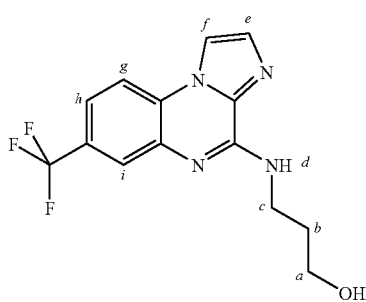 [SMILES: OCCCNc1nc2cc(C(F)(F)F)ccc2n2ccnc12]

$^1$H NMR (DMSO-d$_6$), δ (ppm): 8.68 (s, 1H, f), 8.29 (d, J=8.8 Hz, 1H, g), 8.04 (t, J=5.4 Hz, 1H, d), 7.81 (s, 1H, i), 7.66 (s, 1H, e), 7.58 (d, J=8.8 Hz, 1H, h), 4.64 (t, J=5.4 Hz, 1H, —OH), 3.63 (q, J=6.3 Hz, 2H, c), 3.53 (q, J=6.3 Hz, 2H, a), 1.83 (qt, J=6.3 Hz, 2H, b) as determined by HSQC and NOESY.

An important NOE correlation is observed between g and f.

APPI-MS m/z 311 (M+H)$^+$

Example 2

3-{[1-bromo-7-(trifluoromethyl)imidazo[1,2-a]quinoxalin-4 yl]amino}propan-1-ol

Step 1: Synthesis of 1-bromo-4-chloro-7-(trifluoromethyl)imidazo[1,2-a]quinoxaline

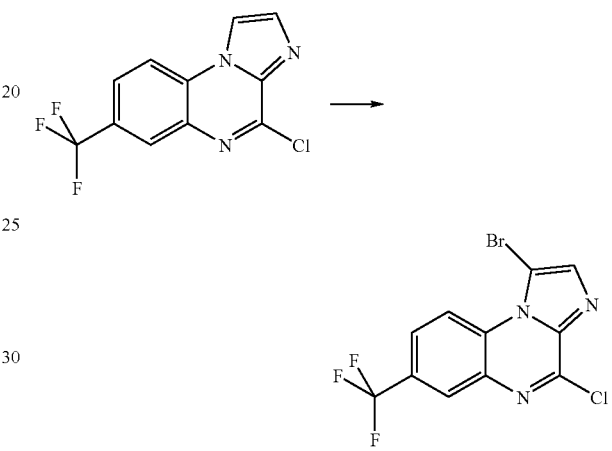

To a suspension of 4-chloro-7-(trifluoromethyl)imidazo[1,2-a]quinoxaline (10.00 g; 36.8 mmol; 1 eq) in anhydrous methylene chloride (184 mL) N-bromosuccinimide (9.83 g; 55.2 mmol; 1.5 eq) is added under argon atmosphere. The reaction mixture quickly turns green, then yellow, and a precipitate appears. The crude mixture is heated to 35° C. and is allowed to stir over a period of 17 hours at this temperature. During that time, the mixture becomes translucid. The solution is then concentrated under vacuum, and the beige powder obtained is further purified by flash chromatography on silica gel (methylene chloride/cyclohexane 8:2) to afford the pure title compound (11.57 g; 33.0 mmol; 90%) as a white powder.

$^1$H NMR (DMSO-d$_6$), δ (ppm): 9.35 (d, J=8.8 Hz, 1H), 8.41 (s, 1H), 8.17 (d, J=8.8 Hz, 1H), 8.06 (s, 1H)

Step 2: 3-{[1-bromo-7-(trifluoromethyl)imidazo[1,2-a]quinoxalin-4-yl]amino}propan-1-ol

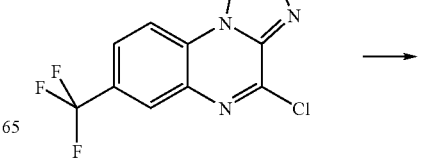

-continued

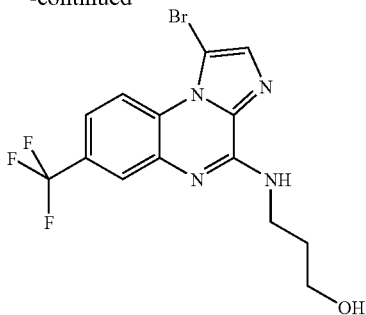

To a solution of compound 1-bromo-4-chloro-7-(trifluoromethyl)imidazo[1,2-a]quinoxaline (1.00 g; 2.85 mmol; 1 eq) in anhydrous dioxane (124 mL) 1-aminopropanol (2.4 mL; 31.4 mmol; 11 eq) is added under argon atmosphere. The solution is allowed to stir for 17 hours under reflux until the reaction is complete on TLC. The crude mixture is cooled to room temperature, diluted with ethyl acetate (250 mL) and washed four times with a saturated solution of sodium hydrogenocarbonate (4×200 mL). The recombined aqueous phases are extracted one more time with ethyl acetate (500 mL). The combined organic phases are dried over sodium sulfate, filtered and concentrated under vacuum to afford a beige powder. This powder is washed wish ether, and after filtration, the title compound is isolated pure (1.05 g; 2.69 mmol; 94%).

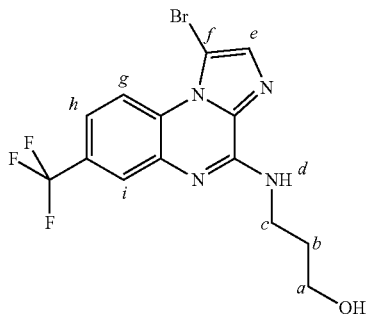 [SMILES: OCCCNc1nc2cc(C(F)(F)F)ccc2n2c(Br)cnc12]

$^1$H NMR (DMSO-d$_6$), δ (ppm): 9.08 (d, J=8.8 Hz, 1H, g), 8.07 (t, J=6.3 Hz, 1H, d), 7.84 (s, 1H, i), 7.77 (s, 1H, e), 7.63 (d, J=8.8 Hz, 1H, h), 4.62 (t, J=5.4 Hz, 1H, —OH), 3.61 (q, J=6.3 Hz, 2H, c), 3.53 (q, J=6.3 Hz, 2H, a), 1.82 (qt, J=6.3 Hz, 2H, b) as determined by HSQC and NOESY.

No NOE correlation is observed between g and e $^{13}$C-APT NMR (DMSO-d$_6$), δ (ppm): 147.4, 137.8, 134.3, 133.8, 127.5, 126.6 (q, J=32 Hz), 123.9 (q, J=270 Hz), 123.0, 117.6, 115.4, 99.5, 58.9, 37.6, 31.7

Example 3

3-{[1-iodo-7-(trifluoromethyl)imidazo[1,2-a]quinoxalin-4-yl]amino}propan-1-ol

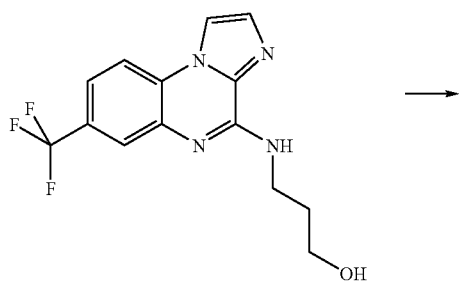

-continued

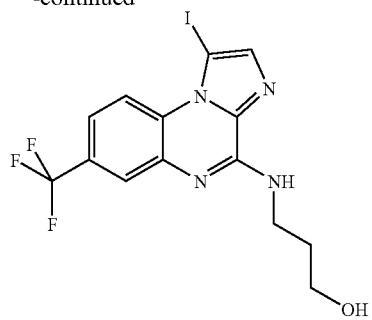

To a 10-min stirred mixture of iodine (245 mg, 0.966 mmol, 0.6 eq) with Selectfluor™ (399 mg, 1.13 mmol, 0.7 eq) in acetonitrile (10 mL) under argon is added the 3-{[7-(trifluoromethyl)imidazo[1,2-a]quinoxalin-4-yl]amino}propan-1-ol (500 mg, 1.61 mmol, 1 eq). The dark red mixture is stirred at rt for 24 h. The precipitate is filtered out, washed with acetonitrile and dissolved in 150 mL of EtOAc. This organic phase is washed with a saturated solution of ammonium chloride, a saturated solution of sodium hydrogenocarbonate, a saturated solution of sodium hydrogen sulfite, then dried over magnesium sulfate and concentrated. A first batch of desired product is obtained as a white solid (135 mg, 0.31 mmol). To the remaining red liquor is added 0.7 additional equivalent of Selectfluor™ and 0.6 additional equivalent of iodine and the mixture is stirred under argon at rt for 16 h. Similar work-up allows the collection of a second batch (298 mg, 0.68 mmol, overall yield 62%).

$^1$H NMR (DMSO-d$_6$), δ (ppm): 9.34 (d, J=8.3 Hz, 1H), 8.00 (t, J=4.8 Hz, 1H), 7.85 (s, 1H), 7.75 (s, 1H), 7.69 (d, J=8.1 Hz, 1H), 4.60 (t, J=5.3 Hz, 1H), 3.61 (q, J=6.8 Hz, 2H), 3.53 (q, J=5.8 Hz, 2H), 1.82 (qt, J=6.6 Hz, 2H)

ESI-MS m/z 437 (M+H)$^+$

Example 4

3-(7-bromo-imidazo[1,2-a]quinoxalin-4-ylamino)-propan-1-ol

Step 1: Synthesis of
1-(4-bromo-2-nitro-phenyl)-1H-imidazole

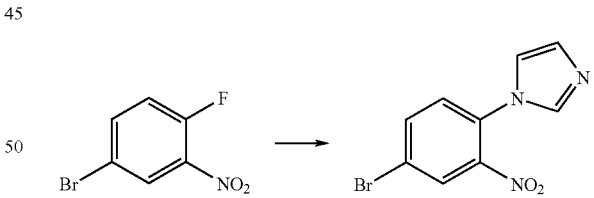

To a solution of 4-bromo-1-fluoro-2-nitrobenzene (1.12 mL; 9.09 mmol; 1 eq) and diisopropylethylamine (1.58 mL; 9.09 mmol; 1 eq;) in anhydrous acetonitrile (80 mL) is added imidazole (620 mg; 9.09 mmol; 1 eq) under argon. The reaction mixture is allowed to stir under reflux for 65 hours until complete consumption of starting material. The crude mixture is concentrated under vacuum and the resulting powder dissolved in ethyl acetate (60 mL). The organic phase is then washed with water (50 mL), brine (50 mL) and dried over sodium sulfate to provide an orange powder after concentration under vacuum. Further purification by flash chromatography on silica gel (ethyl acetate/cyclohexane 9:1) afforded the title compound (1.81 g; 6.7 mmol; 74%) as an orange powder.

¹H NMR (CDCl₃), δ (ppm): 8.16 (d, J=2.4 Hz, 1H), 7.87 (dd, J=8.3 and 2.4 Hz, 1H), 7.65 (d, J=2.4 Hz, 1H), 7.37 (d, J=8.3 Hz, 1H), 7.25 (d, J=8.3 Hz, 1H), 7.06 (d, J=2.4 Hz, 1H)

Step 2: Synthesis of
5-Bromo-2-imidazol-1-yl-phenylamine

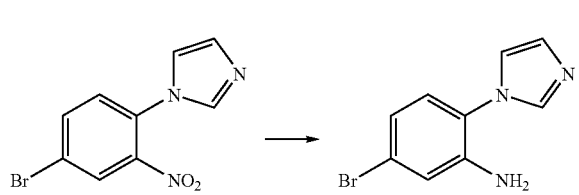 [SMILES: O=[N+]([O-])c1cc(Br)ccc1-n1ccnc1 ; Nc1cc(Br)ccc1-n1ccnc1]

To a solution of 1-(4-bromo-2-nitro-phenyl)-1H-imidazole (1.80 g; 6.72 mmol; 1 eq) in ethanol (90 mL) is added dehydrated tin chloride (7.58 g; 33.58 mmol; 5 eq). The reaction mixture is allowed to stir under reflux for 20 hours until completion of the reaction. The crude reaction mixture is then concentrated under vacuum. The resulting mixture is dissolved in water/ethyl acetate 1:2 (40 mL). The aqueous phase is basified until pH 9 is reached with solid hydrogen carbonate. The milky white aqueous phase is then extracted twice with ethyl acetate (2×100 mL). The combined organic phases are washed with brine (100 mL), dried over sodium sulfate and concentrated under vacuum to provide a beige powder. Purification by chromatography on silica gel (dichloromethane/methanol 97:3), afforded the title compound (1.47 g; 6.2 mmol; 92%) as a yellow powder.

¹H NMR (DMSO-d₆), δ (ppm): 7.74 (d, J=1 Hz, 1H), 7.29 (br s, 1H), 7.10-6.96 (m, 3H), 6.75 (dd, J=7.8 and 2 Hz, 1H), 5.27 (br s, 2H)

Step 3: Synthesis of
7-Bromo-5H-imidazo[1,2-a]quinoxalin-4-one

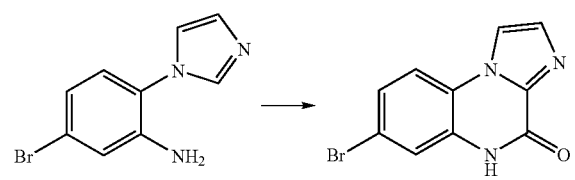 [SMILES: Nc1cc(Br)ccc1-n1ccnc1 ; O=c1[nH]c2cc(Br)ccc2n2ccnc12]

To a solution of 5-bromo-2-imidazol-1-yl-phenylamine (5.00 g; 21 mmol; 1 eq) in anhydrous dichlorobenzene (410 mL), is added carbonyldiimidazole (6.94 g; 42 mmol; 2 eq) under argon atmosphere. This reaction mixture is allowed to stir under reflux for 2 hours. The initial crystal clear solution quickly turns black after heating and become non homogeneous. This crude reaction mixture is allowed to cool to room temperature and the grey powder formed during the reaction is filtered off on a fritted glass. The filtrate is cooled down to 0° C. overnight to afford a second batch of grey powder. The combined 6.5 g of grey solid is transferred in a 1 L flask, diluted in fresh ethyl acetate (500 mL) and heated to gentle reflux for ten minutes. Hot filtration followed by concentration afforded the title compound as a grey powder (3.85 g; 14.6 mmol; 69%).

¹H NMR (DMSO-d₆), δ (ppm): 11.90 (s, 1H), 8.53 (s, 1H), 8.16 (d, J=8.8 Hz, 1H), 7.60 (s, 1H), 7.48 (m, 2H)

Step 4: Synthesis of
7-Bromo-4-chloro-imidazo[1,2-a]quinoxaline

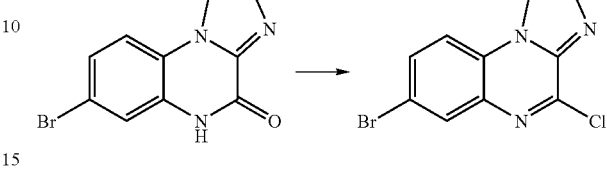

To a suspension of 7-bromo-5H-imidazo[1,2-a]quinoxalin-4-one (800 mg; 3.0 mmol; 1 eq) in phosphorus oxychloride (15 mL) is added under argon dimethylaniline (1.7 mL). The reaction mixture is allowed to stir for 1 h30 under reflux. The reaction mixture becomes homogeneous but turns black. The phosphorus oxychloride is evaporated under argon and the viscous residue is diluted in ethyl acetate (2×25 mL) and concentrated under vacuum. This operation is repeated twice until a grey powder is obtained. This powder is then dissolved in hot ethyl acetate (25 mL), washed with brine (50 mL), dried over sodium sulfate and concentrated under vacuum to provide a yellowish powder (980 mg). Further purification by flash chromatography on silica gel (cyclohexane/methylene chloride/ethyl acetate 20:95:5 afforded the title compound (850 mg; 3.0 mmol; 99%) still contaminated by 10% of 7-bromo-4-chloroimidazo[1,5-a]quinoxaline as seen in ¹H NMR. The beige powder obtained is engaged in the next step without any further purification.

¹H NMR (DMSO-d₆), δ (ppm): 8.96 (s, 1H), 8.42 (d, J=8.8 Hz, 1H), 8.37 (d, J=2.4 Hz, 1H), 7.98 (dd, J=2.4 and 8.8 Hz, 1H), 7.90 (d, J=1.5 Hz, 1H)

Step 5: Synthesis of 3-(7-Bromo-imidazo[1,2-a]quinoxalin-4-ylamino)-propan-1-ol

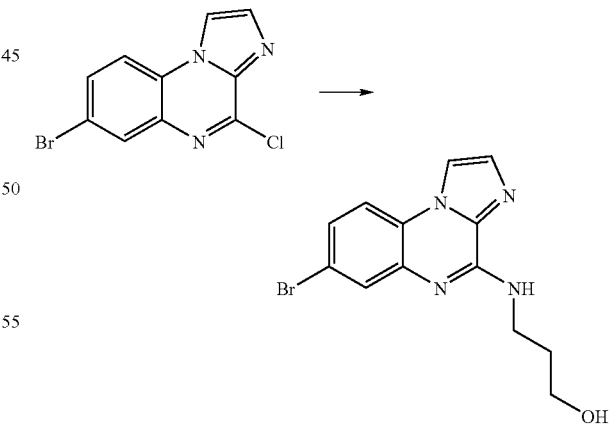

To a solution of 7-bromo-4-chloro-imidazo[1,2-a]quinoxaline (2.75 g; 9.6 mmol; 1 eq) in anhydrous dioxane (421 mL), 3-aminopropanol (1.83 mL; 24.1 mmol; 2.5 eq) is added under argon atmosphere. After 17 hours of stirring under reflux, the reaction mixture is cooled to room temperature and diluted in ethyl acetate (250 mL). The organic phase is washed three times with a molar solution of sodium hydroxide (3×150 mL). The recombined water phases are extracted one more time with ethyl acetate (300 mL) and the combined organic phases dried over sodium sulfate and concentrated under vacuum. The resulting beige powder is further washed with ether (200 mL) to provide the title compound (2.70 g; 8.4 mmol; 89%) as a grey powder.

$^1$H NMR (DMSO-$d_6$), δ (ppm): 8.58 (d, J=1 Hz, 1H), 8.04 (d, J=4.3 Hz, 1H), 7.90 (t, J=5.5 Hz, 1H), 7.68 (dd, J=8.5 and 2 Hz, 1H), 7.61 (d, J=2.0 Hz, 1H), 7.40 (dd, J=4.2 and 1 Hz, 1H), 4.65 (s, 1H), 3.61 (t, J=3.5 Hz, 2H), 3.54 (t, J=3.3 Hz, 2H), 1.81 (qt, J=3.3 Hz, 2H)

$^{13}$C-APT NMR (DMSO-$d_6$): 147.8, 138.4, 132.2, 131.9, 127.7, 124.7, 123.4, 118.3, 117.2, 114.9, 58.8, 37.5, 31.8

APPI-MS m/z 322 (M+H)$^+$

Example 5

3-({7-[2-(trifluoromethyl)phenyl]imidazo[1,2-a]quinoxalin-4-yl}amino)propan-1-ol

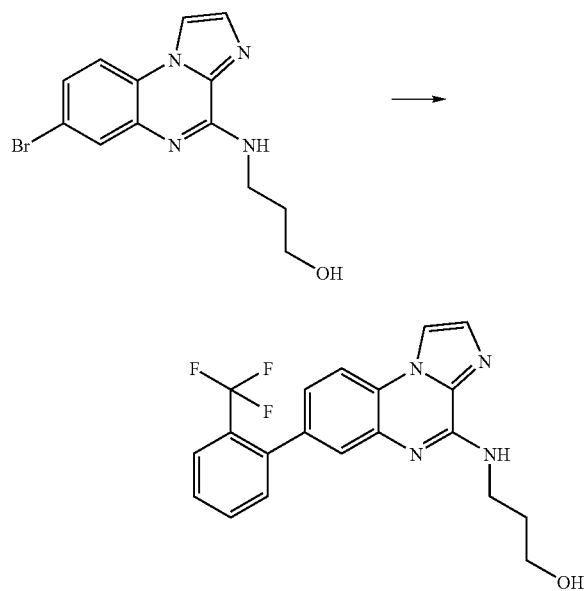 [SMILES: OCCCNc1nc2cc(Br)ccc2n2ccnc12 ; OCCCNc1nc2cc(-c3ccccc3C(F)(F)F)ccc2n2ccnc12]

Tetrakis(triphenylphosphine)palladium (11 mg, 0.009 mmol, 0.1 eq), 3-(7-Bromo-imidazo[1,2-a]quinoxalin-4-ylamino)-propan-1-ol (30 mg, 0.093 mmol, 1 eq), 2-(trifluoromethyl)phenylboronic acid (19 mg, 0.102 mmol, 1.1 eq), potassium carbonate (51 mg, 0.372 mmol, 4 eq) are stirred under argon in a mixture of degassed water/1,2-dimethoxyethane (1 mL/1 mL) at 80° C. for 3 days. Evaporation of 1,2-dimethoxyethane, partition (water/ethyl acetate), extraction of the aqueous phase (two times ethyl acetate), reunion of the organic phases, drying over magnesium sulfate and purification over silicagel on prep TLC (eluent: dichloromethane/methanol 90:10) affords the title compound as an off-white solid (14 mg, 0.036 mmol, 39%).

$^1$H NMR (CD$_3$OD), δ (ppm): 8.46 (s, 1H), 8.06 (d, J=8.4 Hz, 1H), 7.88 (d, J=7.8 Hz, 1H), 7.69-7.62 (m, 4H), 7.51 (d, J=7.6 Hz, 1H), 7.34 (d, J=8.3 Hz, 1H), 3.84 (t, J=6.7 Hz, 2H), 3.78 (t, J=6.1 Hz, 2H), 2.02 (qt, J=6.4 Hz, 2H)

ESI-MS m/z 387 (M+H)$^+$

Example 6

3-{[(7-(ethylthio)imidazo[1,2-a]quinoxalin-4-yl]amino}propan-1-ol

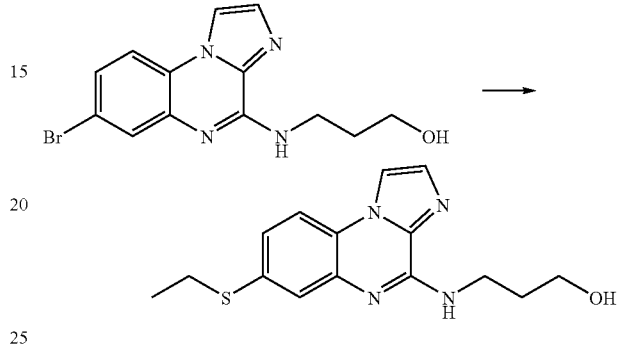

To a solution of sodium ethanethiolate (98 mg, 1.17 mmol, 1.5 eq) in anhydrous butanol (3 mL), 3-[(7-Bromo-imidazo[1,2-a]quinoxalin-4-yl)amino]propan-1-ol (250 mg, 0.78 mmol, 1 eq) is added under argon followed by tetrakis(triphenylphosphine)palladium(0) (27 mg, 0.02 mmol, 0.03 eq).

The reaction mixture is allowed to stir overnight at 120° C. Sodium ethanethiolate (59 mg, 0.70 mmol, 0.9 eq) and tetrakis(triphenylphosphine)palladium(0) (45 mg, 0.04 mmol, 0.05 eq) are added and the reaction mixture is allowed to stir at 120° C. for 3 days. The crude mixture is a black solution. Evaporation of butanol, partition (water/ethyl acetate), extraction of the aqueous phase (three times ethyl acetate), reunion of the organic phases, drying over magnesium sulfate provided a solid after concentration under vacuum. Trituration in ethyl acetate followed by drying affords the title compound as a white powder (45 mg, 0.15 mmol, 19%)

$^1$H NMR (DMSO-$d_6$), δ (ppm): 8.56 (d, J=1.2 Hz, 1H), 8.04 (d, J=8.5 Hz, 1H), 7.77 (t, J=5.5 Hz, 1H), 7.60 (d, J=1.2 Hz, 1H), 7.48 (d, J=2.0 Hz, 1H), 7.22 (dd, J=8.5 and 2 Hz, 1H), 4.65 (t, J=5.3 Hz, 1H), 3.61 (q, J=6.4 Hz, 2H), 3.53 (q, J=5.9 Hz, 2H), 3.05 (q, J=7.3 Hz, 2H), 1.82 (qt, J=6.5 Hz, 2H), 1.27 (t, J=7.3 Hz, 3H)

ESI-MS m/z 303 (M+H)$^+$

Example 7

3-{[7-(trifluoromethoxy)imidazo[1,2-a]quinoxalin-4-yl]amino}propan-1-ol

Step 1: Synthesis of 1-[2-nitro-4-(trifluoromethoxy)phenyl]-1H-imidazole

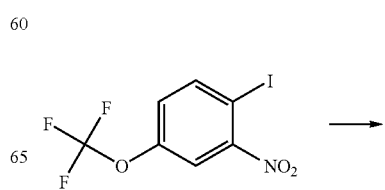

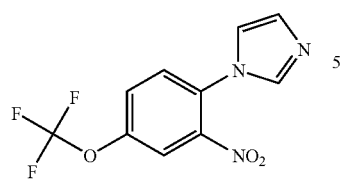

1H-imidazole (818 mg, 12 mmol, 4 eq) and 1-iodo-2-nitro-4-(trifloromethoxy)benzene (1.0 g, 3 mmol, 1 eq) under argon are heated with a heat-gun at between 300 and 500° C. for 45 min until 1-iodo-2-nitro-4-(trifluoromethoxy)benzene has completely reacted on TLC monitoring. The crude mixture is cooled to room temperature, diluted in ethyl acetate and washed with a saturated solution of ammonium chloride. The organic phase is dried over sodium sulfate and concentrated under vacuum. Purification on silica gel (95/05 dichloromethane/methanol) afforded the title compound (570 mg, 2.08 mmol, 69%) as a yellow powder.

1[1]H NMR (DMSO-$d_6$), δ (ppm): 8.32 (d, J=2.2 Hz, 1H), 7.97 (dd, J=8.6 and 2.0 Hz, 1H), 7.96 (s, 1H), 7.88 (d, J=8.6 Hz, 1H), 7.47 (br s, 1H), 7.11 (br s, 1H)

ESI-MS m/z 274 (M+H)$^+$

Step 2: Synthesis of 2-(1H-imidazol-1-yl)-5-(trifluoromethoxy)aniline

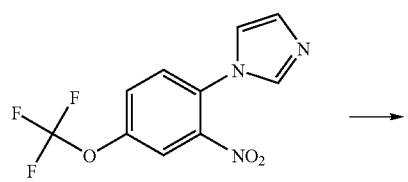

1-[2-nitro-4-(trifluoromethoxy)phenyl]-1H-imidazole (1.68 g, 6.15 mmol, 1 eq) was reduced to the corresponding aniline according to example 1 step 2.

Purification on silica gel (95/05 dichloromethane/methanol) afforded the title compound (1.09 g, 4.48 mmol, 73%) as a beige powder.

$^1$H NMR (DMSO-$d_6$), δ (ppm): 7.77 (t, J=1 Hz, 1H), 7.32 (t, J=1.2 Hz, 1H), 7.15 (d, J=8.5 Hz, 1H), 7.11 (t, J=1 Hz, 1H), 6.81 (q, J=1 Hz, 1H), 6.56 (dq, J=8.5 and 1 Hz, 1H), 5.40 (br s, 2H)

ESI-MS m/z 244 (M+H)$^+$

Step 3: Synthesis of 7-(trifluoromethoxy)imidazo[1,2-a]quinoxalin-4(5H)-one

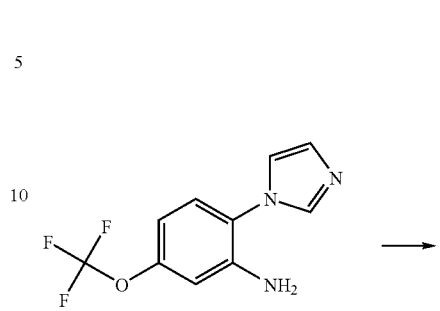

2-(1H-imidazol-1-yl)-5-(trifluoromethoxy)aniline (300 mg, 1.23 mmol, 1 eq) was cyclized according to example 1 step 3. Without further purification the title compound (205 mg, 0.76 mmol, 62%) was recovered as a grey powder.

$^1$H NMR (DMSO-$d_6$), δ (ppm): 8.57 (s, 1H), 8.25 (d, J=8.5 Hz, 1H), 7.62 (s, 1H), 7.34 (s, 1H), 7.33 (d, J=8.5 Hz, 1H)

ESI-MS m/z 270 (M+H)$^+$

Step 4: Synthesis of 4-chloro-7-(trifluoromethoxy)imidazo[1,2-a]quinoxaline

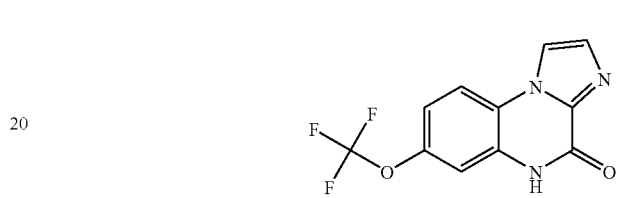

7-(trifluoromethoxy)imidazo[1,2-a]quinoxalin-4(5H)-one (205 mg, 0.76 mmol, 1 eq) was chlorinated according to example 1 step 4. Purification on silica gel (95/05 dichloromethane/methanol) afforded the title compound (134.5 mg, 0.47 mmol, 61%) as a grey powder.

$^1$H NMR (DMSO-$d_6$), δ (ppm): 9.02 (d, J=1.2 Hz, 1H), 8.57 (d, J=9.0 Hz, 1H), 8.06 (d, J=1.7 Hz, 1H), 7.94 (d, J=1.2 Hz, 1H), 7.88 (dd, J=9.0 and 1.7 Hz, 1H)

ESI-MS m/z 288 (M+H)$^+$

Step 5: Synthesis of 3-{[7-(trifluoromethoxy)imidazo[1,2-a]quinoxalin-4-yl]amino}propan-1-ol

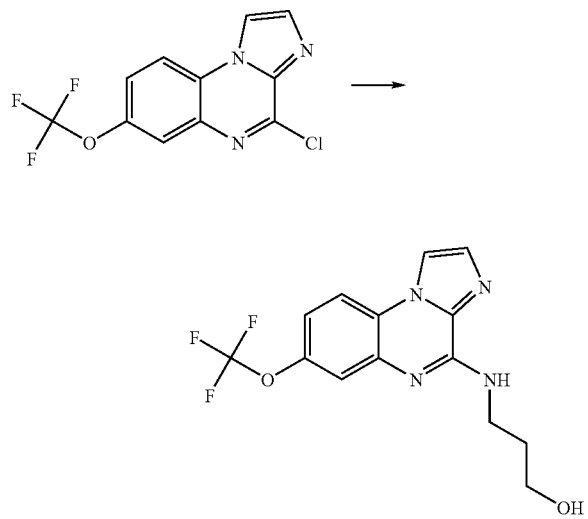

4-chloro-7-(trifluoromethoxy)imidazo[1,2-a]quinoxaline (132.5 mg, 0.46 mmol, 1 eq) was substituted according to example 1 step 5. The crude beige powder is further washed with dichloromethane to provide the title compound (113.7 mg, 0.35 mmol, 76%) as a white powder.

$^1$H NMR (DMSO-$d_6$), δ (ppm): 8.63 (d, J=1.2 Hz, 1H), 8.22 (d, J=8.8 Hz, 1H), 7.99 (t, J=5.6 Hz, 1H), 7.64 (d, J=1.2 Hz, 1H), 7.46 (d, J=2.2 Hz, 1H), 7.29 (d, J=8.8 and 2.2 Hz, 1H), 4.62 (t, J=5.3 Hz, 1H), 3.62 (q, J=6.3 Hz, 2H), 3.53 (m, J=5.9 Hz, 2H), 1.82 (qt, J=6.5 Hz, 2H)

ESI-MS m/z 327 (M+H)$^+$

Example 8

N-{3-[4-(3-Hydroxy-propylamino)-7-trifluoromethyl-imidazo[1,2-a]quinoxalin-1-yl]-phenyl}-acetamide

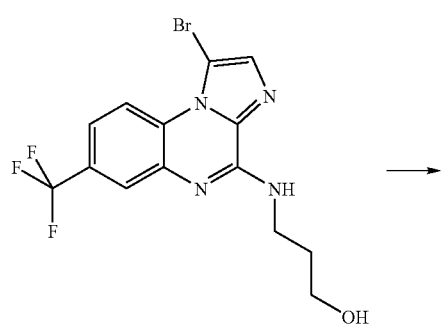

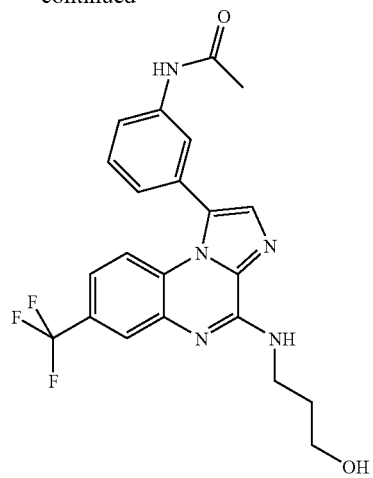

To a solution of 3-(1-Bromo-7-trifluoromethyl-imidazo[1,2-a]quinoxalin-4-ylamino)-propan-1-ol (375 mg; 0.96 mmol; 1 eq) in a mixture of 1,2-dimethoxyethane and water (3.4 mL/1.4 mL), 3-acetamidophenylboronic acid (242 mg, 1.35 mmol; 1.4 eq) is added under argon followed by potassium carbonate (266 mg; 1.93 mmol; 2 eq) and tetrakis(triphenylphosphine)palladium (89 mg; 0.08 mmol; 0.08 eq). The solution is allowed to stir for 17 hours at 90° C. until the reaction is complete on TLC. The crude mixture is cooled to room temperature, diluted with ethyl acetate (15 mL) and washed with water (10 mL). The resulting organic phase is dried over sodium sulfate, filtered and concentrated under vacuum to afford a grey powder. This solid is passed through two successive columns (eluent column 1: ethyl acetate 100%; eluent column 2: methylene chloride/methanol 9:1) to afford the title compound as an off-white powder (256 mg; 0.58 mmol; 60%).

$^1$H NMR (DMSO-$d_6$), δ (ppm): 10.18 (s, 1H), 8.08 (t, J=5.4 Hz, 1H), 7.82 (s, 1H), 7.80 (d, J=7.8 Hz, 2H), 7.57 (s, 1H), 7.55-7.24 (m, 4H), 4.65 (t, J=5.4 Hz, 1H), 3.65 (q, J=6.3 Hz, 2H), 3.55 (q, J=6.3 Hz, 2H), 2.06 (s, 3H), 1.85 (qt, J=6.3 Hz, 2H)

APPI-MS m/z 443.7 (M+H)$^+$

Example 9

3-{4-[(3-hydroxypropyl)amino]-7-(trifluoromethyl)imidazo[1,2-a]quinoxalin-1-yl}benzenesulfonamide

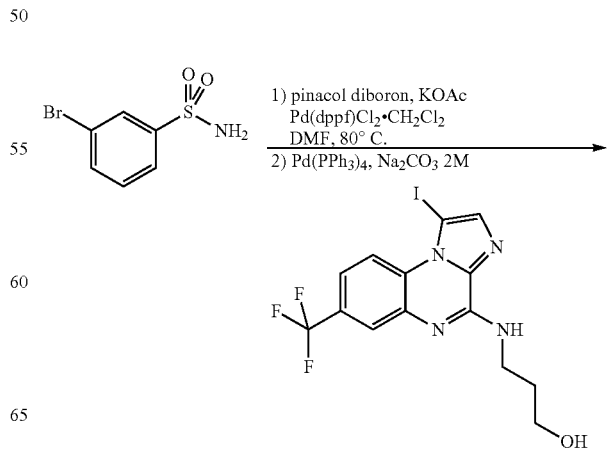

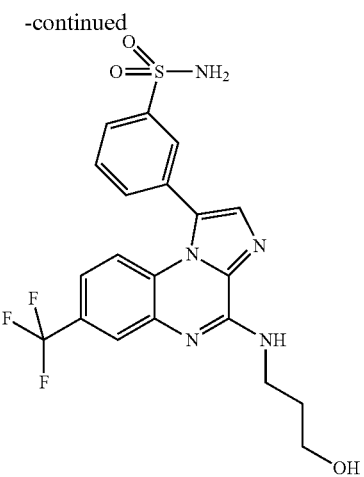

A suspension of 3-bromobenzenesulfonamide (50 mg, 0.21 mmol), bis(pinacolato)diboron (54 mg, 0.21 mmol), potassium acetate (78 mg, 0.80 mmol) and Pd(dppf)Cl$_2$.DCM (9 mg, 0.0105 mmol) in anhydrous dimethylformamide (1 mL) was degassed under argon for 10 minutes and then stirred at 80° C. for 2 h. The reaction mixture was allowed to cool to room temperature and 3-{[1-iodo-7-(trifluoromethyl)imidazo[1,2-a]quinoxalin-4-yl]amino}propan-1-ol (46 mg, 0.105 mmol), an aqueous solution of sodium carbonate 2M (367 μL, 0.735 mmol) and Pd(PPh$_3$)$_4$ (5 mg, 0.0042 mmol) was added. The mixture was stirred under argon at 80° C. overnight and then cooled to room temperature, diluted with cold water and extracted four times with ethyl acetate. The combined organic layers were dried over sodium sulfate, filtered and evaporated. The crude product was purified by preparative TLC (silica gel, dichloromethane/methanol 90/10) to afford 3-{4-[(3-hydroxypropyl)amino]-7-(trifluoromethyl)imidazo[1,2-a]quinoxalin-1-yl}benzenesulfonamide (14 mg, 28%) as a white solid.

$^1$H NMR (DMSO-d$_6$), δ (ppm): 8.11 (t, J=6.1 Hz, 1H), 8.06 (t, J=1.5 Hz, 1H), 8.03 (d, J=7.8 Hz, 1H), 7.88 (d, J=7.8 Hz, 1H), 7.85 (br s, 1H), 7.80 (t, J=7.8 Hz, 1H), 7.66 (s, 1H), 7.50 (bs, 2H), 7.30-7.35 (m, 2H), 4.63 (t, J=5.3 Hz, 1H), 3.67 (q, J=6.1 Hz, 2H), 3.56 (q, J=6.0 Hz, 2H), 1.86 (qt, J=6.6 Hz, 2H).

ESI-MS m/z 466 (M+H)$^+$.

General Procedure for Suzuki Couplings

Conditions A (Procedure Using a Previously Prepared Boronic or Boronate Partner, See Example 8)

A suitable Palladium catalyst (1-30 mol %) with its ligands, the halogenated starting material (3-(7-bromo-imidazo[1,2-a]quinoxalin-4-ylamino)-propan-1-ol or 3-(7-iodo-imidazo[1,2-a]quinoxalin-4-ylamino)-propan-1-ol) (1 eq), the boronic or boronate reacting partner (1-3 eq), and a suitable base (usually sodium or potassium carbonate, 1-6 eq) are stirred in a degassed solvent or solvent mixture at 50-120° C. for 2 to 48 h under argon. Concentration, partition (water/ethyl acetate), extraction of the aqueous phase (ethyl acetate), reunion of the organic phases, drying over sodium or magnesium sulfate and purification by flash chromatography or prep TLC over silicagel using a suitable eluent (usually a mixture dichloromethane/methanol or cyclohexane/ethyl acetate or dichloromethane/ethyl acetate or dichloromethane/methanol/ammonia) affords the desired compound.

Conditions B (Procedure Using an In Situ Prepared Boronic or Boronate Partner, See Example 9)

The halogenated substrate (1 eq), bis(pinacolato)diboron (1-2 eq), a suitable base (usually potassium acetate (1-6 eq), a suitable palladium catalyst with its ligands (usually Pd(dppf)Cl$_2$.DCM 1-30 mol %) are stirred in a degassed solvent (usually dimethylformamide) at 60-120° C. for 1-16 h under argon. After cooling down to room temperature, the halogenated tricyclic template (3-(7-bromo-imidazo[1,2-a]quinoxalin-4-ylamino)-propan-1-ol or 3-(7-iodo-imidazo[1,2-a]quinoxalin-4-ylamino)-propan-1-ol) (0.5 eq) is added with base (usually an aqueous solution of sodium or potassium carbonate, 1-6 eq) and a suitable palladium catalyst (usually Pd(PPh$_3$)$_4$ 1-30 mol %). The resulting mixture is stirred under argon at 60-120° C. for 2 to 48 h. Concentration, partition (water/ethyl acetate), extraction of the aqueous phase (ethyl acetate), reunion of the organic phases, drying over sodium or magnesium sulfate and purification by flash chromatography or prep TLC over silicagel using a suitable eluent (usually a mixture dichloromethane/methanol or cyclohexane/ethyl acetate or dichloromethane/ethyl acetate or dichloromethane/methanol/ammonia) affords the desired compound.

The following examples were prepared according to these procedures. The following table provides a summary of the operating conditions.

| Example | Conditions | SM[a] | Catalyst[b] | Solvent[b] | T (° C.) | Time (h) | Yield[c] |
|---|---|---|---|---|---|---|---|
| 10 | A | Br | Pd(PPh$_3$)$_4$ | DME:H$_2$O (6:1) | 105 | 16 | 72 |
| 11 | A | Br | Pd(OAc)$_2$ | acetone:H$_2$O:DMF (5:5:1) | 80 | 12 | 19 |
| 12 | A | Br | PdCl$_2$(dppf)•DCM | DME:H$_2$O (2:1) | 110 | 16 | 46 |
| 13 | A | Br | Pd(OAc)$_2$ | DME:acetone:H$_2$O (1:1:1) | 90 | 48 | 13 |
| 14 | A | Br | Pd(PPh$_3$)$_4$ | DME:H$_2$O (4:1) | 90 | 16 | 79 |
| 15 | A | Br | Pd(PPh$_3$)$_4$ | DME:H$_2$O (1:1) | 80 | 36 | 10 |
| 16 | A | Br | PdCl$_2$(PPh$_3$)$_2$ | Propan-2-ol:H$_2$O (2:1) | 90 | 36 | 80 |
| 17 | A | Br | PdCl$_2$(dppf)•DCM | ACN:H$_2$O (10:3) | 60 | 18 | 11 |
| 18 | A | Br | PdCl$_2$(PPh$_3$)$_2$ | Propan-2-ol:H$_2$O (2:1) | 80 | 36 | 55 |
| 19 | A | Br | Pd(PPh$_3$)$_4$ | DMF | 100 | 3 | 49 |
| 20 | B | Br | PdCl$_2$(dppf)•DCM Pd(PPh$_3$)$_4$ | DMF:H$_2$O (10:3) | 80 | 16 | 9 |
| 21 | A | Br | PdCl$_2$(dppf)•DCM | ACN:H$_2$O (3:1) | 60 | 36 | 41 |

| Example | Conditions | SM[a] | Catalyst[b] | Solvent[b] | T (°C.) | Time (h) | Yield[c] |
|---|---|---|---|---|---|---|---|
| 22 | A | Br | PdCl$_2$(dppf)•DCM | ACN:H$_2$O (3:1) | 60 | 18 | 90 |
| 27 | A | Br | Pd(PPh$_3$)$_4$ | DMF:H$_2$O (2:1) | 90 | 16 | 99[d] |

[a]Starting Material is either Br: 3-(7-bromo-imidazo[1,2-a]quinoxalin-4-ylamino)-propan-1-ol or I: 3-(7-iodo-imidazo[1,2-a]quinoxalin-4-ylamino)-propan-1-ol
[b]dppf: diphenylphosphinoferocene, DCM: dichloromethane, Ac: acetyl, DME: 1,2-dimethoxyethane, DMF: dimethylformamide
[c]isolated yield in % unless otherwise indicated
[d]crude yield in % used as such in the next step

Example 10

3-{[1-(4-methoxyphenyl)-7-(trifluoromethyl)imidazo[1,2-a]quinoxalin-4-yl]amino}propan-1-ol

Example 11

3-{[1-phenyl-7-(trifluoromethyl)imidazo[1,2-a]quinoxalin-4-yl]amino}propan-1-ol

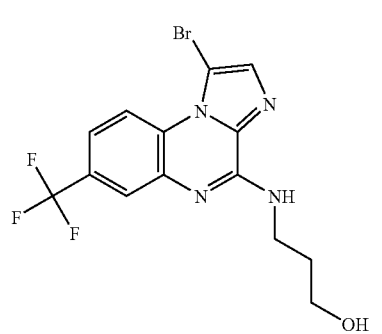

+

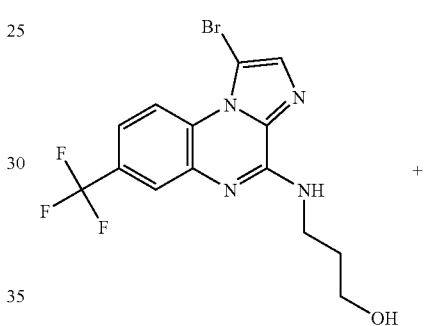

+

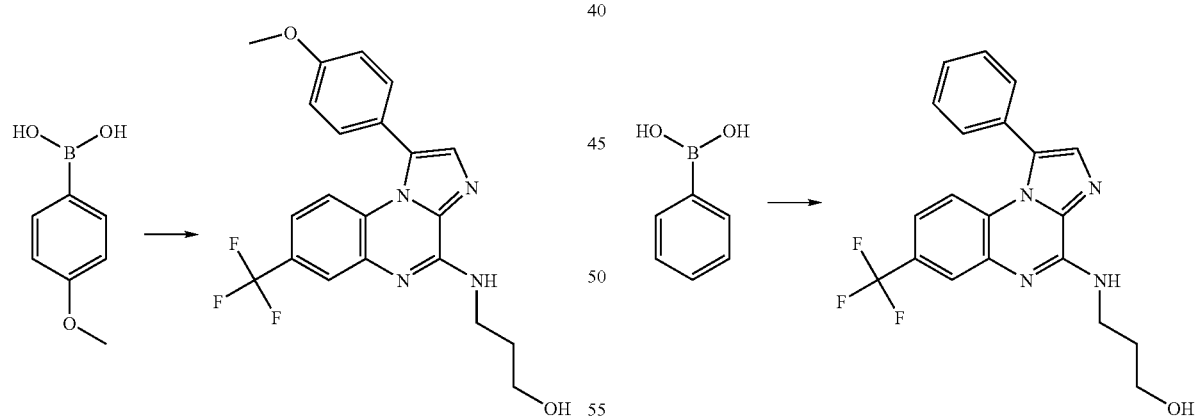

Prepared as mentioned beforehand $^1$H NMR (MeOD), δ (ppm): 7.95 (s, 1H), 7.78-7.64 (m, 3H), 7.52 (d, J=10.2 Hz, 2H), 7.20 (d, J=8.8 Hz, 2H), 3.98 (s, 3H), 3.85 (t, J=6.6 Hz, 2H), 3.80 (t, J=6.1 Hz, 2H), 2.08-2.00 (m, 2H).

ESI-MS m/z 417 (M+H)$^+$

Prepared as mentioned beforehand $^1$H NMR (MeOD), δ (ppm): 7.90 (s, 1H), 7.60-7.58 (m, 5H), 7.50 (s, 1H), 7.41 (d, J=8.7 Hz, 1H), 7.17 (dd, J=8.8 and 1.6 Hz, 1H), 3.81 (t, J=6.7 Hz, 2H), 3.74 (t, J=6.1 Hz, 2H), 2.01-1.97 (m, 2H)

ESI-MS m/z 387 (M+H)+

Example 12

N-{4-[4-(3-Hydroxy-propylamino)-7-trifluoromethyl-imidazo[1,2-a]quinoxalin-1-yl]-phenyl}-methanesulfonamide

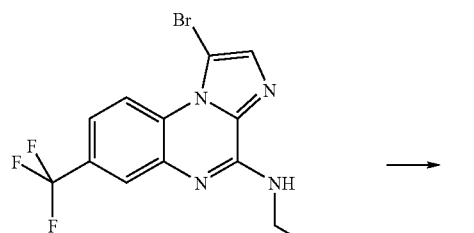

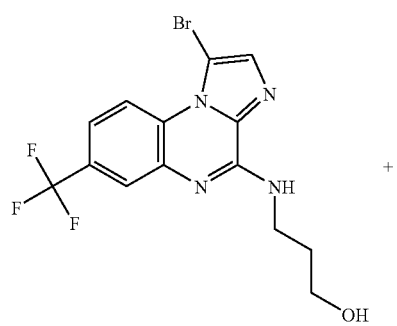

Prepared as mentioned beforehand

¹H NMR (DMSO-d₆), δ (ppm): 8.06 (m, 1H), 7.82 (s, 1H), 7.67-7.35 (m, 8H), 4.63 (s, 1H), 3.80-3.45 (m, 4H), 3.13 (s, 3H), 1.84 (m, 2H)

ESI-MS m/z 480 (M+H)⁺

Example 13

3-{[1-(6-methoxypyridin-3-yl)-7-(trifluoromethyl)imidazo[1,2-a]quinoxalin-4-yl]amino}propan-1-ol

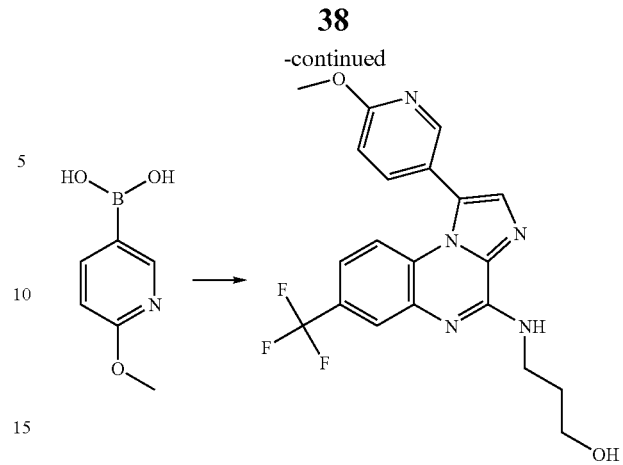

Prepared as mentioned beforehand

¹H NMR (CDCl₃), δ (ppm): 8.34 (d, J=2.3 Hz, 1H), 8.00 (s, 1H), 7.69 (dd, J=8.6 and 2.4 Hz, 1H), 7.48-7.43 (m, 2H), 7.24 (m, 1H), 6.94 (d, J=8.6 Hz, 1H), 4.06 (s, 3H), 3.97-3.93 (m, 2H), 3.73 (t, J=5.5 Hz, 2H), 1.96-1.91 (m, 2H)

ESI-MS m/z 418 (M+H)⁺

Example 14

3-{[1-(4-N-morpholinophenyl)-7-(trifluoromethyl)imidazo[1,2-a]quinoxalin-4-yl]amino}propan-1-ol

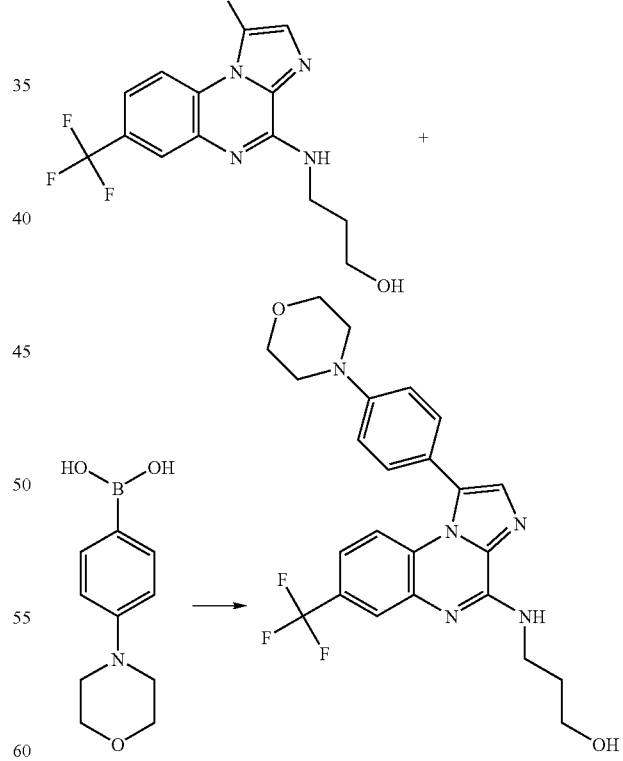

Prepared as mentioned beforehand

¹H NMR (CDCl₃), δ (ppm): 7.92 (s, 1H), 7.50 (d, J=8.7 Hz, 1H), 7.39 (m, 3H), 7.18 (d, J=8.7 Hz, 1H), 7.03 (d, J=8.7 Hz, 2H), 6.70 (br, 1H), 3.94-3.90 (m, 6H), 3.70 (t, J=5.4 Hz, 2H), 3.34-3.27 (m, 4H), 1.92-1.88 (m, 2H)

ESI-MS m/z 472 (M+H)⁺

Example 15

4-{4-[(3-hydroxypropyl)amino]-7-(trifluoromethyl)imidazo[1,2-a]quinoxalin-1-yl}-N-methylbenzamide

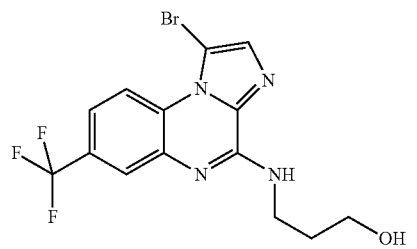

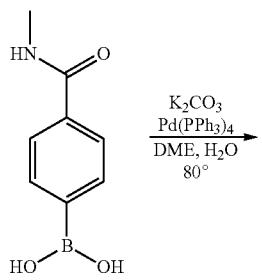

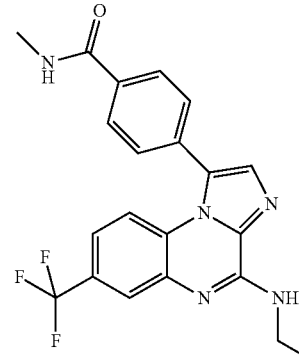

Prepared as mentioned beforehand $^1$H NMR (CD$_3$OD), δ (ppm): 8.02 (d, J=8.2 Hz, 2H), 7.92 (s, 1H), 7.70 (d, J=8.2 Hz, 2H), 7.56 (s, 1H), 7.43 (d, J=8.8 Hz, 1H), 7.21 (dd, J=8.8 and 1.2 Hz, 1H), 3.81 (t, J=6.7 Hz, 2H), 3.75 (t, J=6.1 Hz, 2H), 2.99 (s, 3H), 1.99 (qt, J=6.4 Hz, 2H)

ESI-MS m/z 444 (M+H)$^+$.

Example 16

3-({1-[3-(hydroxymethyl)phenyl]-7-(trifluoromethyl)imidazo[1,2-a]quinoxalin-4-yl}amino)propan-1-ol

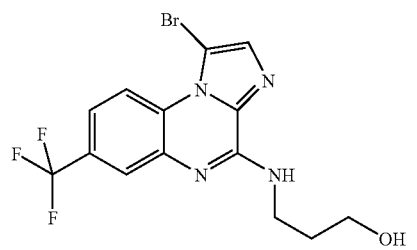

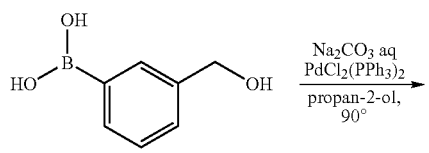

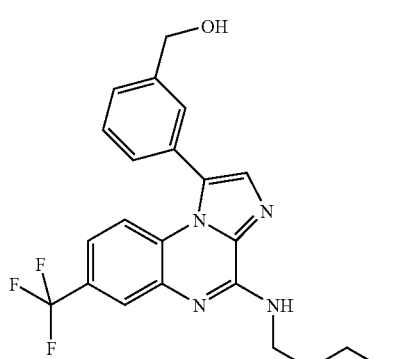

Prepared as mentioned beforehand $^1$H NMR (CD$_3$OD), δ (ppm): 7.84 (s, 1H), 7.62-7.49 (m, 3H), 7.49-7.41 (m, 2H), 7.39 (d, J=8.6 Hz, 1H), 7.12 (d, J=8.6 Hz, 1H), 7.14 (d, J=8.4 Hz, 1H), 4.70 (s, 2H), 3.83-3.66 (m, 4H), 1.97 (qt, J=6.3 Hz, 2H)

ESI-MS m/z 417 (M+H)$^+$

Example 17

3-{[1-(1H-pyrazol-4-yl)-7-(trifluoromethyl)imidazo[1,2-a]quinoxalin-4-yl]amino}propan-1-ol

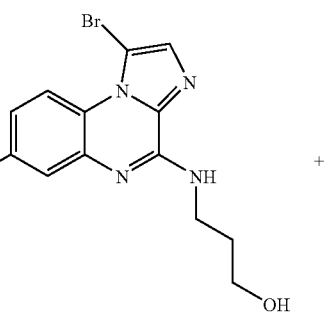

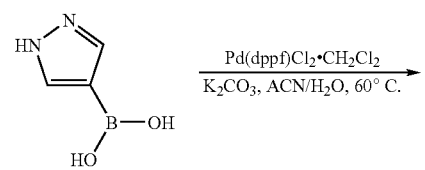

-continued

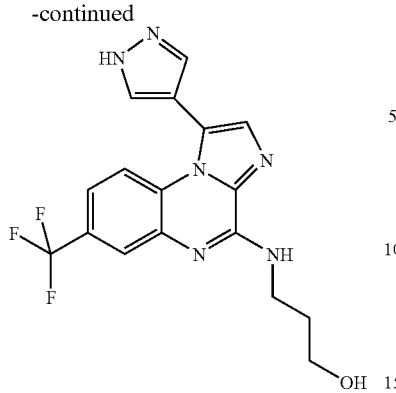

Prepared as mentioned beforehand
$^1$H NMR (CD$_3$OD), δ (ppm): 8.14-7.81 (br s, 2H), 7.90 (d, J=2.0 Hz, 1H), 7.76 (d, J=8.6 Hz, 1H), 7.46 (s, 1H), 7.28 (dd, J=8.8 and 2.0 Hz, 1H), 3.80 (t, J=6.7 Hz, 2H), 3.74 (t, J=6.1 Hz, 2H), 1.98 (qt, J=6.3 Hz, 2H)
ESI-MS m/z 377 (M+H)$^+$ Example 18

3-({1-[4-(aminomethyl)phenyl]-7-(trifluoromethyl)imidazo[1,2-a]quinoxalin-4-yl}amino)propan-1-ol

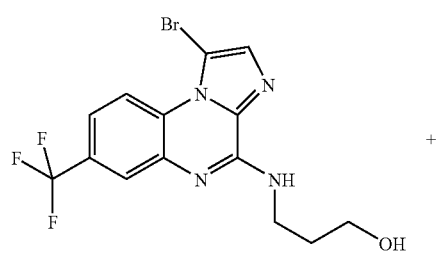

Prepared as mentioned beforehand
$^1$H NMR (CD$_3$OD), δ (ppm): 7.88 (s, 1H), 7.67-7.51 (m, 4H), 7.47 (s, 1H), 7.42 (d, J=8.4 Hz, 1H), 7.14 (d, J=8.4 Hz, 1H), 3.98 (s, 2H), 3.88-3.69 (m, 4H), 2.09-1.91 (m, 2H)
ESI-MS m/z 416 (M+H)$^+$ Example 19

3-{[1-(1H-pyrazol-5-yl)-7-(trifluoromethyl)imidazo[1,2-a]quinoxalin-4-yl]amino}propan-1-ol

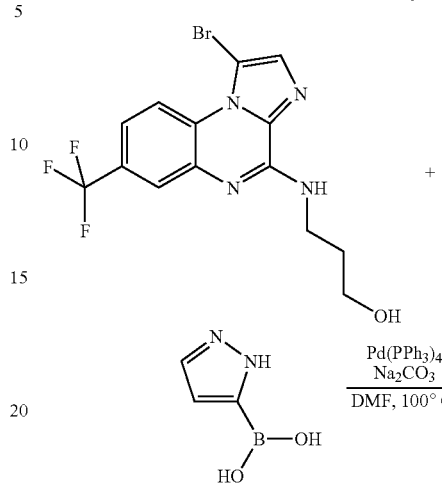

Prepared as mentioned beforehand
$^1$H NMR (DMSO-d$_6$), δ (ppm): 13.46 (s, 1H), 8.05 (br s, 2H), 7.82-7.86 (m, 2H), 7.69 (s, 1H), 7.37 (d, J=8.1 Hz, 1H), 6.68 (d, J=2.1 Hz, 1H), 4.63 (t, J=5.1 Hz, 1H), 3.66 (q, J=6.1 Hz, 2H), 3.56 (q, J=6.1 Hz, 2H), 1.84 (qt, J=6.3 Hz, 2H)
ESI-MS m/z 377 (M+H)$^+$ Example 20

3-{[1-(2-aminopyrimidin-5-yl)-7-(trifluoromethyl)imidazo[1,2-a]quinoxalin-4-yl]amino}propan-1-ol

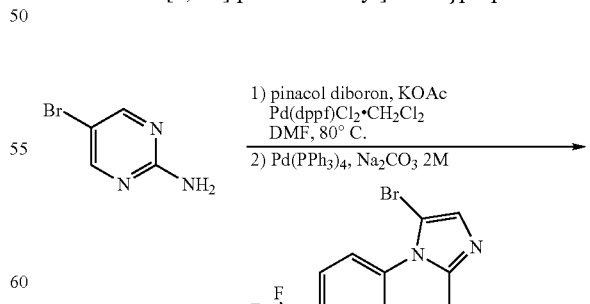

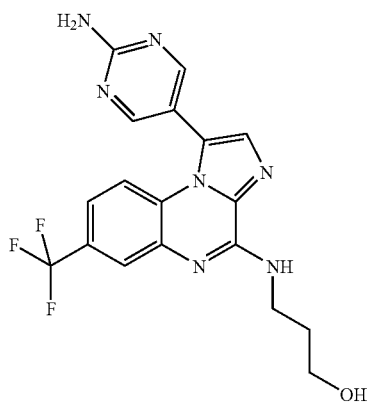

Prepared as mentioned beforehand $^1$H NMR (DMSO-d$_6$), δ (ppm): 8.45 (s, 2H), 8.05 (t, J=5.7 Hz, 1H), 7.82 (s, 1H), 7.66 (d, J=8.6 Hz, 1H), 7.58 (s, 1H), 7.45 (d, J=8.6 Hz, 1H), 7.15 (s, 2H), 4.62 (t, J=5.1 Hz, 1H), 3.65 (q, J=6.3 Hz, 2H), 3.54 (q, J=6.0 Hz, 2H), 1.84 (qt, J=6.6 Hz, 2H)

ESI-MS m/z 404 (M+H)$^+$

Example 21

2-{[1-(4-amino-3-methoxyphenyl)-7-(trifluoromethyl)imidazo[1,2-a]quinoxalin-4-yl]amino}propan-1-ol

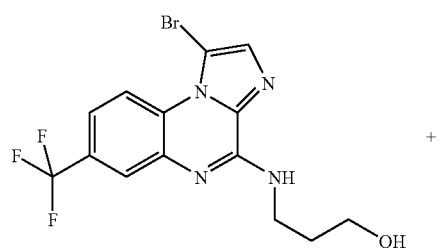

+

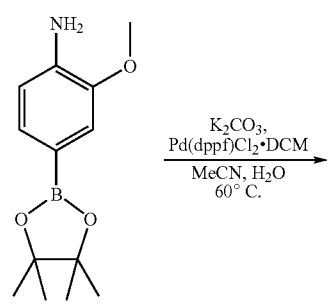

$\xrightarrow{\text{K}_2\text{CO}_3,\ \text{Pd(dppf)Cl}_2\cdot\text{DCM}}_{\text{MeCN, H}_2\text{O, 60° C.}}$

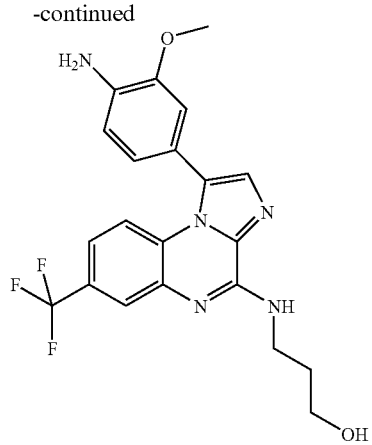

Prepared as mentioned beforehand $^1$H NMR (CD$_3$OD), δ (ppm): 7.85 (d, J=1.3 Hz, 1H), 7.53 (d, J=8.8 Hz, 1H), 7.39 (s, 1H), 7.17 (dd, J=8.8 and 1.7 Hz, 1H), 6.96 (d, J=0.8 Hz, 1H), 6.91-6.87 (m, 2H), 3.82 (s, 3H), 3.78 (t, J=6.7 Hz, 2H), 3.73 (t, J=6.1 Hz, 2H), 1.97 (qt, J=6.3 Hz, 2H).

ESI-MS m/z 432 (M+H)$^+$

Example 22

3-{[7-(trifluoromethyl)-1-vinylimidazo[1,2-a]quinoxalin-4-yl]amino}propan-1-ol

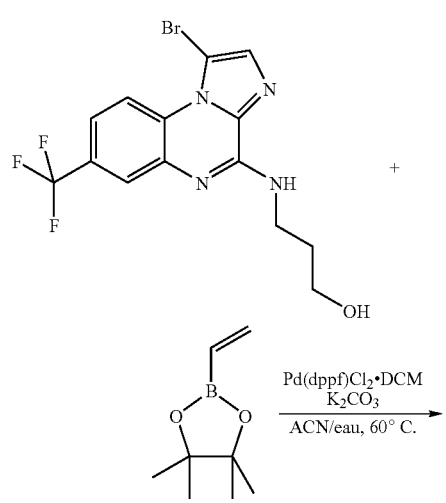

+

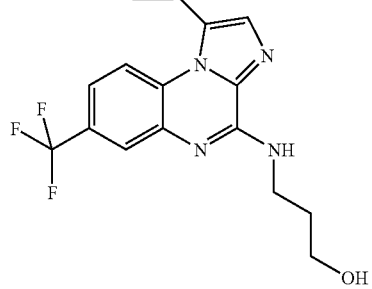

$\xrightarrow{\text{Pd(dppf)Cl}_2\cdot\text{DCM}\ \text{K}_2\text{CO}_3}_{\text{ACN/eau, 60° C.}}$ Prepared as mentioned beforehand $^1$H NMR (CDCl$_3$), δ (ppm): 8.13 (d, J=8.6 Hz, 1H), 7.95 (s, 1H), 7.52 (s, 1H), 7.47 (d, J=8.4 Hz, 1H), 7.13 (dd, J=10.9 and 17.2 Hz, 1H), 6.63 (br s, 1H), 5.85 (d, J=17.2 Hz, 1H), 5.65 (d, J=10.9 Hz, 1H), 3.87 (q, J=5.4 Hz, 2H), 3.67 (t, J=5.1 Hz, 2H), 1.96-1.83 (m, 2H).

ESI-MS m/z 337 (M+H)+

Example 23

N-{4-[4-(3-Hydroxy-propylamino)-7-trifluoromethyl-imidazo[1,2-a]quinoxalin-1-yl]phenyl}-methanesulfonamide Sodium salt

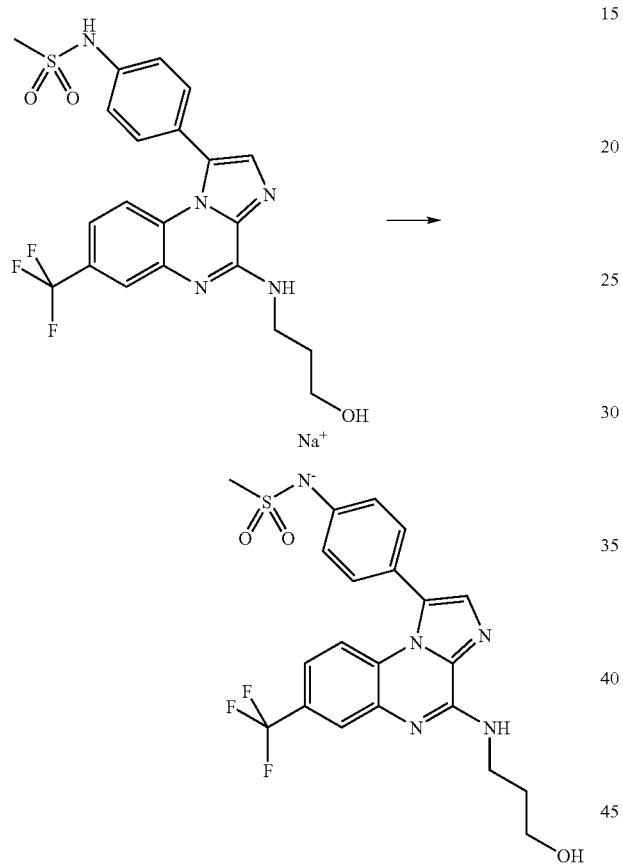

To a solution of the previously obtained N-{4-[4-(3-Hydroxy-propylamino)-7-trifluoromethyl-imidazo[1,2-a]quinoxalin-1-yl]-phenyl}-methanesulfonamide (70 mg; 0.10 mmol; 1 eq) in anhydrous methanol (3.5 mL) is added sodium methoxide (7.9 mg; 0.14 mmol; 1.4 eq). The solution is heated to reflux and allowed to stir overnight. Then, the crude mixture is concentrated in vacuum and the resulting residue is taken up in tetrahydrofuran and filtered to remove the excess of sodium methoxide. The filtrate is concentrated and the resulting solid is purified by trituration in dichloromethane (5×6 mL) to yield the title compound as a white powder (14 mg; 0.027 mmol; 27%).

¹H NMR (DMSO-d₆), δ (ppm): 7.97 (m, 1H), 7.78 (s, 1H), 7.71 (d, J=9.3 Hz, 1H), 7.41 (s, 1H), 7.35 (d, J=9.3 Hz, 1H), 7.33 (d, J=8.8 Hz, 2H), 6.92 (d, J=8.8 Hz, 2H), 4.64 (t, J=5.4 Hz, 1H), 3.63 (m, 2H), 3.54 (m, 2H), 2.61 (s, 3H), 1.80 (qt, J=6.8 Hz, 2H)

ESI-MS m/z 480 (M+H)+

Example 24

3-[1-(4-Methoxy-phenyl)-7-trifluoromethyl-1H-imidazo[4,5-c]quinolin-4-ylamino]-propan-1-ol Step 1: Synthesis of 3-oxo-3-{[3-(trifluoromethyl)phenyl]amino}propanoic acid

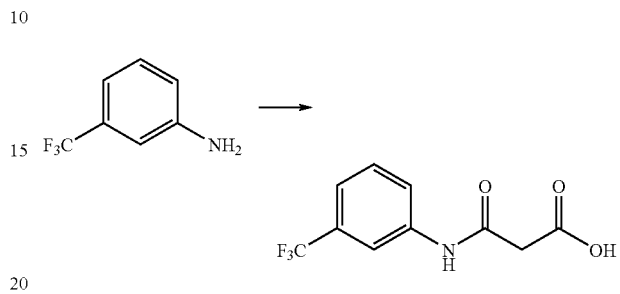

To a solution of 3-trifluoromethyl-phenylamine (11.6 mL; 93 mmol; 1 eq) and triethylamine (12.9 mL; 93 mmol; 1 eq) in dichloromethane (467 mL), methyl malonyl chloride (10.0 mL; 93 mmol; 1 eq.) is added at 0° C., under argon. The solution is allowed to stir for 10 minutes at room temperature. The crude mixture is then treated with water (115 mL) before removing the dichloromethane (15 mL) in vacuum. The resulting aqueous solution is cooled to 0° C. and diluted with methanol (235 mL) before adding dropwise a 1.5 M aqueous solution of LiOH (4.47 g; 186 mmol; 2 eq.). The solution is allowed to stir at room temperature for 1 hour. After removal of methanol under reduced pressure, the pH of the resulting aqueous solution is adjusted to 1 using a concentrated solution of HCl (16 mL). The acidic solution is extracted with dichloromethane (3×300 mL). The combined organic extracts are dried over sodium sulfate, filtered and concentrated under vacuum to afford the title compound as a white powder (21.8 g; 88 mmol; 95%).

¹H NMR (CDCl₃), δ (ppm): 12.54 (broad s, 1H), 10.48 (s, 1H), 8.08 (s, 1H), 7.71 (d, J=8.3 Hz, 1H), 7.56 (t, J=7.8 Hz, 1H), 7.41 (d, J=7.8 Hz, 1H), 3.39 (s, 2H)

Step 2: Synthesis of 4-hydroxy-7-(trifluoromethyl)quinolin-2(1H)-one

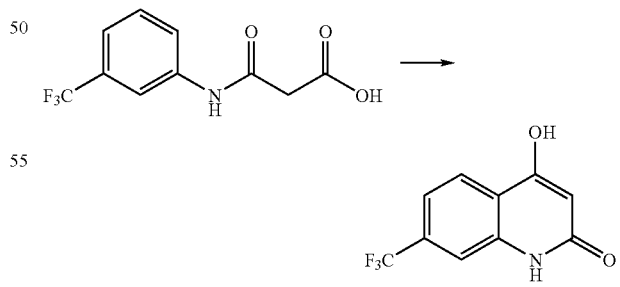

A suspension of 3-oxo-3-{[3-(trifluoromethyl)phenyl]amino}propanoic acid (3.26 g; 13.0 mmol; 1 eq) in polyphosphoric acid (26.4 g) is allowed to stir for 4 hours at 140° C. The mixture becomes limpid after 1 h30 stirring. After cooling to room temperature, the orange solution is taken-up in water (100 mL) and sonicated for 5 minutes. The resulting fine powder is filtrated and washed with cold water (4×20 mL). The solid is taken up several times in ethanol (3×100 mL) and concentrated to afford the title compound as a dry light orange powder (2.19 g; 9.6 mmol; 74%).

$^1$H NMR (DMSO-d$_6$), δ (ppm): 11.57 (broad s, 1H), 7.97 (d, J=8.3 Hz, 1H), 7.58 (s, 1H), 7.44 (d, J=8.0 Hz, 1H), 5.84 (s, 2H)

Step 3: Synthesis of 4-hydroxy-3-nitro-7-(trifluoromethyl)quinolin-2(1H)-one

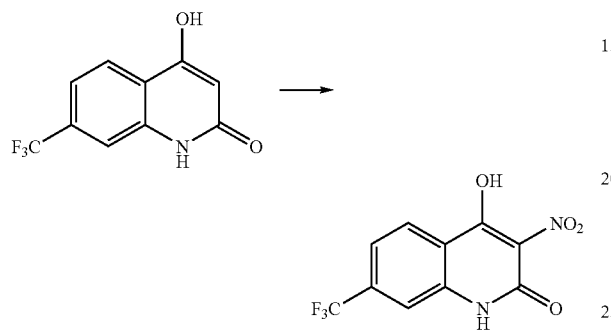

To a solution of 4-hydroxy-7-trifluoromethyl-1H-quinolin-2-one (2.0 g; 8.7 mmol; 1 eq) in acetic acid (10 mL), nitric acid (2.4 mL; 8.6 mmol; 0.99 eq.) is slowly added at 0° C., under argon. The reaction mixture is then heated to 100° C. under stirring and is maintained at this temperature for 1 hour before cooling down to room temperature. The solution is treated with water (39 mL) and the pH of the resulting solution is adjusted to 9 by adding carefully sodium bicarbonate in powder. The basic solution is then extracted with ethyl acetate (540 mL). The organic layers are combined and evaporated under reduced pressure yielding a crude yellowish residue (2.4 g). The solid is purified by trituration in ethyl acetate to afford after filtration the title compound as a yellow powder (1.0 g; 3.6 mmol; 41%).

$^1$H NMR (DMSO-d$_6$), δ (ppm): 10.39 (s, 1H), 8.04 (d, J=8.3 Hz, 1H), 7.37 (s, 1H), 7.25 (d, J=8.3 Hz, 1H)

Step 4: Synthesis of 2,4-dichloro-3-nitro-7-(trifluoromethyl)quinoline

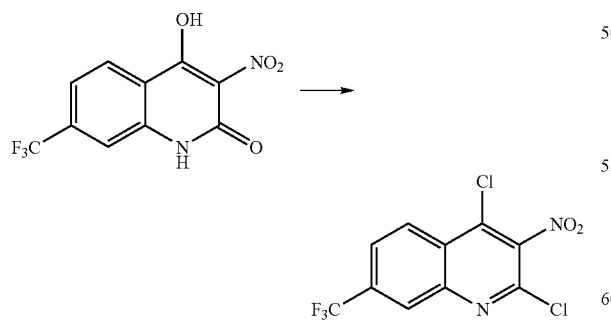

A solution of 4-hydroxy-3-nitro-7-(trifluoromethyl)quinolin-2(1H)-one (100 mg; 364 µmol; 1 eq) in phenylphosphonic dichloride (0.51 mL; 3.64 mmol; 10 eq) is heated to 140° C. for 17 hours. The crude mixture is treated with water (2 mL) and allowed to stir for additional 10 minutes at room temperature. The crude mixture is extracted with ethyl acetate (5×5 mL). The combined extracts are dried over sodium sulfate, filtrated and concentrated under vacuum. The resulting crude solid is purified on silica gel (methylene chloride 100%) to afford the title compound as a white powder (37 mg; 119 µmol; 33%).

$^1$H NMR (CD$_3$OD), δ (ppm): 7.90-7.65 (m, 1H), 7.60-7.40 (m, 2H)

Step 5: Synthesis of 2-chloro-N-(4-methoxyphenyl)-3-nitro-7-(trifluoromethyl)quinolin-4-amine

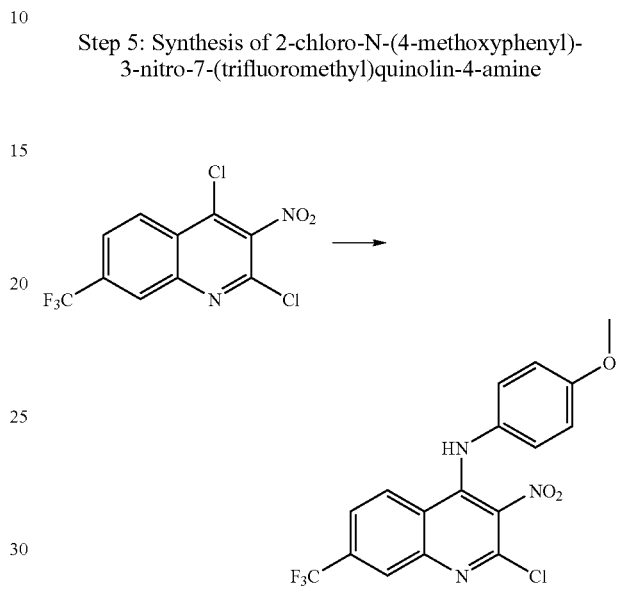

To a solution of 2,4-dichloro-3-nitro-7-trifluoromethyl-quinoline (220 mg; 0.70 mmol; 1 eq) in dimethylformamide (3.5 mL), are added successively triethylamine (105 µL; 0.76 mmol; 1.08 eq) and 4-methoxyaniline (88 mg; 712 mmol; 1.01 eq.). The reaction mixture is allowed to stir for 1 hour at room temperature until the reaction is complete on TLC. The crude solution is diluted with a 1M aqueous solution of HCl (5 mL) and then extracted with ethyl acetate (40 mL). The organic layer is separated and washed 3 times with a 1M aqueous solution of HCl (3×40 mL), dried over sodium sulfate, filtrated and concentrated under vacuum to afford the title compound as a yellow powder (280 mg; 0.70 mmol; 100%) which is used without further purification.

$^1$H NMR (DMSO-d$_6$), δ (ppm): 10.00 (s, 1H), 8.75 (d, J=8.8 Hz, 1H), 8.24 (s, 1H), 8.00 (d, J=8.8 Hz, 1H), 7.15 (d, J=8.8 Hz, 2H), 6.90 (d, J=8.8 Hz, 2H), 3.77 (s, 3H)

Step 6: Synthesis of 2-chloro-N-4-(4-methoxyphenyl)-7-(trifluoromethyl)quinoline-3,4-diamine

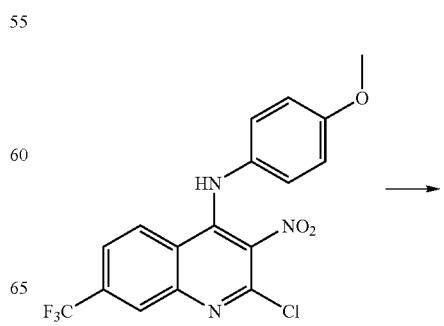

-continued

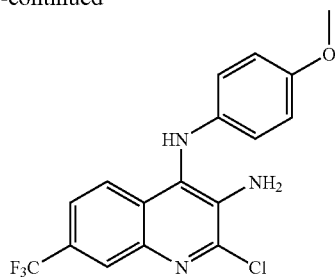

To a black suspension of nickel (II) chloride hexahydrate (83.6 mg; 0.35 mmol; 0.5 eq) and sodium borohydride (13.4 mg; 0.35 mmol; 0.5 eq) in anhydrous methanol (14 mL), a solution of 2-chloro-N-(4-methoxyphenyl)-3-nitro-7-(trifluoromethyl)quinolin-4-amine (280 mg; 0.70 mmol; 1 eq) in anhydrous tetrahydrofuran (2.5 mL) is added at 0° C. Additional sodium borohydride (80 mg; 2.1 mmol; 3 eq) is carefully added in three equal portions. The reaction mixture is then allowed to warm up to room temperature and stirred for 20 minutes at room temperature until the reaction is complete on TLC. Nickel is filtrated and the filtrate is concentrated under vacuum. The resulting black residue is taken up in a 1:1 mixture of ethyl acetate/saturated aqueous NH$_4$Cl solution (200 mL) and filtrated through a plug of Celite®. The organic layer is separated, washed successively with a saturated aqueous NH$_4$Cl solution (100 mL) and with (100 mL), dried over sodium sulfate, filtered and concentrated in vacuum. The resulting green residue is purified on silica gel (cyclohexane/ethyl acetate 8:2) to afford the title compound as a yellow powder (181 mg; 0.49 mmol; 70%).

$^1$H NMR (DMSO-d$_6$), δ (ppm): 8.11 (s, 1H), 7.85 (s, 1H), 6.78 (d, J=8.8 Hz, 1H), 7.63 (d, J=8.8 Hz, 1H), 6.78 (d, J=8.8 Hz, 2H), 6.55 (d, J=8.8 Hz, 2H), 5.62 (br s, 2H), 3.65 (s, 3H)

Step 7: Synthesis of 4-chloro-1-(4-methoxyphenyl)-7-(trifluoromethyl)-1H-imidazo[4,5-c]quinoline

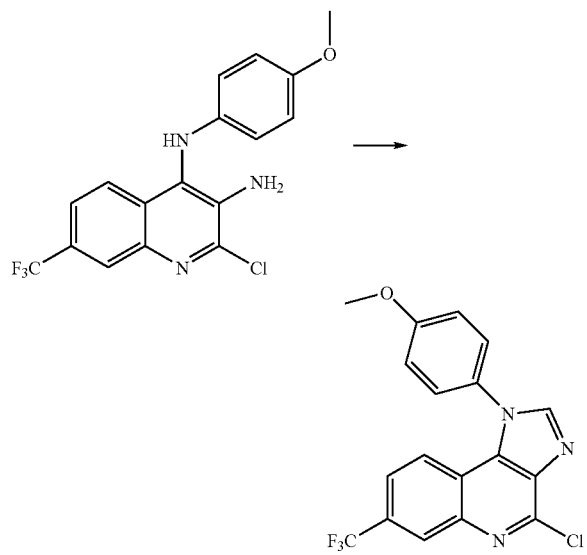

To a suspension of 2-chloro-N-4-(4-methoxyphenyl)-7-(trifluoromethyl)quinoline-3,4-diamine (181 mg; 0.49 mmol; 1 eq) in dry toluene (9 mL), are added successively triethyl orthoformate (164 µL; 0.98 mmol; 2 eq) and PTSA (9.4 mg; 0.49 mmol; 0.1 eq). The crude mixture is heated to reflux and allowed to stir for 3 hours until completion of the reaction. The solution is then cooled to room temperature and concentrated under reduced pressure. The resulting crude residue is purified on silica gel (ethyl acetate/cyclohexane 3:7) to afford the title compound as a white powder (153 mg; 0.40 mmol; 82%)

$^1$H NMR (CDCl$_3$), δ (ppm): 8.48 (s, 1H), 8.13 (s, 1H), 7.55-7.40 (m, 2H), 7.46 (d, J=6.8 Hz, 2H), 7.17 (d, J=6.8 Hz, 2H), 3.98 (s, 3H)

Step 8: Synthesis of 3-{[1-(4-methoxyphenyl)-7-(trifluoromethyl)-1H-imidazo[4,5-c]quinolin-4-yl]amino}propan-1-ol

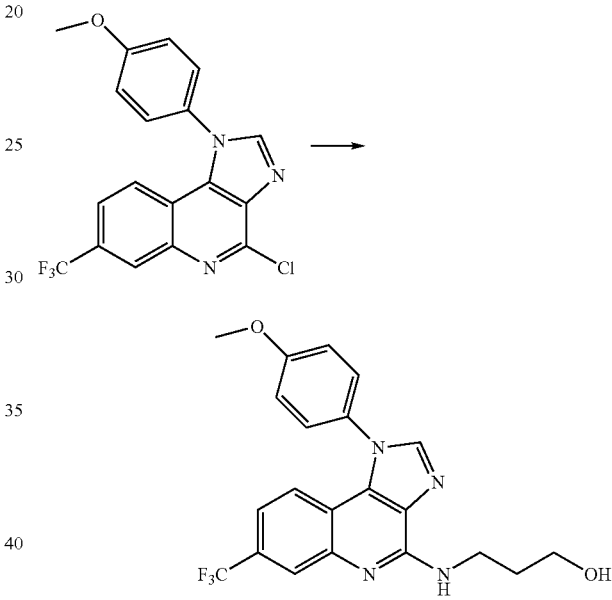

To a solution of 4-chloro-1-(4-methoxy-phenyl)-7-trifluoromethyl-1H-imidazo[4,5-c]quinoline (153 mg; 0.41 mmol; 1 eq) in anhydrous 1,4-dioxane (18 mL), 3-aminopropanol (77 µL; 1.0 mmol; 2.5 eq) is added. The resulting solution is heated to reflux and allowed to stir for 19 hours after which period the reaction is still not complete on TLC. Thus, additional 3-aminopropanol (523 µL; 6.9 mmol; 17 eq) is added and the stirring is continued under reflux for 4 hours. The crude mixture is diluted with ethyl acetate (40 mL) and washed three times with a 1M aqueous solution of NaOH (3×40 mL). Aqueous layers are combined and re-extracted with ethyl acetate (75 mL). All organic layers are combined, dried over sodium sulfate and concentrated. The crude residue is purified on silica gel (cyclohexane/ethyl acetate 2:8) to afford the title compound as an off-white powder (145 mg; 0.35 mmol; 85%).

$^1$H NMR (CD$_3$OD), δ (ppm): 8.19 (s, 1H), 7.96 (s, 1H), 7.54 (d, J=8.8 Hz, 2H), 7.40-4.10 (m, 2H), 7.22 (d, J=8.8 Hz, 2H), 3.94 (s, 3H), 3.82 (t, J=6.3 Hz, 2H), 3.72 (t, J=6.3 Hz, 2H), 1.96 (qt, J=6.3 Hz, 2H)

APPI-MS m/z 417.1 (M+H)$^+$

Example 25

3-{[1-methyl-7-(trifluoromethyl)-1H-imidazo[4,5-c]quinolin-4-yl]amino}propan-1-ol Step 1: Synthesis of 2-chloro-N-methyl-3-nitro-7-(trifluoromethyl)quinolin-4-amine

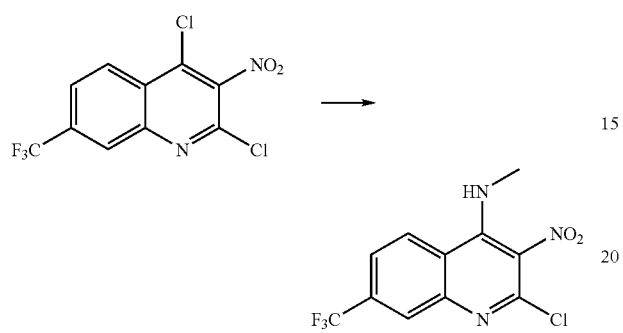

Prepared according to Example 24 Step 5 to afford the title compound as a yellow powder (200 mg; 0.65 mmol; 93%)

$^1$H NMR (DMSO-d$_6$), δ (ppm): 8.59 (d, J=8.8 Hz, 1H), 8.56 (br s, 1H), 8.15 (s, 1H), 7.97 (d, J=8.8 Hz, 1H), 2.85 (d, J=5.4 Hz, 3H)

Step 2: Synthesis of 2-chloro-N-4-methyl-7-(trifluoromethyl)quinoline-3,4-diamine

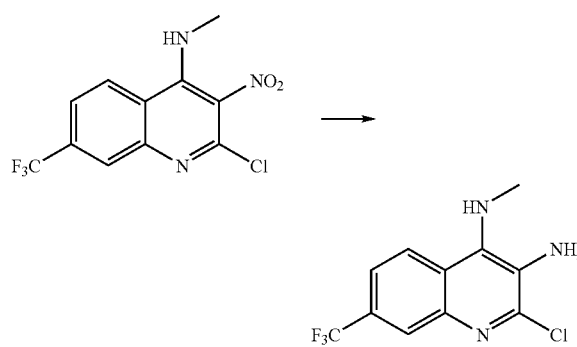

Prepared according to Example 24 Step 6 to afford the title compound as a green powder (180 mg; 0.65 mmol; 100%)

$^1$H NMR (CDCl$_3$), δ (ppm): 8.20 (s, 1H), 7.92 (d, J=8.8 Hz, 1H), 7.62 (d, J=8.8 Hz, 1H), 4.26 (br s, 2H), 3.03 (s, 3H)

Step 3: Synthesis of 4-chloro-1-methyl-7-(trifluoromethyl)-1H-imidazo[4,5-c]quinoline

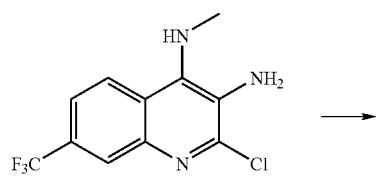

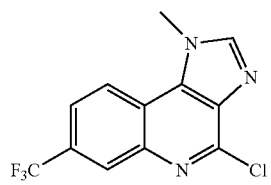

Prepared according to Example 24 Step 7 to afford the title compound as a white powder (139 mg; 0.49 mmol; 75%)

$^1$H NMR (DMSO-d$_6$), δ (ppm): 8.73 (d, J=8.3 Hz, 1H), 8.58 (s, 1H), 8.45 (s, 1H), 8.00 (d, J=8.3 Hz, 1H), 4.35 (s, 3H)

Step 4: Synthesis of 3-{[1-methyl-7-(trifluoromethyl)-1H-imidazo[4,5-c]quinolin-4-yl]amino}propan-1-ol

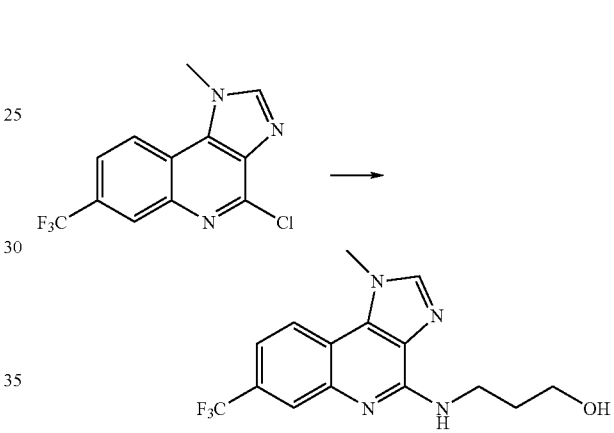

Prepared according to Example 24 Step 8 to afford the title compound as a white powder (143 mg; 0.44 mmol; 90%).

$^1$H NMR (CD$_3$OD), δ (ppm): 8.35 (d, J=8.3 Hz, 1H), 8.12 (s, 1H), 7.99 (s, 1H), 7.44 (d, J=8.3 Hz, 1H), 4.27 (s, 3H), 3.79 (t, J=6.3 Hz, 2H), 3.71 (t, J=6.4 Hz, 2H), 1.94 (qt, J=6.3 Hz, 2H)

APPI-MS m/z 325 (M+H)$^+$

Example 26

4-[4-(3-hydroxy-propylamino)-7-trifluoromethyl-imidazo[4,5-c]quinolin-1-yl]-cyclohexanol Step 1: Synthesis of trans-4-{[2-chloro-3-nitro-7-(trifluoromethyl)quinolin-4-yl]amino}cyclohexanol

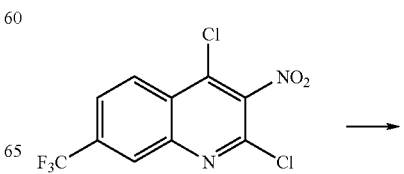

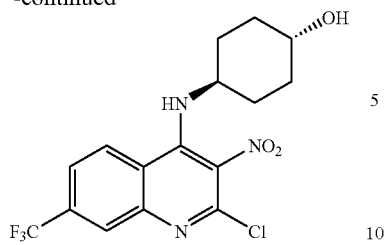

Prepared according to Example 24 Step 5 to afford the title compound as a yellow powder (190 mg; 0.49 mmol; 70%)

$^1$H NMR (DMSO-d$_6$), δ (ppm): 8.77 (d, J=8.8 Hz, 1H), 8.16 (s, 1H), 7.96 (d, J=8.6 Hz, 1H), 7.66 (d, J=8.8 Hz, 1H), 4.61 (d, J=4.9 Hz, 1H), 3.52-3.05 (m, 2H), 1.98-1.80 (m, 4H), 1.75-1.45 (m, 2H), 1.30-0.95 (m, 2H)

Step 2: Synthesis of trans-4-{[3-amino-2-chloro-7-(trifluoromethyl)quinolin-4-yl]amino}cyclohexanol

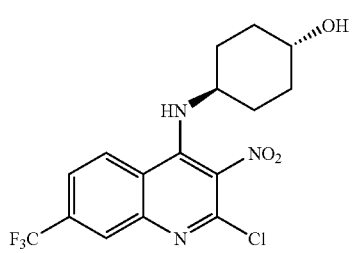

Prepared according to Example 24 Step 6 to afford the title compound as a green powder (>175 mg; >0.49 mmol; 100%) which is used without further purification $^1$H NMR (CDCl$_3$), δ (ppm): 8.19 (s, 1H), 7.83 (d, J=8.8 Hz, 1H), 7.61 (d, J=8.8 Hz, 1H), 4.32 (br s, 2H), 4.12 (d, J=5.8 Hz, 1H), 3.85-3.15 (m, 3H), 2.15-1.80 (m, 4H), 1.80-1.00 (m, 4H)

Step 3: Synthesis of trans-4-[4-chloro-7-(trifluoromethyl)-1H-imidazo[4,5-c]quinolin-1-yl]cyclohexanol

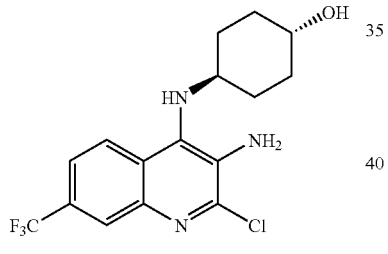

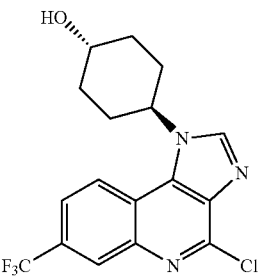

Prepared according to Example 24 Step 7 to afford the title compound as an off-white powder (144 mg; 0.39 mmol; 80%)

$^1$H NMR (DMSO-d$_6$), δ (ppm): 8.76 (s, 1H), 8.61 (d, J=9.3 Hz, 2H), 8.45 (s, 1H), 8.05 (d, J=9.3 Hz, 2H), 4.99 (br s, 1H), 4.83 (d, J=3.4 Hz, 1H), 3.60 (s, 1H), 2.50-1.50 (m, 8H)

Step 4: Synthesis of 4-[4-(3-hydroxy-propylamino)-7-trifluoromethyl-imidazo[4,5-c]quinolin-1-yl]-cyclohexanol

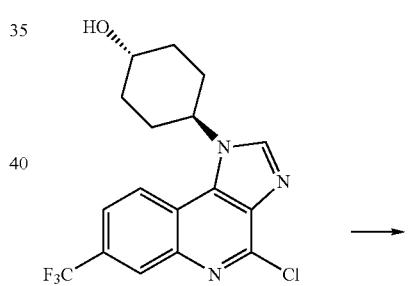

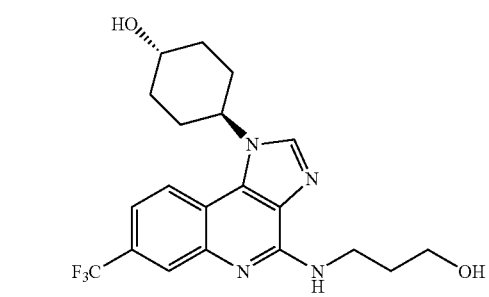

Prepared according to Example 24 Step 8 to afford the title compound as a white powder (115 mg; 0.28 mmol; 72%)

$^1$H NMR (CD$_3$OD), δ (ppm): 8.36 (s, 1H), 8.22 (d, J=8.3 Hz, 2H), 8.01 (s, 1H), 7.57 (d, J=8.3 Hz, 1H), 3.80 (t, J=6.3 Hz, 2H), 3.71 (t, J=6.3 Hz, 2H), 1.98 (qt, J=6.3 Hz, 2H), 2.55-1.55 (m, 8H)

APPI-MS m/z 409.1 (M+H)$^+$

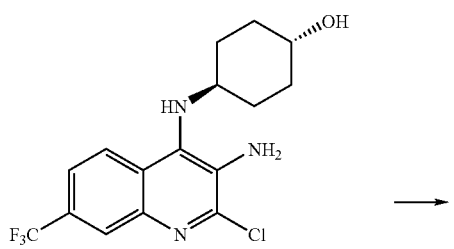

Example 27

3-[1-(1,2,3,6-tetrahydro-pyridin-4-yl)-7-trifluoromethyl-imidazo[1,2-a]quinoxalin-4-ylamino]-propan-1-ol

Step 1: Synthesis of 4-[4-(3-hydroxy-propylamino)-7-trifluoromethyl-imidazo[1,2-a]quinoxalin-1-yl]-3,6-dihydro-2H-pyridine-1-carboxylic acid tert-butyl ester

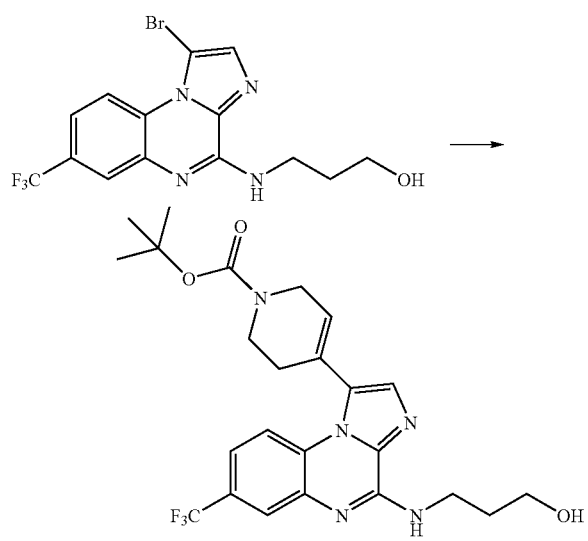

Prepared from commercially available (Digital Speciality Chemicals) 3,6-dihydro-2H-pyridine-1-tert-butoxycarbonyl-4-boronic acid pinacol ester according to the general procedure for Suzuki couplings as described beforehand.

$^1$H NMR (DMSO-d$_6$), δ (ppm): 8.03 (m, 1H), 7.97 (d, J=8.8 Hz, 1H), 7.83 (s, 1H), 7.65 (d, J=8.8 Hz, 1H), 7.45 (s, 1H), 6.19 (s, 1H), 4.63 (m, 1H), 4.11 (m, 2H), 3.71 (m, 2H), 3.63 (m, 2H), 3.53 (q, J=6.8 Hz, 2H), 2.34 (m, 2H), 1.82 (qt, J=6.8 Hz, 2H), 1.46 (s, 9H)

Step 2: Synthesis of 3-[1-(1,2,3,6-tetrahydro-pyridin-4-yl)-7-trifluoromethyl-imidazo[1,2-a]quinoxalin-4-ylamino]-propan-1-ol

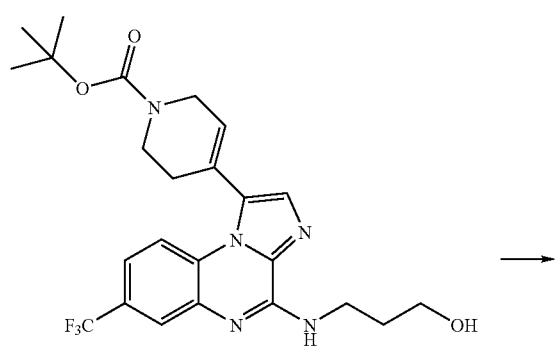

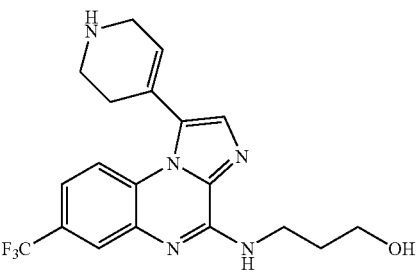

To a solution of 4-[4-(3-hydroxy-propylamino)-7-trifluoromethyl-imidazo[1,2-a]quinoxalin-1-yl]-3,6-dihydro-2H-pyridine-1-carboxylic acid tert-butyl ester (1.10 g; 2.30 mmol; 1 eq) in anhydrous dichloromethane (12 mL) is slowly added trifluoroacetic acid (1.77 mL; 23.0 mmol; 10 eq). The solution is allowed to stir for 6 hours at room temperature until completion of the reaction. The reaction mixture is concentrated and the residual traces of trifluoroacetic acid are removed by co-distillation with toluene (2×10 mL). The red gum is taken up in water (73 mL) and the resulting aqueous solution is washed with ethyl acetate (375 mL) before adjusting the pH to 8 by addition of sodium bicarbonate in powder. This basic aqueous layer is then extracted with ethyl acetate (5×100 mL). The organic extracts are combined, dried over sodium sulfate and concentrated in vacuum. The resulting crude residue is then passed through a silica gel column (ethyl acetate/methanol 8:2 then ethyl acetate/methanol/triethylamine 8:2:0.3) to afford the title compound still contaminated with minor impurities. The powder is then washed with ether to afford the title compound as an off-white solid (170 mg; 0.44 mmol; 19%)

$^1$H NMR (DMSO-$_6$), δ (ppm): 8.12 (d, J=8.8 Hz, 1H), 7.98 (m, 1H), 7.81 (s, 1H), 7.58 (d, J=8.8 Hz, 1H), 7.39 (s, 1H), 6.18 (s, 1H), 4.63 (m, 1H), 3.62 (m, 2H), 3.52 (m, 2H), 3.45 (m, 2H), 3.32 (br s, 1H), 3.02 (m, 2H), 2.21 (m, 2H), 1.82 (qt, J=6.8 Hz, 2H)

APPI-MS m/z 392.2 (M+H)$^+$

Example 28

1-{4-[4-(3-hydroxy-propylamino)-7-trifluoromethyl-imidazo[1,2-a]quinoxalin-1-yl]-3,6-dihydro-2H-pyridin-1-yl}-ethanone

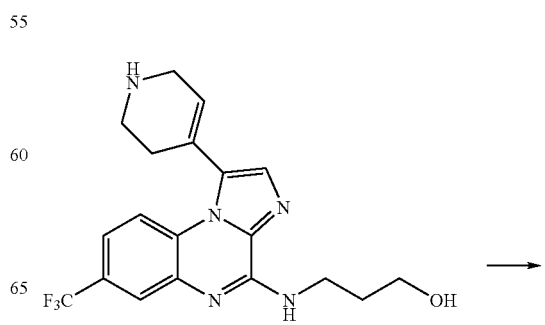

57

-continued

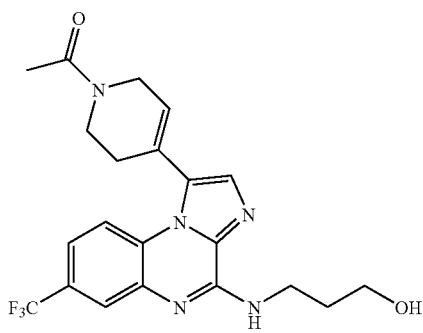

To a solution of 3-[1-(1,2,3,6-tetrahydro-pyridin-4-yl)-7-trifluoromethyl-imidazo[1,2-a]quinoxalin-4-ylamino]-propan-1-ol prepared in the previous example (50.0 mg; 0.132 mmol; 1 eq) in anhydrous dichloromethane (660 µL) are successively added N,N'-dimethylaminopyridine (16.1 mg; 0.132 mmol; 1 eq) and acetyl chloride (9.4 µL; 0.132 mmol; 1 eq). The solution is allowed to stir for 17 hours at room temperature until completion of the reaction. The reaction mixture is concentrated under vacuum and the resulting residue is taken-up in ethyl acetate (10 mL). The resulting organic solution is washed with brine (10 mL), dried over sodium sulfate, filtered and concentrated in vacuum. The resulting residue is passed through a silica gel column (dichloromethane/methanol 95:5) to afford the title compound as an off-white solid (20 mg; 0.048 mmol; 36%)

$^1$H NMR (CDCl$_3$), δ (ppm) (2 rotamers): 7.96 (s, 1H), 7.93 (d, J=8.8 Hz, 1H from one rotamer), 7.85 (d, J=8.8 Hz, 1H from one rotamer), 7.46 (d, J=8.8 Hz, 1H), 7.35 (s, 1H), 6.60-6.50 (m, 1H), 6.23 (br s, 1H from one rotamer), 6.15 (br s, 1H from one rotamer), 4.66 (br s, 1H), 4.50-4.35 (m, 2H from one rotamer), 4.33-4.18 (m, 2H from one rotamer), 4.00-3.55 (m, 6H), 2.60-2.47 (m, 2H), 2.22 (s, 3H), 1.90 (qt, J=5.8 Hz, 2H)

APPI-MS m/z 434.1 (M+H)$^+$

Example 29

3-[1-(1-methanesulfonyl-1,2,3,6-tetrahydro-pyridin-4-yl)-7-trifluoromethyl-imidazo[1,2-a]quinoxalin-4-ylamino]-propan-ol

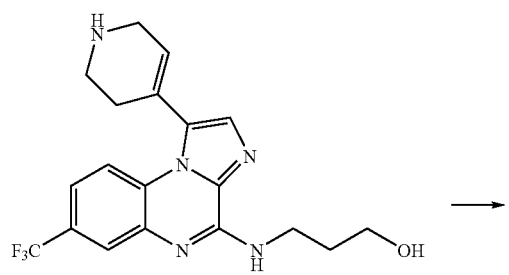

58

-continued

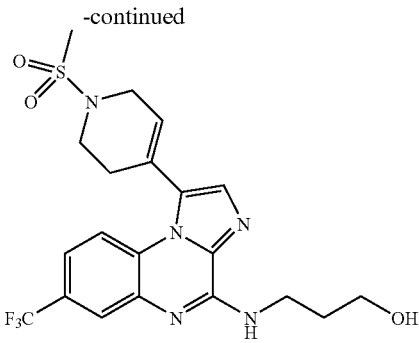

To a solution of 3-[1-(1,2,3,6-tetrahydro-pyridin-4-yl)-7-trifluoromethyl-imidazo[1,2-a]quinoxalin-4-ylamino]-propan-1-ol as prepared in example 27 (50.0 mg; 0.132 mmol; 1 eq) in anhydrous dichloromethane (660 µL) are successively added N,N'-dimethylaminopyridine (16.1 mg; 0.132 mmol; 1 eq) and mesyl chloride (10.3 µL; 0.132 mmol; 1 eq). The solution is allowed to stir at room temperature for 17 hours after which period the reaction is almost complete. The reaction mixture is concentrated under vacuum and the resulting residue is taken-up with ethyl acetate (10 mL). The organic solution is washed with brine (10 mL), dried over sodium sulfate, filtered and concentrated in vacuum. Two successive column chromatography on silica gel (eluent column 1: ethyl acetate/methanol/triethylamine 8:2:0.2; eluent column 2: dichloromethane/methanol 95:5) and one column chromatography on reversed-phase (C18, acetonitrile) affords the title compound as a white solid (9 mg; 0.020 mmol; 15%)

$^1$H NMR (CDCl$_3$), δ (ppm): 7.96 (s, 1H), 8.92 (d, J=8.4 Hz, 1H), 7.48 (d, J=8.4 Hz, 1H), 7.36 (s, 1H), 6.65-6.40 (m, 1H), 6.21 (s, 1H), 4.62 (br s, 1H), 4.10 (d, J=2.9 Hz, 2H), 3.89 (q, J=5.8 Hz, 2H), 3.75-3.50 (m, 4H), 2.96 (s, 3H), 2.65-2.50 (m, 2H), 1.90 (qt, J=5.8 Hz, 2H)

APPI-MS m/z 470.1 (M+H)$^+$

Example 30

Synthesis of 3-{[1-ethynyl-7-(trifluoromethyl)imidazo[1,2-a]quinoxalin-4-yl]amino}propan-1-ol Step 1: Synthesis of 3-({1-[(trimethylsily)ethynyl]-7-(trifluoromethyl)imidazo[1,2-a]quinoxalin-4-yl}amino)propan-1-ol

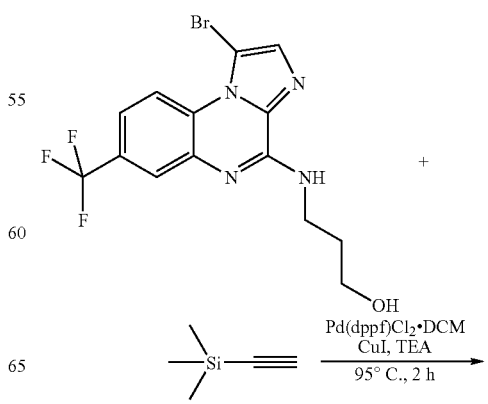

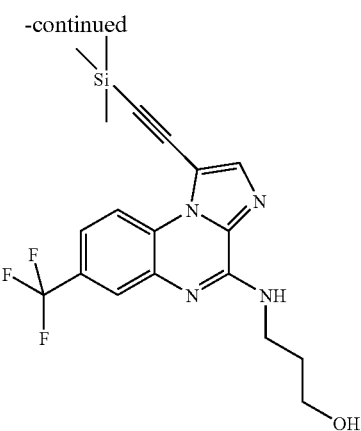

To a suspension of 3-{[1-bromo-7-(trifluoromethyl)imidazo[1,2-a]quinoxalin-4-yl]amino}propan-1-ol as prepared in example 2 (100 mg, 0.26 mmol), ethynyltrimethylsilane (81 µL, 0.57 mmol) and copper iodide (5 mg, 0.026 mmol) in anhydrous triethylamine (3.5 mL) degassed under argon for 10 minutes was added Pd(dppf)Cl$_2$.DCM (11 mg, 0.013 mmol). The mixture was stirred at 90° C. for 1 h45 and then allowed to cool to room temperature, poured onto a saturated aqueous solution of ammonium chloride and extracted three times with ethyl acetate/tetrahydrofuran (1:1). The combined organic layers were dried over sodium sulfate, filtered and evaporated. The crude product was purified by preparative TLC (silica gel, dichloromethane/methanol 20/1) to afford the title compound (80 mg, 75%) as an off-white solid.

ESI-MS m/z 407 (M+H)$^+$.

Step 2: Synthesis of 3-{[1-ethynyl-7-(trifluoromethyl)imidazo[1,2-a]quinoxalin-4-yl]amino}propan-1-ol

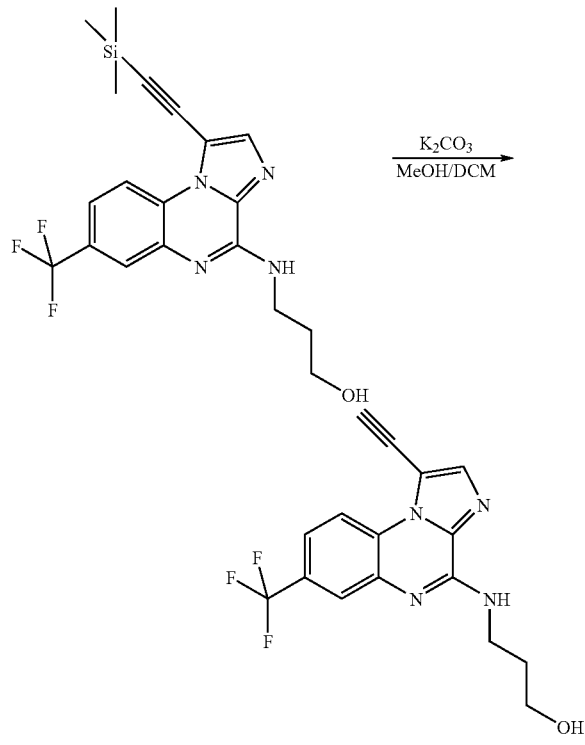

To a solution of 3-({1-[(trimethylsilyl)ethynyl]-7-(trifluoromethyl)imidazo[1,2-a]quinoxalin-4-yl}amino)propan-1-ol (80 mg, 0.20 mmol) in dichloromethane (1 mL) and methanol (1 mL) was added potassium carbonate (136 mg, 0.98 mmol). The heterogeneous mixture was stirred under argon at room temperature for 1 h and then diluted with brine and dichloromethane. The organic layer was washed three times with brine and the combined aqueous layers were extracted three times with dichoromethane. The combined organic extracts were dried over sodium sulfate, filtered and evaporated to afford the title compound (61 mg, 91%) as a yellow solid. The crude product was used without further purification.

ESI-MS m/z 335 (M+H)$^+$.

General Procedure for [3+2] Cycloaddition for the Synthesis of Examples 31 to 33

To a solution of an aldehyde (1 eq) in anhydrous acetonitrile, under argon, was added tosylhydrazide (1 eq). After 3 h of stirring at room temperature, a solution of sodium hydroxide 5M (1 eq) was added and the mixture was stirred for 20 minutes during which a small precipitate was formed. A suspension of the 3-{[1-ethynyl-7-(trifluoromethyl)imidazo[1,2-a]quinoxalin-4-yl]amino}propan-1-ol (0.5 eq) in anhydrous acetonitrile was added and the reaction mixture was stirred at 50° C. for 48 h. Concentration gave a residue that was diluted with cold water and extracted four times with ethyl acetate. The combined organic layers were dried over sodium sulfate, filtered and evaporated. The crude product was purified by preparative TLC (silica gel, mixture of dichloromethane/methanol) to afford the desired compound.

Example 31

Synthesis of 3-({1-[1H-pyrazol-3-(4-methoxyphenyl)-5-yl]-7-(trifluoromethyl)imidazo[1,2-a]quinoxalin-4-yl}amino)propan-1-ol

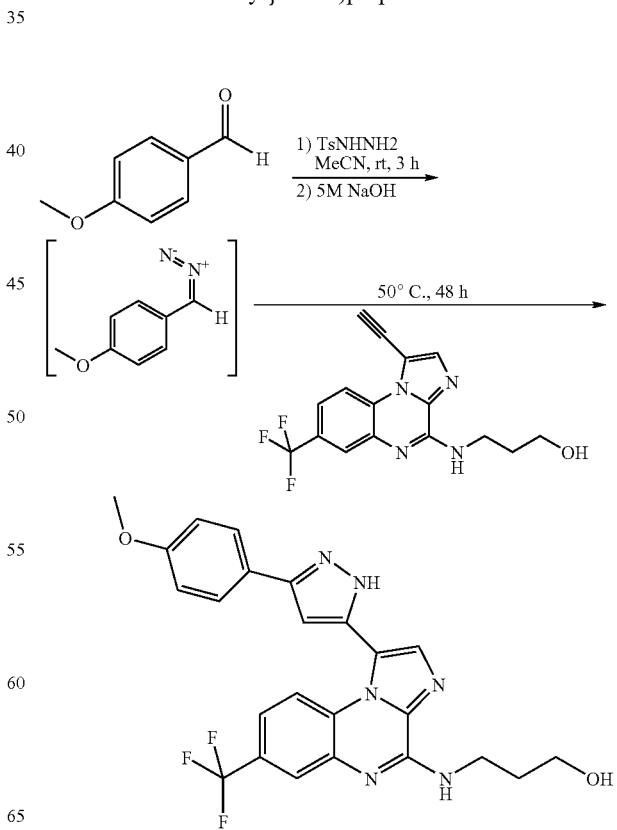

To a solution of 4-methoxybenzaldehyde (30 μL, 0.24 mmol) in anhydrous acetonitrile (2 mL), under argon, was added tosylhydrazide (45 mg, 0.24 mmol). After 3 h of stirring at room temperature, a solution of sodium hydroxide 5M (48 μL, 0.24 mmol) was added and the mixture was stirred for 20 minutes during which a small precipitate was formed. A suspension of the 3-{[1-ethynyl-7-(trifluoromethyl)imidazo[1,2-a]quinoxalin-4-yl]amino}propan-1-ol (40 mg, 0.12 mmol) in anhydrous acetonitrile (0.8 mL) was added and the reaction mixture was stirred at 50° C. for 48 h. Concentration gave a residue that was diluted with cold water and extracted four times with ethyl acetate. The combined organic layers were dried over sodium sulfate, filtered and evaporated. The crude product was purified by preparative TLC (silica gel, dichloromethane/methanol 20/1) yielding a yellow solid Recrystallization from dichloromethane/methanol and cyclohexane afforded the title compound (3 mg, 5%) as a white solid.

$^1$H NMR (CD$_3$OD), δ (ppm): 8.07 (s, 1H), 7.98 (d, J=8.5 Hz, 1H), 7.83 (s, 1H), 7.76 (d, J=8.8 Hz, 2H), 7.56 (d, J=8.5 Hz, 1H), 7.06 (d, J=8.8 Hz, 2H), 6.95 (s, 1H), 3.87-3.90 (m, 5H), 3.79 (t, J=5.9 Hz, 2H), 2.07 (qt, J=6.1 Hz, 2H)

ESI-MS m/z 483 (M+H)$^+$

Example 32

3-({1-[3-phenyl-1H-pyrazol-5-yl]-7-(trifluoromethyl)imidazo[1,2-a]quinoxalin-4-yl}amino)propan-1-ol

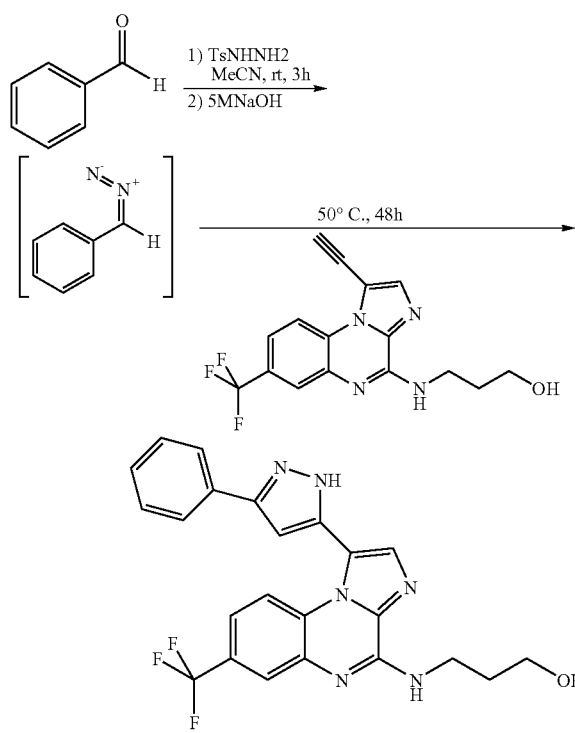

Prepared according to the general procedure for [3+2] cycloaddition as described beforehand to give a beige solid (31%).

$^1$H NMR (CD$_3$OD), δ (ppm): 7.92 (s, 1H), 7.89-7.77 (m, 2H), 7.69 (s, 1H), 7.50-7.37 (m, 4H), 7.28 (d, J=8.9 Hz, 1H), 6.98 (br s, 1H), 3.81 (t, J=6.6 Hz, 2H), 3.76 (t, J=6.0 Hz, 2H), 1.97 (qt, J=6.2 Hz, 2H)

ESI-MS m/z 453 (M+H)$^+$

Example 33

3-({1-[3-(3-pyridinyl)-1H-pyrazol-5-yl]-7-(trifluoromethyl)imidazo[1,2-a]quinoxalin-4-yl}amino)propan-1-ol

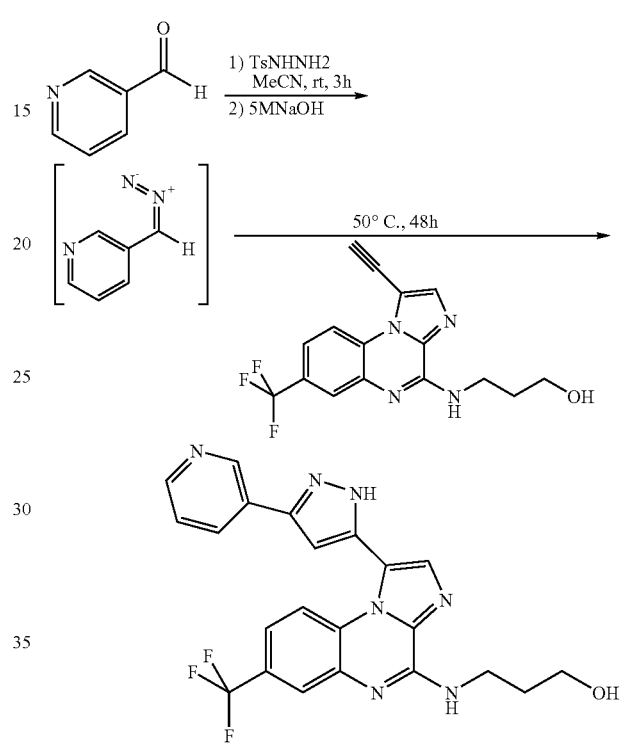

Prepared according to the general procedure for [3+2] cycloaddition as described beforehand to give a white solid (9%).

$^1$H NMR (CD$_3$OD), δ (ppm): 9.14 (s, 1H), 8.63 (d, J=5.6 Hz, 1H), 8.39 (br s, 1H), 7.99 (s, 1H), 7.79 (s, 1H), 7.63 (t, J=5.5 Hz, 1H), 7.39 (d, J=8.9 Hz, 2H), 7.25 (s, 1H), 3.88 (t, J=6.4 Hz, 3H), 3.81 (t, J=6.1 Hz, 2H), 2.06 (qt, J=6.5 Hz, 2H)

ESI-MS m/z 454 (M+H)$^+$

Example 34

3-{[1-(1-phenyl-1H-1,2,3-triazol-4-yl)-7-(trifluoromethyl)imidazo[1,2-a]quinoxalin-4-yl]amino}propan-1-ol Step 1: Synthesis of (azidomethyl)benzene

To a solution of benzylbromide (350 μL, 2.92 mmol) in anhydrous dimethylformamide (7 mL), under argon, was added sodium azide (288 mg, 6.43 mmol). After 24 h at room temperature, the reaction mixture was diluted with ethyl acetate and then washed three times with brine. The combined organic layers were dried over sodium sulfate, filtered and evaporated. The residue was diluted with water and extracted with pentane, dried over sodium sulfate, filtered and evaporated to afford the title compound (309 mg, 80%) as a colorless oil.

Step 2: Synthesis of 3-{[1-(1-phenyl-1H-1,2,3-triazol-4-yl)-7-(trifluoromethyl)imidazo[1,2-a]quinoxalin-4-yl]amino}propan-1-ol

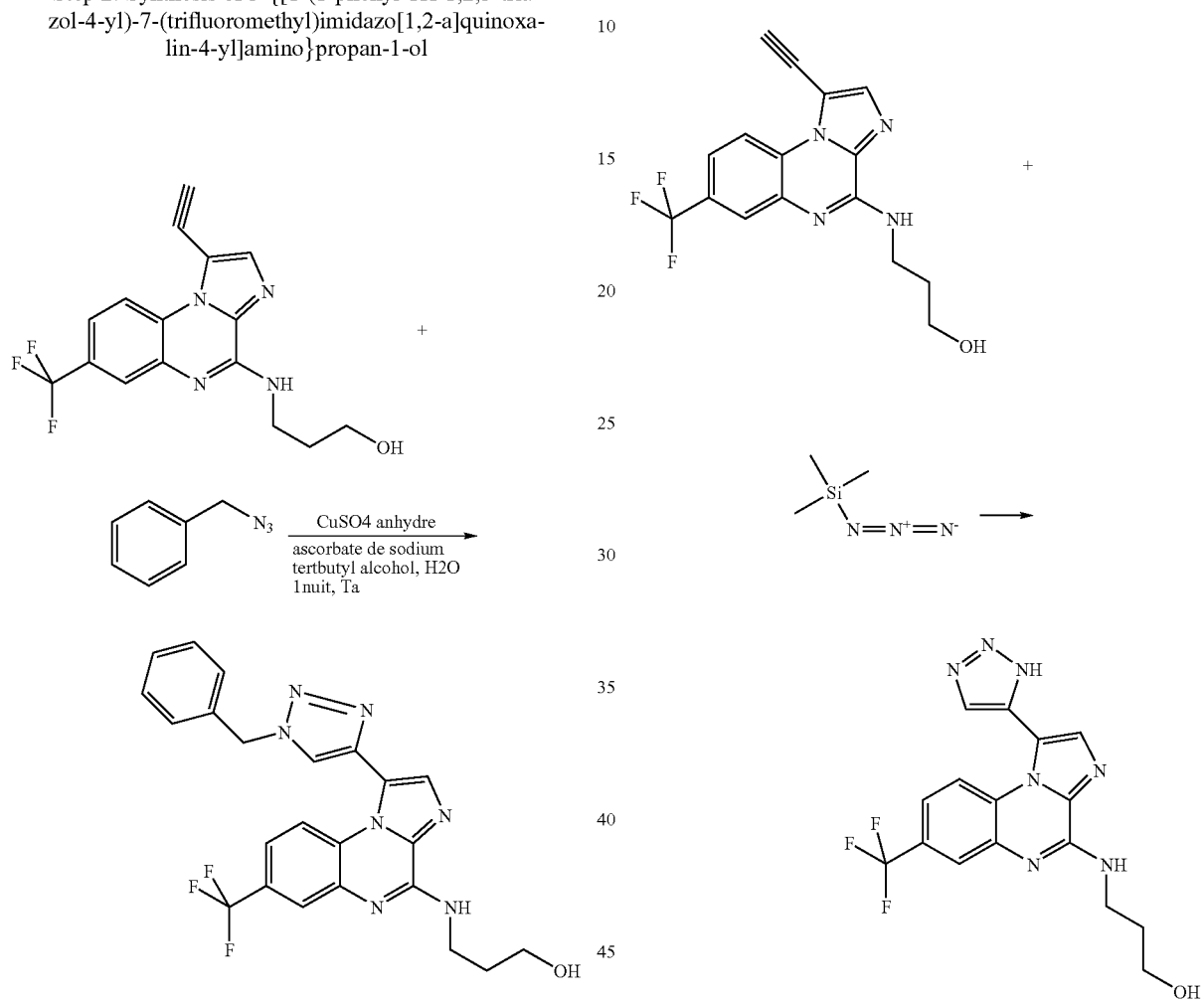

To a solution of (azidomethyl)benzene (16 mg, 0.12 mmol) in t-butyl alcohol (0.12 mL) and water (0.12 mL), under argon, was added 3-{[1-ethynyl-7-(trifluoromethyl)imidazo[1,2-a]quinoxalin-4-yl]amino}propan-1-ol as prepared in example 30 (40 mg, 0.12 mmol), copper sulfate (0.2 mg, 0.0012 mmol) and a freshly prepared 1M aqueous solution of sodium ascorbate (0.012 mL, 0.012 mmol). After 18 h at room temperature, a white precipitate was formed. Water was added to the reaction mixture then cooled with an ice bath. The precipitate was filtered, washed with cold water and then dried under vacuum. The crude product was purified by preparative TLC (silica gel, ethyl acetate) to afford the title compound (4 mg, 7%) as a white solid.

$^1$H NMR (CDCl$_3$), δ (ppm): 7.95 (s, 1H), 7.80-7.71 (m, 2H), 7.54 (s, 1H), 7.51-7.36 (m, 5H), 7.31-7.23 (m, 1H), 6.71 (br s, 1H), 5.71 (s, 2H), 3.96-3.85 (m, 2H), 3.71 (t, J=5.4 Hz, 2H), 1.97-1.86 (m, 2H)

ESI-MS m/z 468 (M+H)$^+$

Example 35

3-{[1-(1H-1,2,3-triazol-5-yl)-7-(trifluoromethyl)imidazo[1,2-a]quinoxalin-4-yl]amino}propan-1-ol

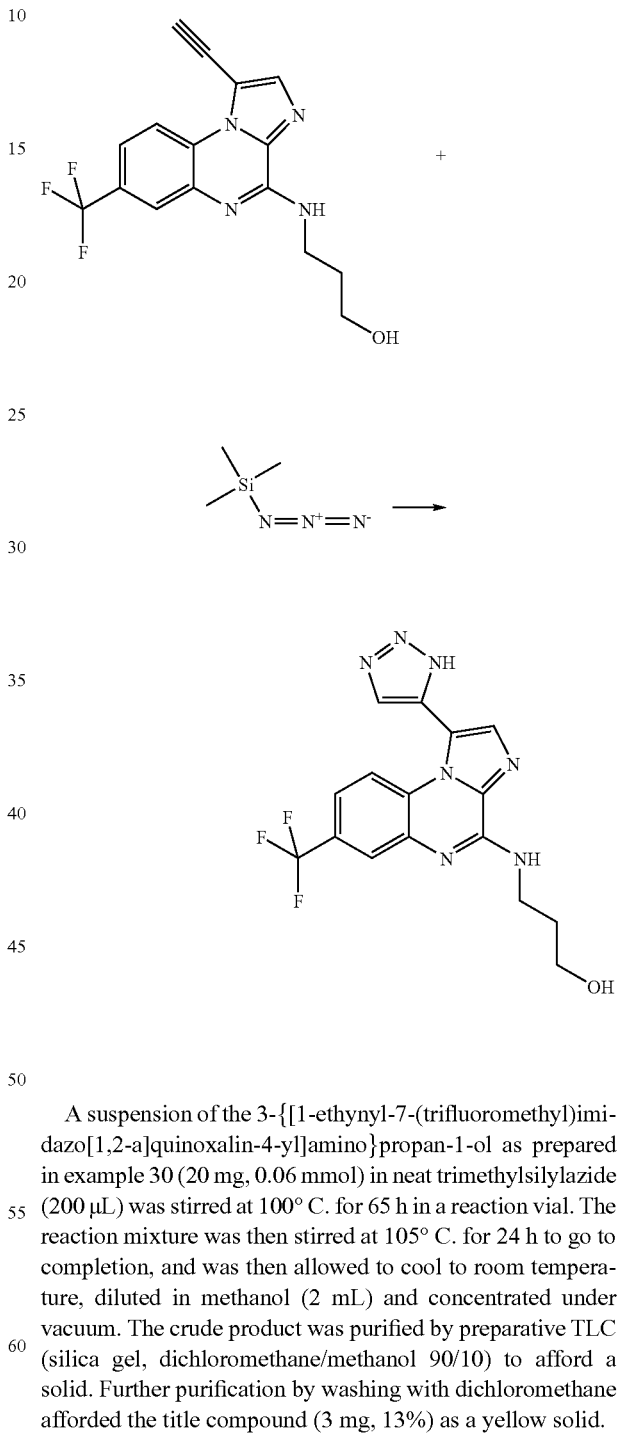

A suspension of the 3-{[1-ethynyl-7-(trifluoromethyl)imidazo[1,2-a]quinoxalin-4-yl]amino}propan-1-ol as prepared in example 30 (20 mg, 0.06 mmol) in neat trimethylsilylazide (200 μL) was stirred at 100° C. for 65 h in a reaction vial. The reaction mixture was then stirred at 105° C. for 24 h to go to completion, and was then allowed to cool to room temperature, diluted in methanol (2 mL) and concentrated under vacuum. The crude product was purified by preparative TLC (silica gel, dichloromethane/methanol 90/10) to afford a solid. Further purification by washing with dichloromethane afforded the title compound (3 mg, 13%) as a yellow solid.

$^1$H NMR (CD$_3$OD), δ (ppm): 8.27 (br s, 1H), 8.04 (s, 1H), 7.77-7.80 (m, 2H), 7.50 (d, J=8.7 Hz, 1H), 3.87 (t, J=6.7 Hz, 2H), 3.78 (t, J=6.0 Hz, 2H), 2.07 (qt, J=6.1 Hz, 2H)

ESI-MS m/z 378 (M+H)$^+$

Example 36

3-({1-[3-tert-butyl-1H-pyrazol-5-yl]-7-(trifluoromethyl)imidazo[1,2-a]quinoxalin-4-yl}amino)propan-1-ol Step 1: Synthesis of 1-ethynyl-N-[3-(tetrahydro-2H-pyran-2-yloxy)propyl]-7-(trifluoromethyl)imidazo[1,2-a]quinoxalin-4-amine

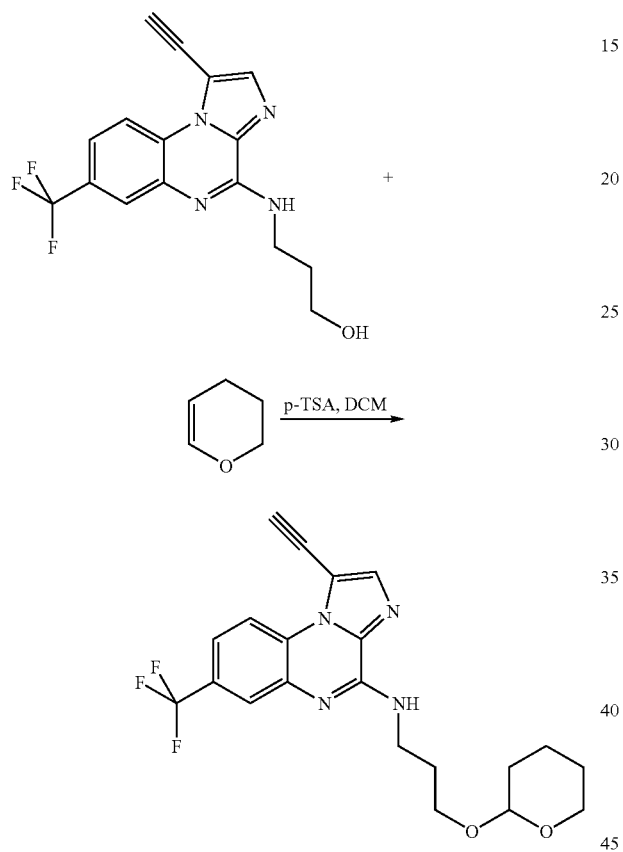

General Procedure for THP Protection:

To a solution of a primary alcohol (1 eq) in anhydrous dichloromethane cooled at 0° C. were added 3,4-dihydro-2H-pyran (1.2 eq) and para-toluenesulfonic acid (0.1 eq). The mixture was stirred at room temperature overnight and then poured onto a saturated aqueous solution of sodium hydrogencarbonate and extracted twice with dichloromethane. The combined organic layers were washed with water and brine, dried over sodium sulfate, filtered and evaporated. The crude product was purified by flash chromatography (silica gel, mixture of dichloromethane/methanol) to afford the desired compound.

To a solution of 3-{[1-ethynyl-7-(trifluoromethyl)imidazo[1,2-a]quinoxalin-4-yl]amino}propan-1-ol as prepared in example 30 (334 mg, 1.0 mmol) in anhydrous dichloromethane (10 mL) cooled at 0° C., were added 3,4-dihydro-2H-pyran (109 µL, 1.2 mmol) and para-toluenesulfonic acid (19 mg, 0.1 mmol). The mixture was stirred at room temperature overnight and then poured onto a saturated aqueous solution of sodium hydrogenocarbonate and extracted twice with dichloromethane. The combined organic layers were washed with water and brine, dried over sodium sulfate, filtered and evaporated. The crude product was purified by flash chromatography (silica gel, dichloromethane/methanol 20/1) to afford the title compound (302 mg, 72%) as a white solid.

ESI-MS m/z 419 (M+H)+.

Step 2: Synthesis of 1-{N-[3-(tetrahydro-2H-pyran-2-yloxy)propyl]-7-(trifluoromethyl)]imidazo[1,2-a]quinoxalin-1-yl}-4,4-dimethylpent-1-yn-3-one

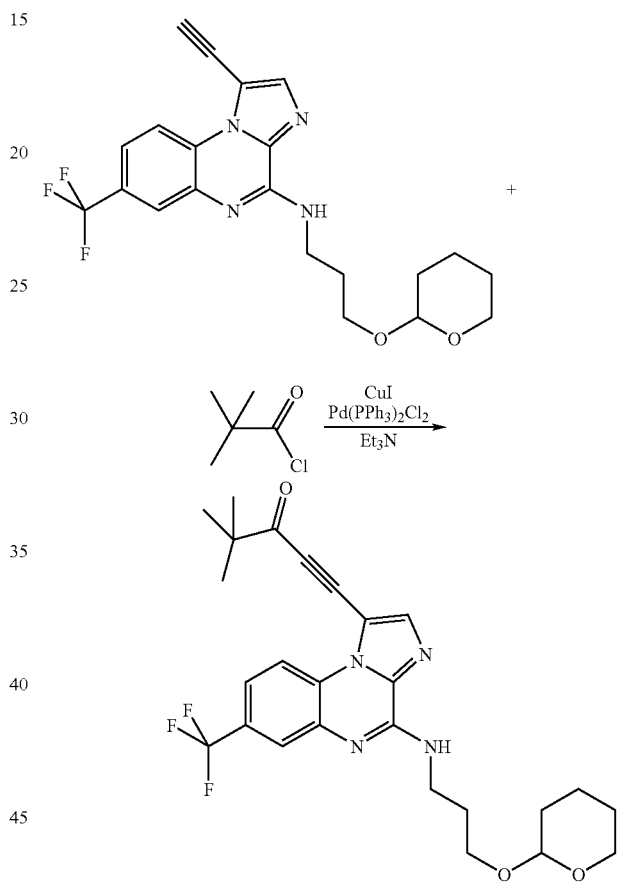

To a solution of 1-ethynyl-N-[3-(tetrahydro-2H-pyran-2-yloxy)propyl]-7-(trifluoromethyl)imidazo[1,2-a]quinoxalin-4-amine (22 mg, 0.052 mmol), copper iodide (0.5 mg, 0.0026 mmol) and Pd(PPh$_3$)Cl$_2$ (1 mg, 0.001 mmol) in anhydrous triethylamine (0.5 mL) was added pivaloyl chloride (7 µL, 0.052 mmol) under an argon atmosphere. The mixture was stirred at room temperature for several days, poured onto water and extracted four times with ethyl acetate. The combined organic layers were dried over sodium sulfate, filtered and evaporated. The crude product was purified by preparative TLC (silica gel, dichloromethane/methanol 20/1) to afford the title compound (13 mg, 50%) as an off-white solid.

$^1$H NMR (CDCl$_3$), δ (ppm): 9.00 (d, J=8.7 Hz, 1H), 8.05 (s, 1H), 7.99 (s, 1H), 7.54 (d, J=8.7 Hz, 1H), 6.95 (br s, 1H), 4.66 (t, J=3.4 Hz, 1H), 4.06-3.76 (m, 4H), 3.69-3.48 (m, 2H), 2.07 (qt, J=6.0 Hz, 2H), 2.01-1.49 (m, 6H), 1.37 (s, 9H)

ESI-MS m/z 503 (M+H)+.

Step 3: Synthesis of 1-(3-tert-butyl-1H-pyrazol-5-yl)-N-[3-(tetrahydro-2H-pyran-2-yloxy)propyl]-7-(trifluoromethyl)imidazo[1,2-a]quinoxalin-4-amine

Step 4: Synthesis of 3-({1-[3-tert-butyl-1H-pyrazol-5-yl]-7-(trifluoromethyl)imidazo[1,2-a]quinoxalin-4-yl}amino)propan-1-ol

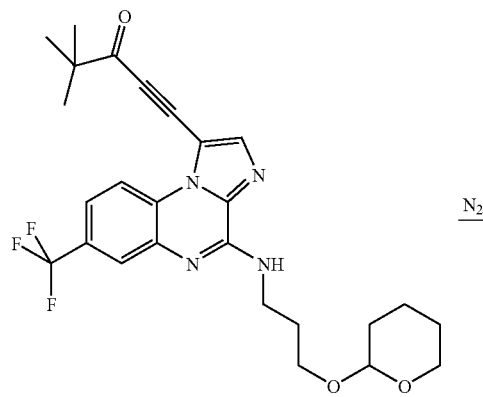

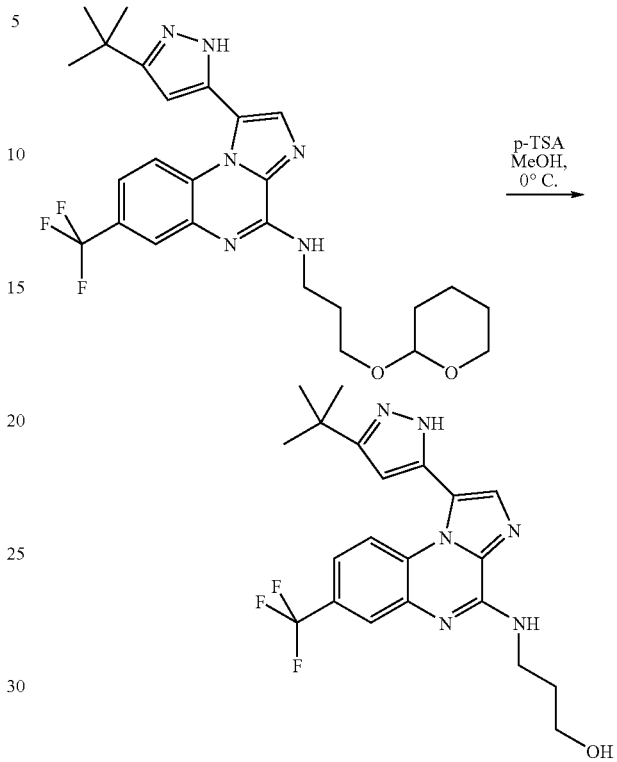

To a suspension of 1-{N-[3-(tetrahydro-2H-pyran-2-yloxy)propyl]-7-(trifluoromethyl)]imidazo[1,2-a]quinoxalin-1-yl}-4,4-dimethylpent-1-yn-3-one (13 mg, 0.025 mmol) in ethanol (1 mL) was added two drops of hydrazine hydrate. The mixture was stirred at room temperature under argon for 1 h and then concentrated in vacuo. The crude product was purified by preparative TLC (silica gel, dichloromethane/methanol 20/1) to afford the title compound (11 mg, 85%) as a gum.

¹H NMR (CDCl₃), δ (ppm): 7.97 (s, 1H), 7.73 (d, J=8.7 Hz, 1H), 7.56 (s, 1H), 7.23 (d, J=8.7 Hz, 1H), 6.85 (br s, 1H), 6.35 (s, 1H), 4.66 (t, J=3.4 Hz, 1H), 4.00-3.82 (m, 4H), 3.63-3.52 (m, 2H), 2.07 (qt, J=6.0 Hz, 2H), 1.98-1.55 (m, 6H), 1.42 (s, 9H)

ESI-MS m/z 517 (M+H)⁺.

General Procedure for THP Deprotection:
To a solution of tetrahydro-2H-pyran-2-yloxy substrate (1 eq) in methanol cooled at 0° C. was added para-toluenesulfonic acid (2.2 eq). The mixture was stirred at room temperature under argon for 3-5 h and then concentrated in vacuo. The residue is diluted in ethyl acetate and water. The aqueous layer is basified to pH 8 with a saturated aqueous solution of sodium hydrogencarbonate and extracted twice with ethyl acetate. The combined organic layers were dried over sodium sulfate, filtered and evaporated. The crude product was purified by preparative TLC (silica gel, mixture of dichloromethane/methanol) to afford the desired compound.

To a solution of 1-(3-tert-butyl-1H-pyrazol-5-yl)-N-[3-(tetrahydro-2H-pyran-2-yloxy)propyl]-7-(trifluoromethyl)imidazo[1,2-a]quinoxalin-4-amine (11 mg, 0.021 mmol) in methanol (0.2 mL) cooled at 0° C. was added para-toluenesulfonic acid (9 mg, 0.047 mmol). The mixture was stirred at room temperature under argon for 5 h and then concentrated in vacuo. The residue is diluted in ethyl acetate and water. The aqueous layer is basified to pH 8 with a saturated aqueous solution of sodium hydrogenocarbonate and extracted twice with ethyl acetate. The combined organic layers were dried over sodium sulfate, filtered and evaporated. The crude product was purified by preparative TLC (silica gel, dichloromethane/methanol 20/1) to afford the title compound (7 mg, 78%) as a colourless gum.

¹H NMR (CDCl₃), δ (ppm): 7.90 (s, 1H), 7.74 (d, J=8.6 Hz, 1H), 7.57 (s, 1H), 7.25 (d, J=8.8 Hz, 1H), 6.83 (br s, 1H), 6.35 (s, 1H), 3.89 (q, J=5.4 Hz, 2H), 3.71 (t, J=5.4 Hz, 2H), 1.90 (qt, J=5.4 Hz, 2H), 1.44 (s, 9H)

ESI-MS m/z 433 (M+H)⁺.

Example 37

3-({1-(3-hydroxy-1H-pyrazol-5-yl)-7-(trifluoromethyl)imidazo[1,2-a]quinoxalin-4-yl}amino)propan-1-ol

Step 1: Synthesis of 1-(3-morpholin-4-yl-3-oxoprop-1-yn-1-yl)-N-[3-(tetrahydro-2H-pyran-2-yloxy)propyl]-7-(trifluoromethyl)imidazo[1,2-a]quinoxalin-4-amine

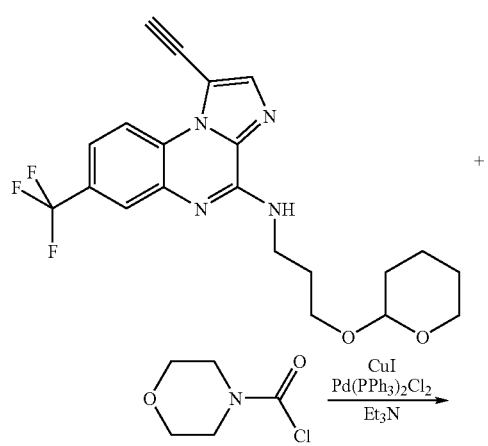

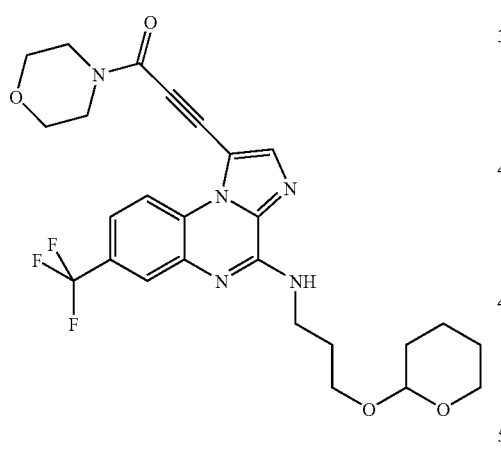

To a solution of 1-ethynyl-N-[3-(tetrahydro-2H-pyran-2-yloxy)propyl]-7-(trifluoromethyl)imidazo [1,2-a]quinoxalin-4-amine (46 mg, 0.11 mmol), copper iodide (1 mg, 0.0055 mmol), triphenylphosphine (3 mg, 0.11 mmol) and Pd(PPh$_3$)Cl$_2$ (1.5 mg, 0.0022 mmol) in anhydrous triethylamine (0.5 mL) was added morpholine-4-carbonyl chloride (17 µL, 0.16 mmol) under an argon atmosphere. The mixture was stirred at 80° C. for 40 h, poured onto water and extracted four times with ethyl acetate. The combined organic layers were dried over sodium sulfate, filtered and evaporated. The crude product was purified by preparative TLC (silica gel, dichloromethane/methanol 20/1) to afford the title compound (17 mg, 30%) as a yellow gum.

ESI-MS m/z 532 (M+H)$^+$.

Step 2: Synthesis of 1-(3-hydroxy-1H-pyrazol-5-yl)-N-[3-(tetrahydro-2H-pyran-2-yloxy)propyl]-7-(trifluoromethyl)imidazo[1,2-a]quinoxalin-4-amine

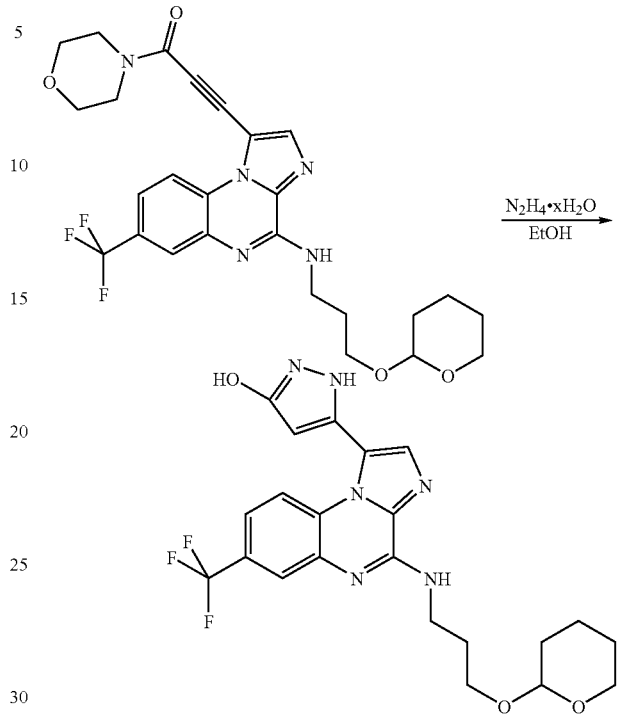

To a suspension of 1-(3-morpholin-4-yl-3-oxoprop-1-yn-1-yl)-N-[3-(tetrahydro-2H-pyran-2-yloxy)propyl]-7-(trifluoromethyl)imidazo[1,2-a]quinoxalin-4-amine (17 mg, 0.032 mmol) in ethanol (1 mL) was added two drops of hydrazine hydrate. The mixture was stirred at room temperature under argon for 1 h. As no cyclisation occurred, the mixture was then stirred at 70° C. for 65 h. After concentration in vacuo, the residue was poured onto water and extracted twice with ethyl acetate. The combined organic layers were dried over sodium sulfate, filtered and evaporated. The crude product was purified by preparative TLC (silica gel, dichloromethane/methanol 9/1) to afford the title compound (12 mg, 33%) as a white solid.

$^1$H NMR (CD$_3$OD), δ (ppm): 7.82 (s, 1H), 7.54 (br s, 2H), 7.25 (d, J=8.7 Hz, 1H), 5.78 (s, 1H), 4.56 (t, J=3.4 Hz, 1H), 3.88-3.70 (m, 4H), 3.55-3.45 (m, 2H), 1.97 (qt, J=6.0 Hz, 2H), 1.90-1.35 (m, 6H)

ESI-MS m/z 477 (M+H)$^+$.

Step 3: Synthesis of 3-({1-(3-hydroxy-1H-pyrazol-5-yl)-7-(trifluoromethyl)imidazo[1,2-a]quinoxalin-4-yl}amino)propan-1-ol

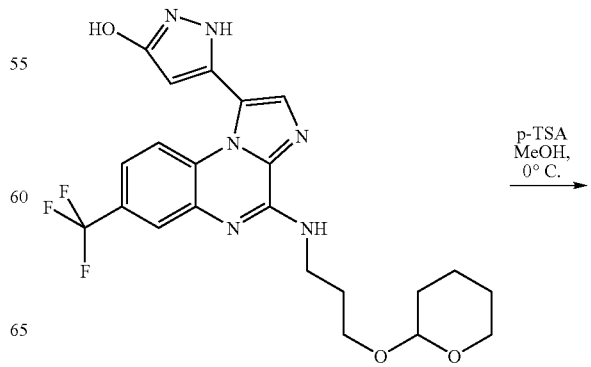

-continued

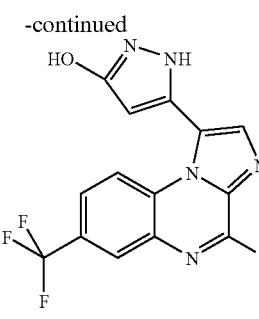

Prepared according to the general procedure for THP deprotection as described beforehand to give a white gum (50%).

¹H NMR (CD₃OD), δ (ppm): 7.92 (s, 1H), 7.65 (br s, 2H), 7.38 (d, J=8.7 Hz, 1H), 5.9 (br s, 1H), 6.35 (s, 1H), 3.83 (t, J=5.4 Hz, 2H), 3.77 (t, J=5.4 Hz, 2H), 2.01 (qt, J=5.4 Hz, 2H)
ESI-MS m/z 393 (M+H)⁺.

Example 38

3-({1-(4-chloro-1H-pyrazol-5-yl)-7-(trifluoromethyl)imidazo[1,2-a]quinoxalin-4-yl}amino)propan-1-ol Step 1: Synthesis of 1-bromo-N-[3-(tetrahydro-2H-pyran-2-yloxy)propyl]-7-(trifluoromethyl)imidazo[1,2-a]quinoxalin-4-amine

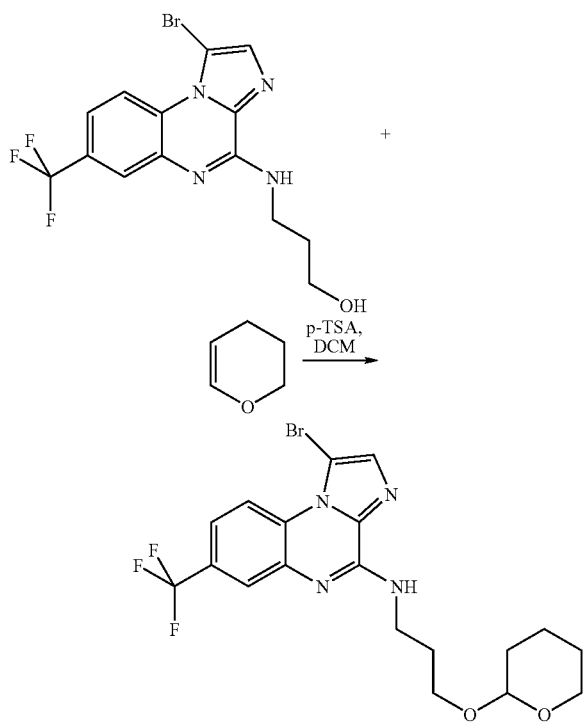

Prepared according to the general procedure for THP protection as described beforehand to give quantitatively an off-white solid.
ESI-MS m/z 473/475 (M+H)⁺.

Step 2: Synthesis of 3-{N-[3-(tetrahydro-2H-pyran-2-yloxy)propyl]-7-(trifluoromethyl)imidazo[1,2-a]quinoxalin-1-yl}prop-2-yn-1-ol

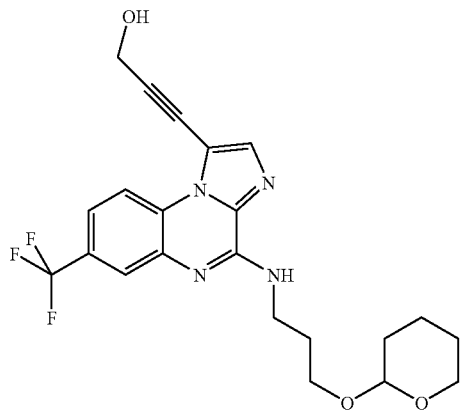

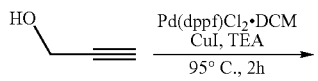

To a suspension of 1-bromo-N-[3-(tetrahydro-2H-pyran-2-yloxy)propyl]-7-(trifluoromethyl)imidazo[1,2-a]quinoxalin-4-amine (423 mg, 0.771 mmol), propargyl alcohol (112 µL, 1.93 mmol) and copper iodide (37 mg, 0.193 mmol) in anhydrous triethylamine (3.5 mL) degassed under argon for 10 minutes was added Pd(dppf)Cl₂.DCM (80 mg, 0.097 mmol). The mixture was stirred at 90° C. for 2 h and then allowed to cool to room temperature, poured onto a saturated aqueous solution of ammonium chloride and extracted three times with ethyl acetate/tetrahydrofuran (1:1). The combined organic layers were dried over sodium sulfate, filtered and evaporated. The crude product was purified by preparative TLC (silica gel, dichloromethane/methanol 20/1) to afford the title compound (305 mg, 88%) as a beige solid.

ESI-MS m/z 449 (M+H)⁺.

Step 3: Synthesis of 1-(chloroethynyl)-N-[3-(tetrahydro-2H-pyran-2-yloxy)propyl]-7-(trifluoromethyl)imidazo[1,2-a]quinoxalin-4-amine

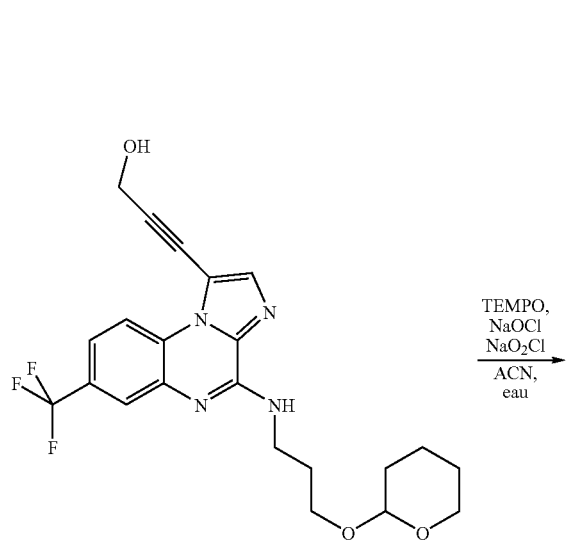

To a solution of 3-{N-[3-(tetrahydro-2H-pyran-2-yloxy)propyl]-7-(trifluoromethyl)imidazo[1,2-a]quinoxalin-1-yl}prop-2-yn-1-ol (60 mg, 0.134 mmol) in acetonitrile (2 mL) under argon was added a phosphate buffer solution (0.67M, 0.5 mL). The mixture was warmed to 35° C., TEMPO (2 mg, 0.010 mmol) was added, followed by the simultaneous addition of bleach NaOCl (2 mM, 376 µL, 0.188 mmol) and sodium chlorite NaO₂Cl (2 mM, 536 µL, 0.268 mmol). The reaction mixture was stirred at 35° C. for 2 h and then allowed to cool to room temperature, poured onto water, extracted three times with dichloromethane. The combined organic layers were dried over sodium sulfate, filtered and evaporated. The crude product was purified by preparative TLC (silica gel, dichloromethane/methanol 20/1) to afford the title compound (23 mg, 38%) as a white solid.

¹H NMR (CDCl₃), δ (ppm): 8.85 (d, J=8.7 Hz, 1H), 8.03 (s, 1H), 7.76 (s, 1H), 7.51 (d, J=8.9 Hz, 1H), 6.84 (br s, 1H), 4.65 (t, J=3.4 Hz, 1H), 4.01-3.80 (m, 4H), 3.64-3.52 (m, 2H), 2.06 (qt, J=6.0 Hz, 2H), 1.98-1.56 (m, 6H)

ESI-MS m/z 453/455 (M+H)⁺.

Step 4: Synthesis of 1-(chloroethynyl)-N-[3-(tetrahydro-2H-pyran-2-yloxy)propyl]-7-(trifluoromethyl)imidazo[1,2-a]quinoxalin-4-amine

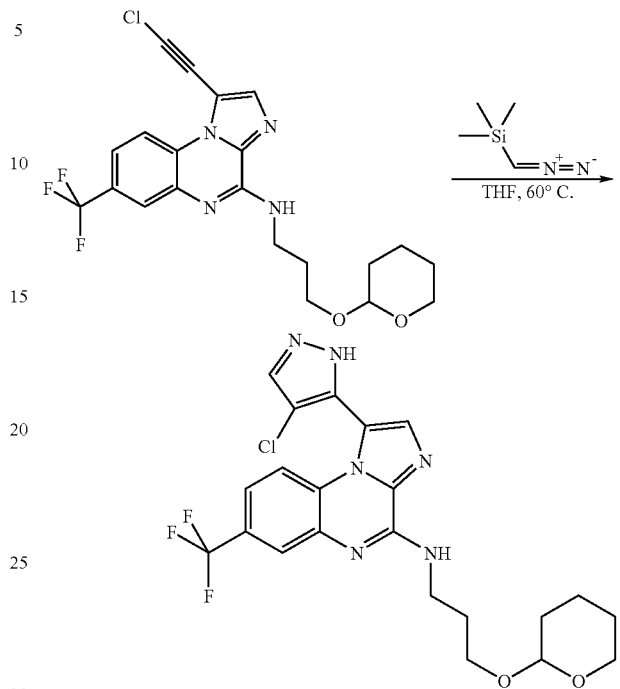

To a solution of 1-{7-(trifluoromethyl)-4-[(3-hydroxypropyl)amino]imidazo[1,2-a]quinoxalin-1-yl}-4,4-dimethylpent-1-yn-3-one (23 mg, 0.05 mmol) in anhydrous tetrahydrofuran (1 mL) was added TMS-diazomethane (2M in THF, 91 µL, 0.183 mmol). The mixture was stirred at 60° C. under argon for 6 h and then at room temperature overnight. The reaction mixture was treated with a saturated aqueous solution of ammonium chloride and extracted twice with dichloromethane. The combined organic layers were dried over sodium sulfate, filtered and evaporated. The crude product was purified by preparative TLC (silica gel, dichloromethane/methanol 20/1) to afford the title compound (12 mg, 48%) as a yellow oil.

¹H NMR (CD₃OD), δ (ppm): 8.12 (br s, 1H), 8.00 (s, 1H), 7.73 (s, 1H), 7.50 (br s, 1H), 7.36 (d, J=8.0 Hz, 1H), 4.70 (t, J=3.4 Hz, 1H), 4.03-3.86 (m, 4H), 3.63-3.51 (m, 2H), 2.13 (qt, J=5.4 Hz, 2H), 2.01-1.51 (m, 6H)

ESI-MS m/z 495/497 (M+H)⁺.

Step 5: Synthesis of 3-({1-(4-chloro-1H-pyrazol-5-yl)-7-(trifluoromethyl)imidazo[1,2-a]quinoxalin-4-yl}amino)propan-1-ol

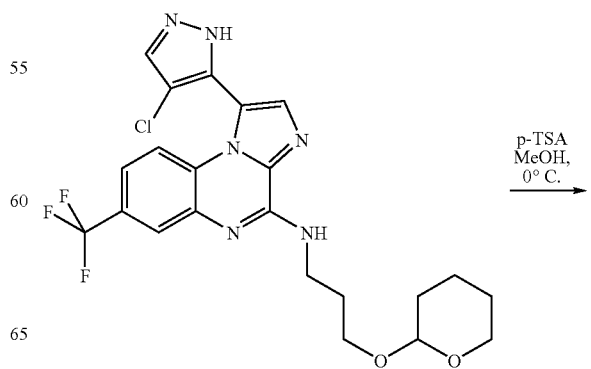

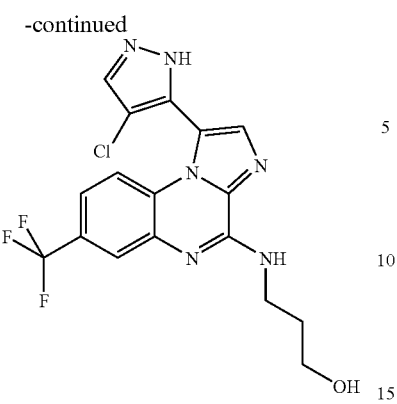

Prepared according to the general procedure for THP protection as described beforehand to give a white solid (60%).
$^1$H NMR (CD$_3$OD), δ (ppm): 8.12 (br s, 1H), 7.99 (s, 1H), 7.75 (s, 1H), 7.51 (br s, 1H), 7.38 (d, J=8.4 Hz, 1H), 3.88 (t, J=6.4 Hz, 2H), 3.81 (t, J=6.4 Hz, 2H), 2.06 (qt, J=6.4 Hz, 2H)
ESI-MS m/z 411/413 (M+H)$^+$.

Example 39

3-({1-[3-methyl-1H-pyrazol-5-yl]-7-(trifluoromethyl)imidazo[1,2-a]quinoxalin-4-yl}amino)propan-1-ol Step 1: Synthesis of 1-[2-(trimethylsilyl)ethoxymethyl]-3-methyl-pyrazole

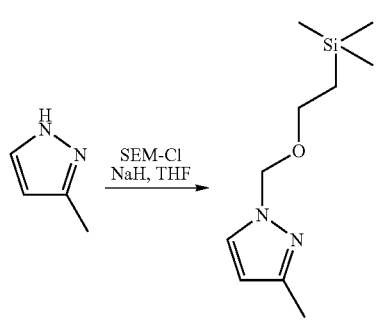

General Procedure for SEM Protection:

To a solution of sodium hydride (60% in oil, 1 eq) in anhydrous tetrahydrofuran, cooled at 0° C., were added pyrazole (1 eq) and 2-trimethylsilyl)ethoxymethyl chloride (1 eq) under an argon atmosphere. The mixture was stirred at room temperature overnight and then poured onto a saturated aqueous solution of sodium hydrogencarbonate. After concentration in vacuo, the residue is diluted in ethyl acetate and water. The organic phase was separated and the aqueous phase was extracted again with ethyl acetate. The combined organic layers were dried over sodium sulfate, filtered and evaporated. The crude product was purified by flash chromatography (silica gel, mixture of dichloromethane/methanol) to afford the desired compound.

To a solution of sodium hydride (60% in oil, 80 mg, 2 mmol) in anhydrous tetrahydrofuran (5 mL), cooled at 0° C., were added 3-methyl-pyrazole (160 μL, 2 mmol) and 2-trimethylsilyl)ethoxymethyl chloride (354 μL, 2 mmol) under an argon atmosphere. The mixture was stirred at room temperature overnight and then poured onto a saturated aqueous solution of sodium hydrogencarbonate. After concentration in vacuo, the residue is diluted in ethyl acetate and water. The organic phase was separated and the aqueous phase was extracted again with ethyl acetate. The combined organic layers were dried over sodium sulfate, filtered and evaporated. The crude product was purified by flash chromatography (silica gel, dichloromethane/methanol 20/1) to afford the title compound (219 mg) as a colorless oil in mixture with its regioisomer.
ESI-MS m/z 213 (M+H)$^+$.

Step 2: Synthesis of 1-[2-(trimethylsilyl)ethoxymethyl]-3-methyl-pyrazole-5-boronic acid

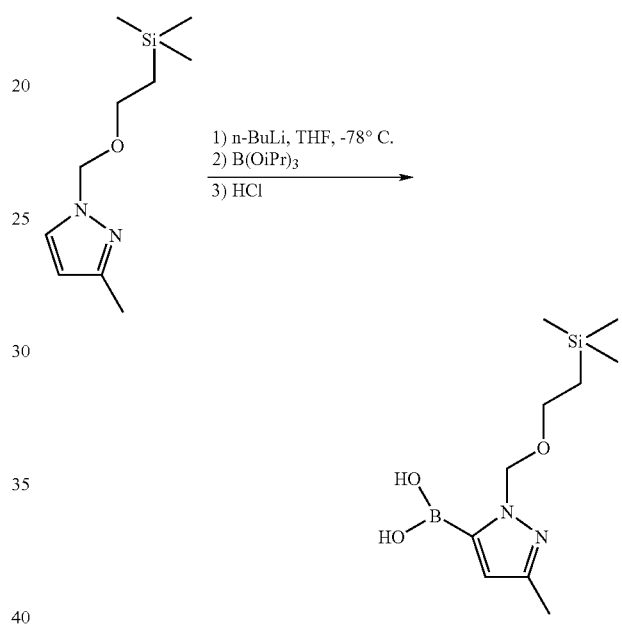

General Procedure for Boronic Acid Formation:

To a solution of 1-[2-(trimethylsilyl)ethoxymethyl]-pyrazole (1 eq) in anhydrous tetrahydrofuran, cooled at −78° C., was added n-butyllithium (3 eq) under an argon atmosphere. The mixture was stirred for 30 minutes and then was added triisopropyl borate (6 eq). The mixture was allowed to cool to room temperature in 2 h and then was slowly hydrolysed with HCl 1M to pH 6. The aqueous layer was extracted twice with ethyl acetate. The combined organic layers were washed with water, brine, dried over sodium sulfate, filtered and evaporated to afford the desired compound in mixture with unreacted starting material.

To a solution of 1-[2-(trimethylsilyl)ethoxymethyl]-3-methyl-pyrazole (90 mg, 0.42 mmol) in anhydrous tetrahydrofuran (2 mL), cooled at −78° C., was added n-butyllithium (2.3 M, 553 μL, 1.27 mmol) under an argon atmosphere. The mixture was stirred for 30 minutes and then was added triisopropyl borate (0.58 mL, 2.52 mmol). The mixture was allowed to cool to room temperature in 2 h and then was slowly hydrolysed with HCl 1M to pH 6. The aqueous layer was extracted twice with ethyl acetate. The combined organic layers were washed with water, brine, dried over sodium sulfate, filtered and evaporated to afford the title compound (120 mg) in mixture with unreacted starting material, used without further purification.
ESI-MS m/z 257 (M+H)$^+$.

Step 3: Synthesis of 3-({1-[2-(trimethylsily) ethoxymethyl]-3-methyl-pyrazol-5-yl]-7-(trifluoromethyl)imidazo[1,2-a]quinoxalin-4-yl}amino)propan-1-ol

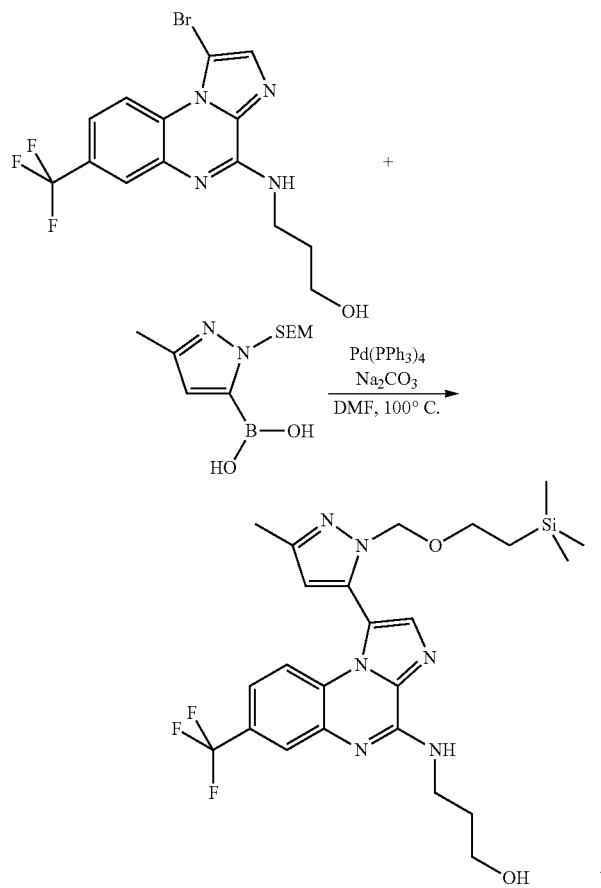

General Procedure for Suzuki Coupling of Substituted Pyrazole Boronic Acid:

To a suspension of 3-(1-bromo-7-trifluoromethyl-imidazo[1,2-a]quinoxalin-4-ylamino)-propan-1-ol (1 eq), 1-[2-(trimethylsilyl)ethoxymethyl]-pyrazole-5-boronic acid (2 eq) and sodium carbonate (3 eq) in N,N-dimethylformamide degassed under argon for 10 minutes was added tetrakis(triphenylphosphine)palladium (0.3 eq). The mixture was allowed to stir for 3 hours at 100° C. The crude mixture is cooled to room temperature, diluted with ethyl acetate and a saturated aqueous solution of sodium hydrogencarbonate. The organic phase was separated and the aqueous phase was extracted again twice with ethyl acetate. The combined organic layers were washed with brine, dried over sodium sulfate, filtered and evaporated. The crude product was purified by preparative TLC (silica gel, mixture of dichloromethane/methanol) to afford the desired compound.

To a suspension of 3-(1-bromo-7-trifluoromethyl-imidazo[1,2-a]quinoxalin-4-ylamino)-propan-1-ol (27 mg, 0.07 mmol), 1-[2-(trimethylsilyl)ethoxymethyl]-pyrazole-5-boronic acid (36 mg, 0.14 mmol) and sodium carbonate (22 mg, 0.21 mmol) in N,N-dimethylformamide (300 µL) degassed under argon for 10 minutes was added tetrakis(triphenylphosphine)palladium (24 mg, 0.021 mmol). The mixture was allowed to stir for 3 hours at 100° C. The crude mixture is cooled to room temperature, diluted with ethyl acetate and a saturated aqueous solution of sodium hydrogencarbonate. The organic phase was separated and the aqueous phase was extracted again twice with ethyl acetate. The combined organic layers were washed with brine, dried over sodium sulfate, filtered and evaporated. The crude product was purified by preparative TLC (silica gel, dichloromethane/methanol 20/1) to afford the title compound (10 mg, 28%) as a colorless gum.

$^1$H NMR (CD$_3$OD), δ (ppm): 7.98 (d, J=1.8 Hz, 1H), 7.73 (s, 1H), 7.34 (dd, J=1.8, 8.7 Hz, 1H), 7.25 (d, J=8.8 z, 1H), 6.66 (s, 1H), 5.24 (s, 2H), 3.86 (t, J=6.8 Hz, 2H), 3.80 (t, J=6.3 Hz, 2H), 3.46 (t, J=7.7 Hz, 2H), 2.47 (s, 3H), 2.05 (qt, J=6.4 Hz, 2H), 0.46 (t, J=8.0 Hz, 2H), −0.10 (s, 9H)

ESI-MS m/z 521 (M+H)$^+$.

Step 4: Synthesis of 3-{[1-(3-methyl-1H-pyrazol-5-yl)-7-(trifluoromethyl)imidazo[1,2-a]quinoxalin-4-yl]amino}propan-1-ol

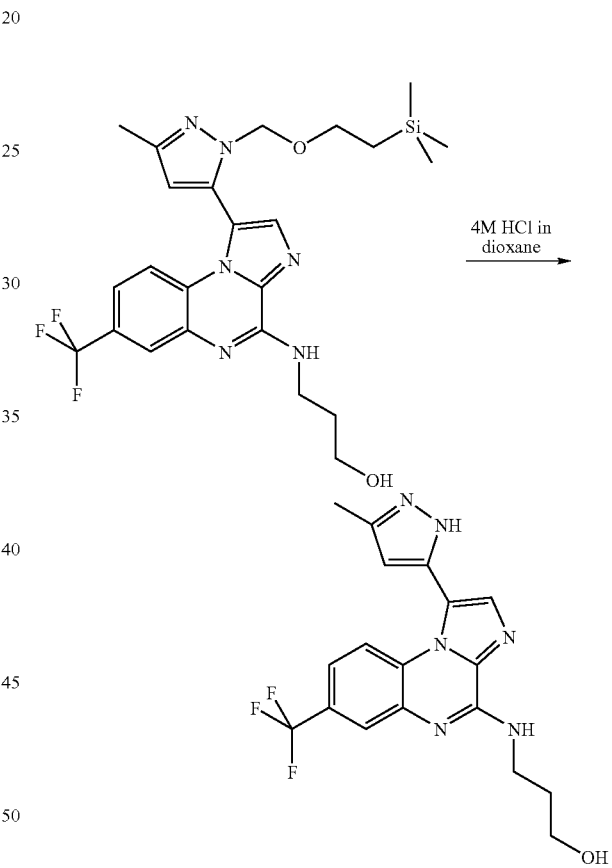

General Procedure for SEM Deprotection:

A solution of 1-[2-(trimethylsilyl)ethoxymethyl]-pyrazole (1 eq) in 4M HCl in dioxane (100 eq) was stirred at room temperature overnight. The residue is diluted in ethyl acetate, quenched with a saturated aqueous solution of sodium hydrogencarbonate and extracted three times with ethyl acetate. The combined organic layers were dried over sodium sulfate, filtered and evaporated. The crude product was purified by preparative TLC (silica gel, mixture of dichloromethane/methanol) to afford the desired compound.

A solution of 3-({1-[2-(trimethylsilyl)ethoxymethyl]-3-methyl-pyrazol-5-yl]-7-(trifluoromethyl)imidazo[1,2-a]quinoxalin-4-yl}amino)propan-1-ol (10 mg, 0.0192 mmol) in 4M HCl in dioxane (0.5 mL) was stirred at room temperature overnight. The residue is diluted in ethyl acetate, quenched with a saturated aqueous solution of sodium hydrogencarbonate and extracted three times with ethyl acetate. The combined organic layers were dried over sodium sulfate, filtered and evaporated. The crude product was purified by preparative TLC (silica gel, dichloromethane/methanol 20/1) to afford the title compound (4 mg, 53%) as a white solid.

$^1$H NMR (CD$_3$OD), δ (ppm): 7.97 (s, 1H), 7.82-7.72 (m, 1H), 7.65 (s, 1H), 7.36 (d, J=8.8 Hz, 1H), 6.48 (s, 1H), 3.86 (t, J=6.6 Hz, 2H), 3.80 (t, J=6.2 Hz, 2H), 2.51 (s, 3H), 2.05 (qt, J=6.4 Hz, 2H)

ESI-MS m/z 391 (M+H)$^+$.

Example 40

3-({1-[4-methyl-1H-pyrazol-5-yl]-7-(trifluoromethyl)imidazo[1,2-a]quinoxalin-4-yl}amino)propan-1-ol

Step 1: Synthesis of 1-[2-(trimethylsily)ethoxymethyl]-4-methyl-pyrazole

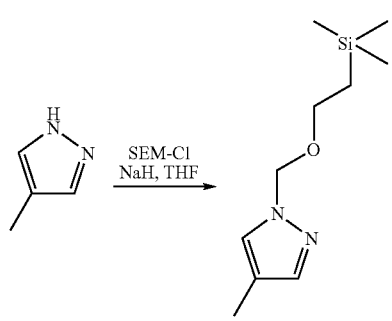

Prepared according to the general procedure for SEM protection as described beforehand to give quantitatively a colorless oil.

ESI-MS m/z 213 (M+H)$^+$.

Step 2: Synthesis of 1-[2-(trimethylsily)ethoxymethyl]-4-methyl-pyrazole-5-boronic acid

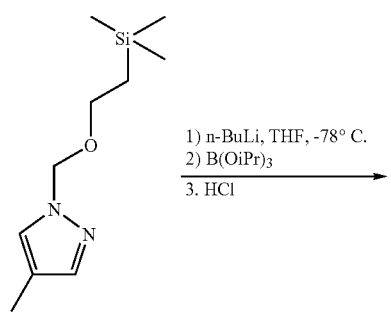

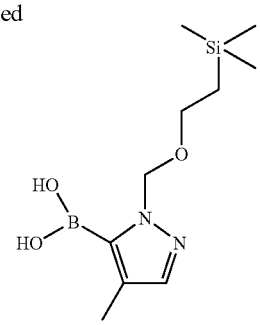

Prepared according to the general procedure for boronic acid formation as described beforehand to give a colorless oil, in mixture with unreacted starting material, used without further purification.

ESI-MS m/z 257 (M+H)$^+$.

Step 3: Synthesis of 3-({1-[2-(trimethylsilyl)ethoxymethyl]-4-methyl-pyrazol-5-yl]-7-(trifluoromethyl)imidazo[1,2-a]quinoxalin-4-yl}amino)propan-1-ol

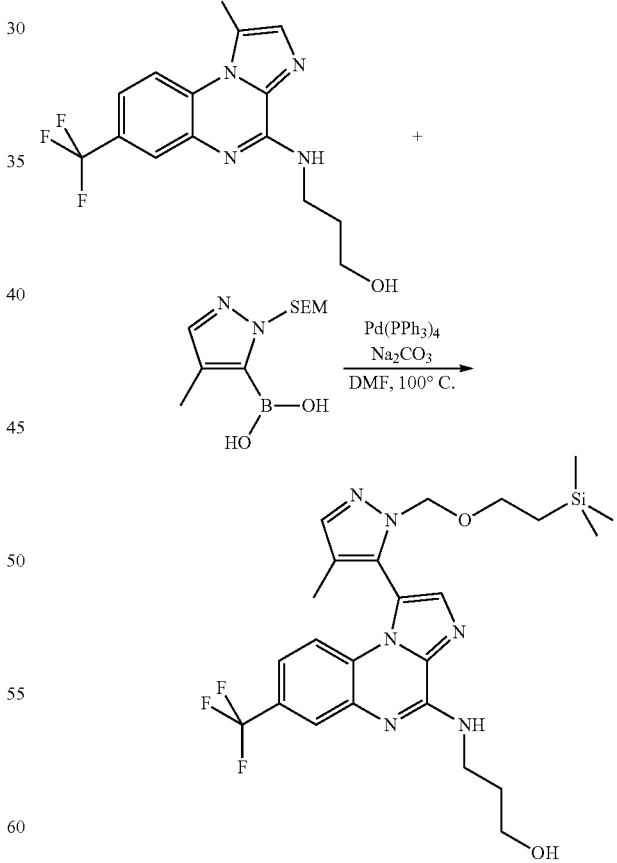

Prepared according to the general procedure for Suzuki coupling with pyrazole boronic acid as described beforehand to afford the title compound (60 mg, 60%) as a colorless gum.

ESI-MS m/z 521 (M+H)$^+$.

Step 4: Synthesis of 3-{[1-(4-methyl-1H-pyrazol-5-yl)-7-(trifluoromethyl)imidazo[1,2-a]quinoxalin-4-yl]amino}propan-1-ol

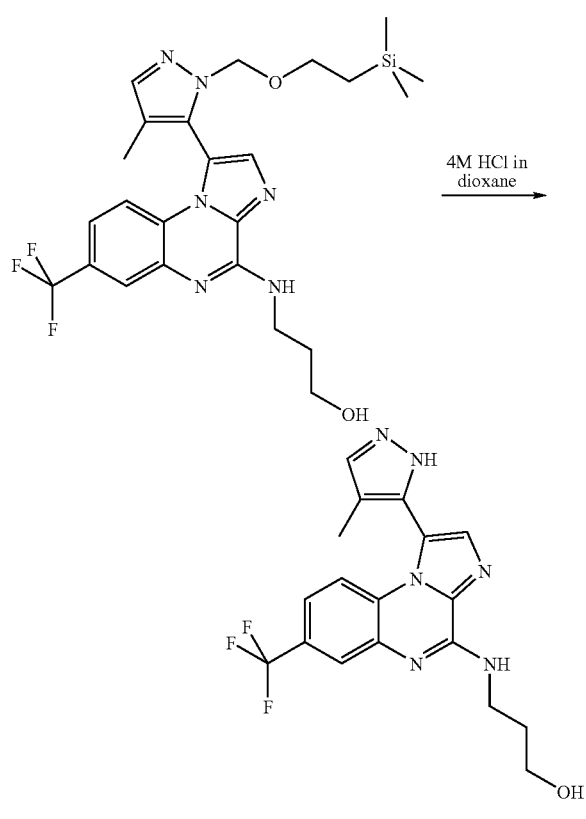

Prepared according to the general procedure for SEM deprotection acid as described beforehand to afford the title compound (1.1 mg, 2%) as a white solid.

$^1$H NMR (CD$_3$OD), δ (ppm): 7.98 (s, 1H), 7.81 (s, 1H), 7.68 (s, 1H), 7.40 (d, J=8.6 Hz, 1H), 7.33 (d, J=8.6 Hz, 1H), 3.88 (t, J=7.0 Hz, 2H), 3.81 (t, J=6.5 Hz, 2H), 2.06 (qt, J=6.3 Hz, 2H), 2.04 (s, 3H)

ESI-MS m/z 391 (M+H)$^+$.

Example 41

4-[(3-hydroxypropyl)amino]-7-(trifluoromethyl)imidazo[1,2-a]quinoxaline-1-carbaldehyde

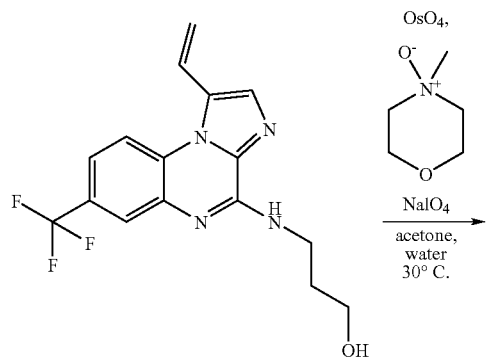

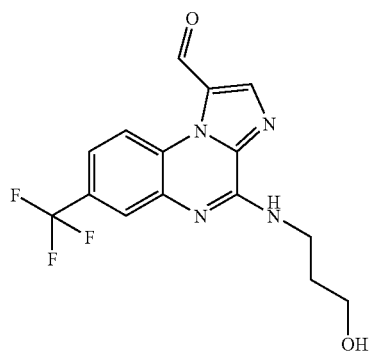

To a suspension of 3-{[7-(trifluoromethyl)-1-vinylimidazo[1,2-a]quinoxalin-4-yl]amino}propan-1-ol (33 mg, 0.099 mmol) in acetone-water (9:1, 1 mL), was added osmium tetroxide (2.5% wt. in t-BuOH, 53 mg, 0.05 mmol) and 4-methylmorpholine 4-oxide (25 mg, 0.20 mmol). The reaction mixture was stirred for 4 days at 30° C. under argon, and then a suspension of sodium periodate (85 mg, 0.40 mmol) in water (500 µL) was added. The mixture was stirred for one day at 30° C. under argon. Then it was filtered, washed with an aqueous saturated solution of Na$_2$SO$_3$ and extracted with ethyl acetate. The combined organic phases were dried over Na$_2$SO$_4$, concentrated in vacuo, filtered, concentrated to give, after purification by preparative TLC (dichloromethane/methanol 9/1), the title compound (24 mg, 70%) as a pale yellow solid.

$^1$H NMR (CDCl$_3$), δ (ppm): 9.99 (s, 1H), 9.44 (d, J=8.8 Hz, 1H), 8.32 (s, 1H), 7.99 (s, 1H), 7.59 (d, J=8.8 Hz, 1H), 6.80 (br s, 1H), 3.91 (q, J=6.1 Hz, 2H), 3.74 (t, J=5.3 Hz, 2H), 1.95 (qt, J=6.4 Hz, 2H)

ESI-MS m/z 339 (M+H)$^+$

Example 42

3-{[1-(hydroxymethyl)-7-(trifluoromethyl)imidazo[1,2-a]quinoxalin-4-yl]amino}propan-1-ol

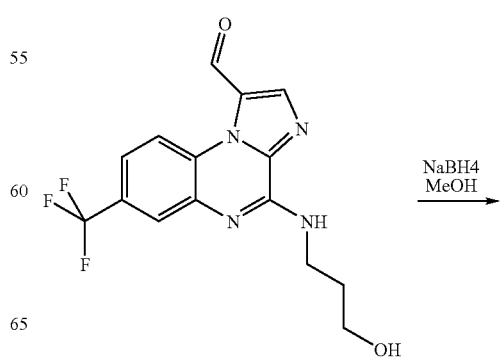

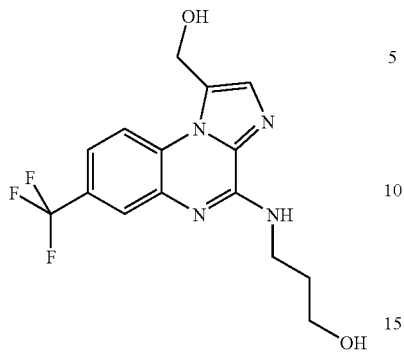

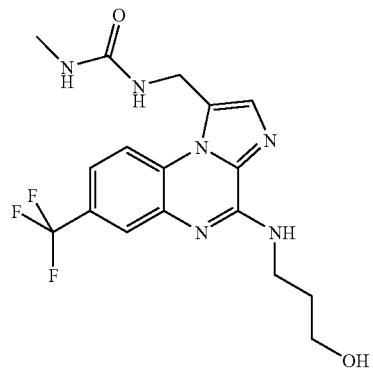

To a solution of the 4-[(3-hydroxypropyl)amino]-7-(trifluoromethyl)imidazo[1,2-a]quinoxaline-1-carbaldehyde prepared as in example 36 (8 mg, 0.024 mmol) in anhydrous methanol (300 µL), cooled at 0° C. was added sodium borohydride (2 mg, 0.047 mmol). The mixture was allowed to warm to room temperature over 1 h under argon and then diluted with water and extracted three times with ethyl acetate. The combined organic layers were dried over sodium sulfate, filtered and evaporated. The crude product was purified by preparative TLC (silica gel, dichloromethane/methanol 9/1) to afford the title compound as a white solid (5 mg, 61%).

$^1$H NMR (CD$_3$OD). δ (ppm): 8.49 (d, J=8.7 Hz, 1H), 7.92 (s, 1H), 7.57-7.54 (m, 2H), 5.09 (s, 2H), 3.77 (t, J=6.7 Hz, 2H), 3.72 (t, J=6.1 Hz, 2H), 1.96 (qt, J=6.3 Hz, 2H)

ESI-MS m/z 341 (M+H)$^+$

To a solution of 4-[(3-hydroxypropyl)amino]-7-(trifluoromethyl)imidazo[1,2-a]quinoxaline-1-carbaldehyde (35 mg, 0.10 mmol) in anhydrous tetrahydrofuran (190 µL) under Argon were added titanium(IV) isopropoxide (50 µL, 0.17 mmol) and N-methylurea (9 mg, 0.11 mmol). After 5 h at room temperature, sodium borohydride (2.2 mg, 0.05 mmol) was added at 0° C. and the solution was stirred at 35° C. overnight. The mixture was allowed to cool to room temperature, quenched with water (formation of a precipitate) and concentrated. The residue was triturated in ethyl acetate and water, filtrated and rinsed with ethyl acetate and water. The filtrate was washed with a saturated aqueous solution of ammonium chloride and extracted twice with ethyl acetate. The combined organic layers were dried over sodium sulfate, filtered and evaporated. The crude product was purified by preparative TLC (silica gel, dichloromethane/methanol 9/1) to afford the title compound (27 mg, 69%) as a pale yellow solid.

$^1$H NMR (CD$_3$OD), δ (ppm): 8.17 (d, J=9.2 Hz, 1H), 7.93 (s, 1H), 7.55 (d, J=9.2 Hz, 1H), 7.52 (s, 1H), 4.96 (s, 2H), 3.78 (t, J=6.8 Hz, 2H), 3.72 (t, J=6.0 Hz, 2H), 2.74 (s, 3H), 1.96 (qt, J=6.4 Hz, 2H).

ESI-MS m/z 397 (M+H)$^+$.

Example 43

1-({4-[(3-hydroxypropyl)amino]-7-(trifluoromethyl)imidazo[1,2-a]quinoxalin-1-yl}methyl)-3-methylurea

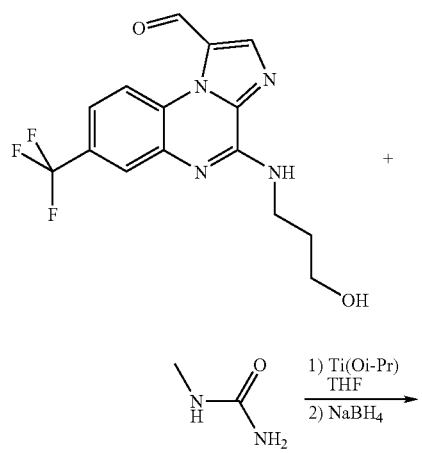

Example 44

3-({1-[(benzylamino)methyl]-7-(trifluoromethyl)imidazo[1,2-a]quinoxalin-4-yl}amino)propan-1-ol

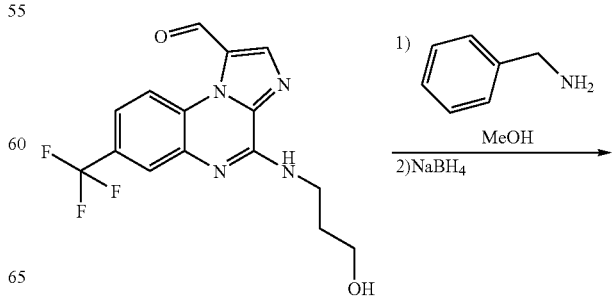

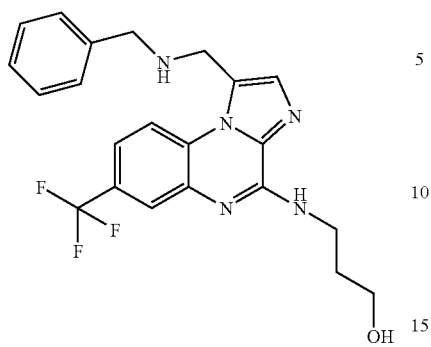

To a solution of the benzylamine (13 μL, 0.12 mmol) in methanol (400 μL) was added 4-[(3-hydroxypropyl)amino]-7-(trifluoromethyl)imidazo[1,2-a]quinoxaline-1-carbaldehyde (35 mg, 0.10 mmol). The reaction mixture was stirred at 30° C. for 17 h. After addition of NaBH$_4$ (5 mg, 0.12 mmol), the mixture was stirred at 30° C. for 5 h. Then it was concentrated, diluted in ethyl acetate, washed with an aqueous saturated solution of ammonium chloride and extracted with ethyl acetate. The combined organic phases were dried over Na$_2$SO$_4$, filtered, concentrated in vacuo to give, after purification by preparative TLC (dichloromethane/methanol 9/1), the title compound (32 mg, 75%) as a colorless oil.

$^1$H NMR (CD$_3$OD), δ (ppm): 8.10 (d, J=8.8 Hz, 1H), 7.73 (s, 1H), 7.34 (s, 1H), 7.30-7.17 (m, 6H), 4.12 (s, 2H), 3.84 (s, 2H), 3.67-3.63 (m, 4H), 1.88 (qt, J=6.4 Hz, 2H)

EI-MS m/z 430 (M+H)$^+$.

To a solution of 3-({1-[(benzylamino)methyl]-7-(trifluoromethyl)imidazo[1,2-a]quinoxalin-4-yl}amino)propan-1-ol (23 mg, 0.05 mmol) in methanol (600 μL) were added 5% Pd/C (21 mg, 0.01 mmol) and para-toluenesulfonic acid (2 mg, 0.01 mmol). The mixture was stirred under one hydrogen atmosphere for 4 days at room temperature. The reaction mixture was filtered on Celite and rinsed with methanol and dichloromethane. The crude product was purified by preparative TLC (dichloromethane/methanol 9/1) to give the title compound (8 mg, 43%) as a colorless oil.

$^1$H NMR (DMSO-d$_6$), δ (ppm): 8.41 (d, J=8.8 Hz, 1H), 7.96 (t, J=6.4 Hz, 1H), 7.83 (s, 1H), 7.56-7.52 (m, 2H), 4.91 (s, 1H), 4.64-4.61 (m, 2H), 4.44 (s, 2H), 3.62 (q, J=6.8 Hz, 2H), 3.53 (q, J=6.0 Hz, 2H), 1.82 (qt, J=6.4 Hz, 2H).

EI-MS m/z 340 (M+H)$^+$.

Example 45

3-{[1-(aminomethyl)-7-(trifluoromethyl)imidazo[1,2-a]quinoxalin-4-yl]amino}propan-1-ol Example 46

3-{[1-(1H-imidazol-2-yl)-7-(trifluoromethyl)imidazo[1,2-a]quinoxalin-4-yl]amino}propan-1-ol

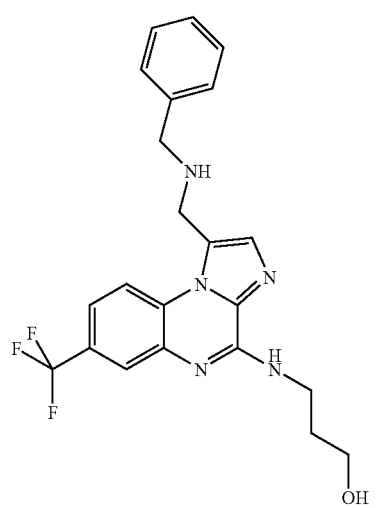

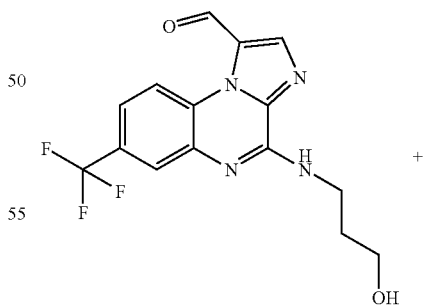

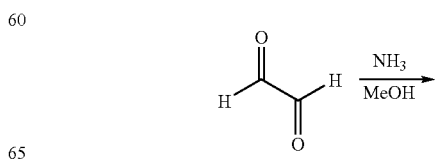

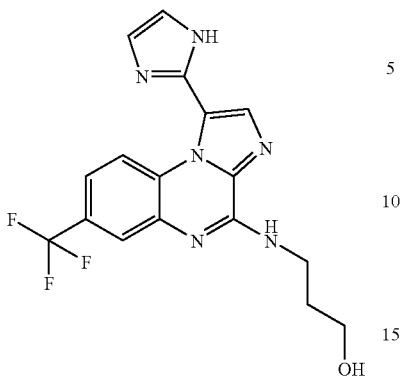

To a solution of 4-[(3-hydroxypropyl)amino]-7-(trifluoromethyl)imidazo[1,2-a]quinoxalin-1-carbaldehyde (35 mg, 0.10 mmol) in methanol (1.2 mL) was added glyoxal (40% in water, 15 μL, 0.10 mmol). The mixture was cooled at 0° C. and NH₃ (2M in ethanol, 150 μL, 0.30 mmol) was added. The reaction was stirred at 25° C. under argon overnight. The reaction was followed by TLC that showed small conversion of the starting material in imidazole. The addition of reactants was repeated 4 times in 4 days, until the TLC indicated completion of the reaction. The reaction was concentrated. The crude product was purified twice by preparative TLC (dichloromethane/methanol 9/1) to give the title compound (7 mg, 18%) as a beige powder.

¹H NMR (DMSO-d₆), δ (ppm): 8.11 (t, J=6.0 Hz, 1H), 7.98 (d, J=8.4 Hz, 1H), 7.86 (s, 1H), 7.84 (s, 1H), 7.41 (m, 3H), 4.64 (t, J=6.0 Hz, 1H), 3.66 (q, J=6.4 Hz, 2H), 3.55 (q, J=6.0 Hz, 2H), 1.86 (qt, J=6.4 Hz, 2H).

EI-MS m/z 377 (M+H)⁺.

Example 47

5-{4-[(3-hydroxypropyl)amino]-7-(trifluoromethyl)imidazo[1,2-a]quinoxalin-1-yl}-1H-pyrazole-3-carboxylic acid Step 1: 5-[4-(3-Hydroxy-propylamino)-7-trifluoromethyl-imidazo[1,2-a]quinoxalin-1-yl]-1H-pyrazole-3-carboxylic acid ethyl ester

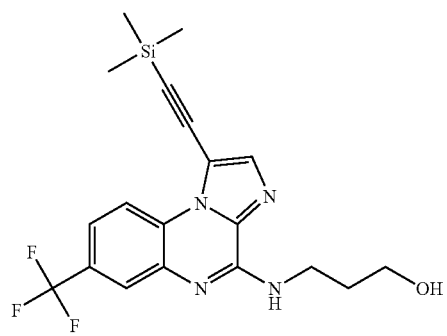

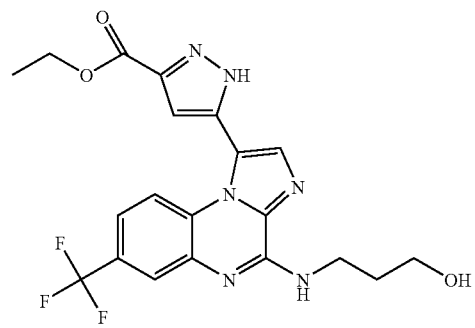

A mixture of 3-(7-Trifluoromethyl-1-trimethylsilanylethynyl-imidazo[1,2-a]quinoxalin-4-ylamino)-propan-1-ol (0.37 mmol; 150 mg), ethyl diazoacetate (0.93 mmol; 0.10 mL), and CsF (0.55 mmol; 84 mg), in THF (0.2 mL) under argon was stirred at 85° C. for 20 hr. After concentration in vacuo, the residue was purified by preparative TLC (dichloromethane/methanol) to yield the title compound as a white powder (58 mg; 0.13 mmol; 35%).

ESI-MS m/z 449 (M+H)⁺

¹H NMR (CDCl₃), δ (ppm): 7.95 (s, 1H); 7.68 (d, 1H, J=8.3 Hz); 7.64 (s, 1H); 7.29 (d, 1H, J=9.4 Hz); 7.13 (s, 1H); 6.72 (t, 1H, J=6.4 Hz); 4.49 (q, 2H, J=7.3 Hz); 3.92 (q, 2H, J=5.6 Hz); 3.72 (t, 2H, J=7.0 Hz); 1.93 (qt, 2H, J=5.6 Hz); 1.47 (t, 3H, J=7.0 Hz).

Example 48

5-{4-[(3-hydroxypropyl)amino]-7-(trifluoromethyl)imidazo[1,2-a]quinoxalin-1-yl}-1H-pyrazole-3-carboxylic acid

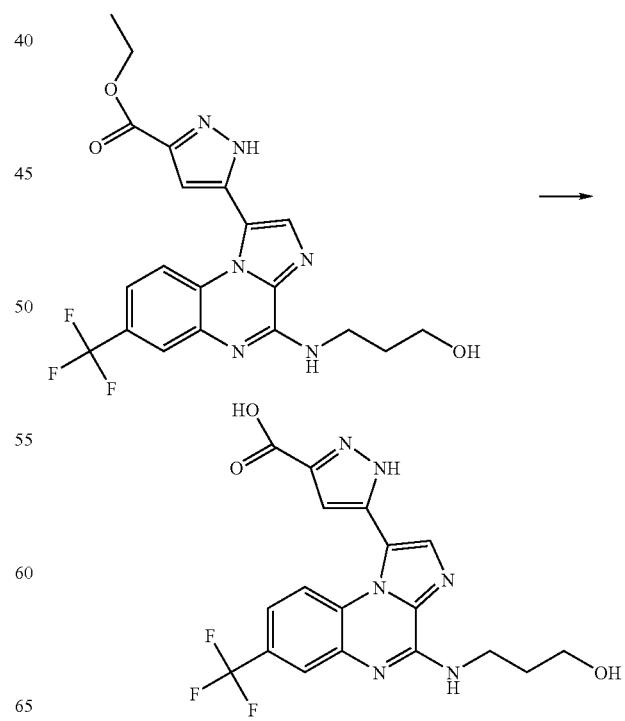

A solution of 5-[4-(3-Hydroxy-propylamino)-7-trifluoromethyl-imidazo[1,2-a]quinoxalin-1-yl]-1H-pyrazole-3-carboxylic acid ethyl ester (0.12 mmol; 54 mg), LiOH (0.13 mmol; 3 mg), in THF/H₂O (0.2+0.1 mL), was stirred at 40° C. overnight. Further LiOH (0.26 mmol; 6 mg) was added, and the reaction was continued at 50° C. another 24 hr. Concentration, and washing with water affords the title compound, as a white solid, lithium salt (51 mg; 0.12 mmol; 100%).

ESI-MS m/z 421 (M+H)⁺

¹H NMR (MeOD), δ (ppm): 7.85 (s, 1H); 7.68 (d, 1H, J=8.6 Hz); 7.49 (s, 1H); 7.16 (d, 1H, J=9.1 Hz); 6.79 (s, 1H); 3.79 (t, 2H, J=6.7 Hz); 3.73 (t, 2H, J=6.1 Hz); 1.98 (qt, 2H, J=6.4 Hz)

Example 49

3-({1-[3-(hydroxymethyl)-1H-pyrazol-5-yl]-7(trifluoromethyl)imidazo[1,2-a]quinoxalin-4-yl}amino)propan-1-ol

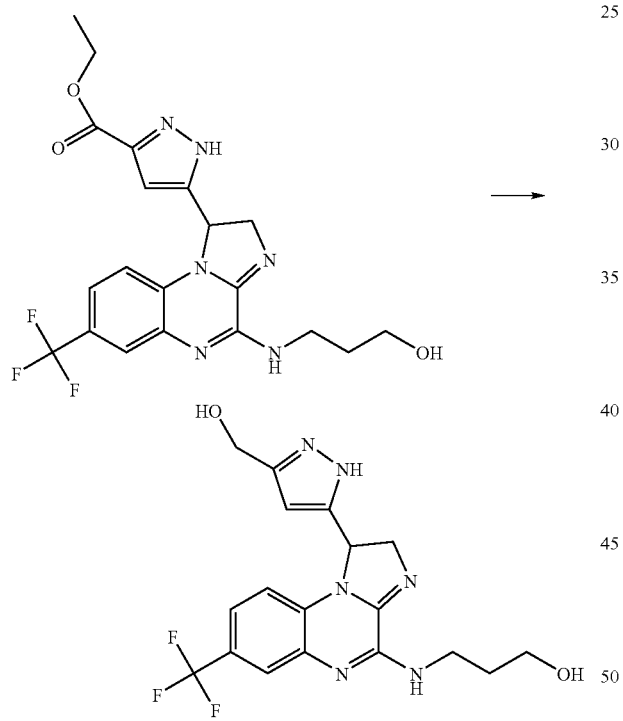

To a solution of 5-[4-(3-Hydroxy-propylamino)-7-trifluoromethyl-imidazo[1,2-a]quinoxalin-1-yl]-1H-pyrazole-3-carboxylic acid ethyl ester (0.08 mmol; 36 mg), in THF (0.2 mL) under argon cooled to 0° C., was added LAH (0.24 mmol; 10 mg). The reaction was slowly warmed up to room temperature over 4 hr, then to 45° C. overnight. After addition of dioxane (1 mL), the mixture was heated to 75° C. for 24 hr. After quenching with Rochelle's salt, the mixture was extracted with ethyle acetate. The organic phase was dried, concentrated. The residue was purified by preparative TLC (dichloromethane/methanol) to yield the title compound as a white solid (7 mg; 0.02 mmol; 21%).

ESI-MS m/z 407 (M+H)⁺

¹H NMR (MeOD), δ (ppm): 7.89 (s, 1H); 7.71 (d, 1H, J=8.3 Hz); 7.59 (s, 1H); 7.27 (d, 1H, J=8.6 Hz); 6.57 (s, 1H); 4.76 (s, 2H); 3.79 (t, 2H, J=6.7 Hz); 3.73 (t, 2H, J=5.9 Hz); 1.96 (qt, 2H, J=6.2 Hz)

Example 50

5-{4-[(3-hydroxypropyl)amino]-7-(trifluoromethyl)imidazo[1,2-a]quinoxalin-1-yl}-N-methyl-1H-pyrazole-3-carboxamide

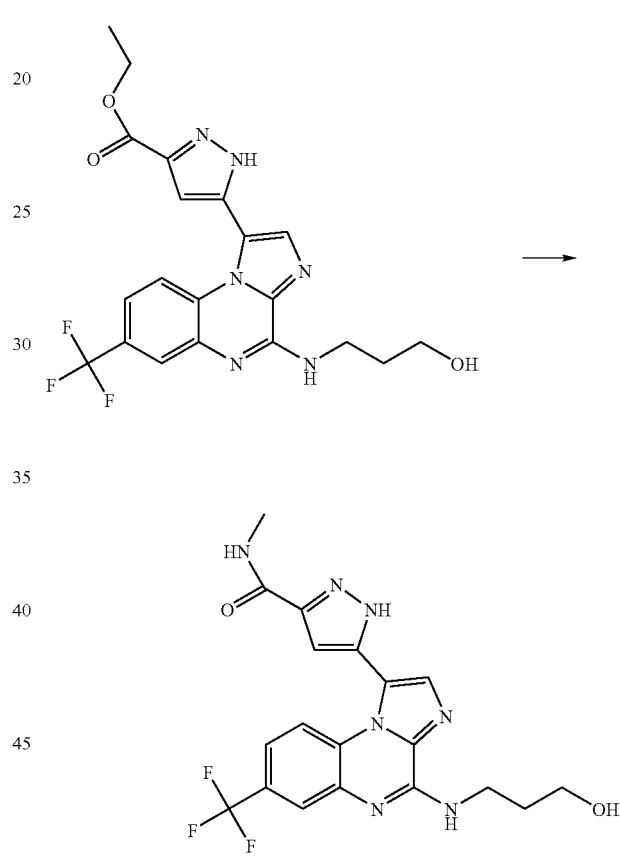

A solution of 5-[4-(3-Hydroxy-propylamino)-7-trifluoromethyl-imidazo[1,2-a]quinoxalin-1-yl]-1H-pyrazole-3-carboxylic acid ethyl ester (0.02 mmol; 7 mg), Methylamine (0.40 mmol; 40% wt in H₂O; 0.1 mL), in THF (0.2 mL), under argon was stirred at 35° C. for 48 hr. Concentration, then purification by preparative TLC (dichloromethane/methanol) afforded the title compound as a white solid (3 mg; 0.007 mmol; 44%).

ESI-MS m/z 434 (M+H)⁺

¹H NMR (MeOD), δ (ppm): 7.91 (s, 1H); 7.67 (s, 1H); 7.31 (d, 1H, J=7.8 Hz); 7.06 (s, 1H); 3.79 (q, 2H, J=6.7 Hz); 3.73 (t, 2H, J=6.2 Hz); 2.95 (s, 3H); 1.98 (qt, 2H, J=6.5 Hz)

Example 51

3-{[1-(1H-pyrazol-5-yl)-7-(trifluoromethoxy)imidazo[1,2-a]quinoxalin-4-yl]amino}propan-1-ol Step 1: Synthesis of 1-Bromo-4-chloro-7-trifluoromethoxy-imidazo[1,2-a]quinoxaline

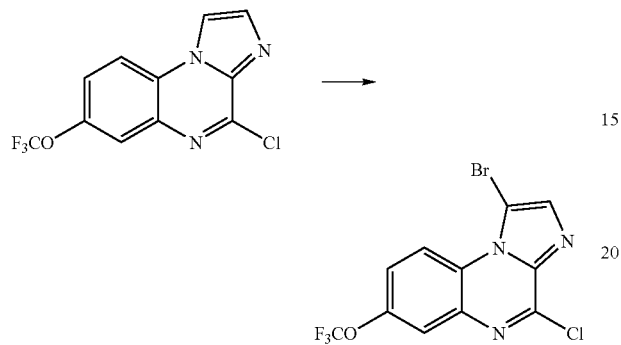

To a stirred solution of 4-chloro-7-(trifluoromethoxy)imidazo[1,2-a]quinoxaline (5.4 g, 18.8 mmol, 1 eq) prepared as described in example 7 step 4 in dichloromethane (94 mL) is added N-bromosuccinimide (5.0 g; 28.2 mmol; 1.5 eq). The solution becomes green during the addition. The solution is allowed to stir for 7 hours at 30° C. until completion of the reaction. Then, the solution is concentrated under vacuum and purified by chromatography on a silica gel column (chloroform/cyclohexane 7:3) to afford the title compound still contaminated by 10% of residual N-bromosuccinimide (7.2 g; 17.7 mmol; 94%). The compound is used as such in the next step without further purification.

$^1$H NMR (DMSO-$d_6$), δ (ppm): 9.26 (d, J=9.2 Hz, 1H), 8.03 (dd, J=2.8 Hz, J=0.8 Hz, 1H), 8.00 (s, 1H), 7.86 (ddd, J=9.2 Hz, J=2.8 Hz, J=0.8 Hz, 1H)

Step 2: Synthesis of 3-(1-Bromo-7-trifluoromethoxy-imidazo[1,2-a]quinoxalin-4-ylamino)-propan-1-ol

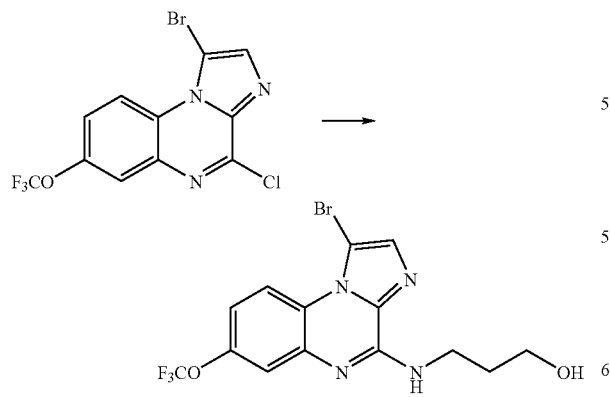

To a stirred solution of 1-bromo-4-chloro-7-trifluoromethoxy-imidazo[1,2-a]quinoxaline (6.5 g, 17.7 mmol, 1 eq) in dioxane (87 mL) is added 3-aminopropan-1-ol (3.4 mL; 44.3 mmol; 2.5 eq). The resulting solution is then heated at reflux for 16 hours until completion of the reaction. The mixture is diluted with ethyl acetate (100 mL) and washed with a 1M aqueous solution of sodium hydroxide (50 mL). The organic layer is separated, dried over sodium sulphate and concentrated in vacuo to afford a beige solid. This powder is washed with diethyl ether to afford after filtration the title compound (6.3 g; 15.5 mmol; 87%) with a 99% HPLC purity.

$^1$H NMR (DMSO-$d_6$), δ (ppm): 9.00 (d, J=9.2 Hz, 1H), 8.00 (t, J=6.0 Hz, 1H), 7.73 (s, 1H), 7.48 (d, J=2.8 Hz, 1H), 731 (dd, J=9.2 Hz, J=2.8 Hz, 1H), 4.59 (t, J=6.8 Hz, 1H), 3.60 (q, J=6.8 Hz, 2H), 3.53 (q, J=6.8 Hz, 2H), 1.82 (qt, J=6.8 Hz, 2H)

ESI-MS m/z 406 (d, (M+H)$^+$)

Step 3: Synthesis of 3-[1-(2H-Pyrazol-3-yl)-7-trifluoromethoxy-imidazo[1,2-a]quinoxalin-4-ylamino]-propan-1-ol

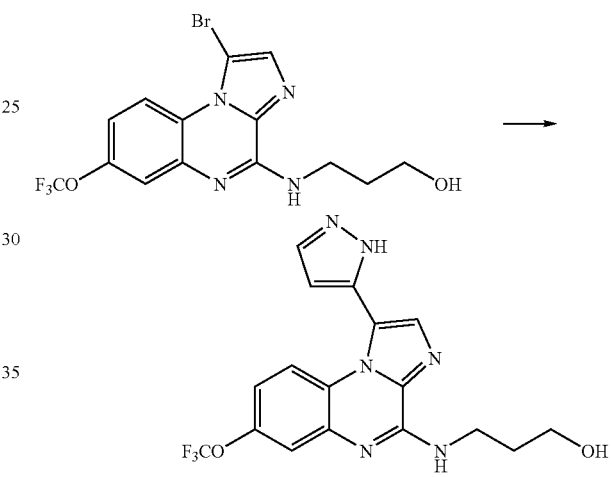

To a solution of 3-(1-bromo-7-trifluoromethoxy-imidazo[1,2-a]quinoxalin-4-ylamino)-propan-1-ol (300 mg; 0.74 mmol; 1 eq) in N,N-dimethylformamide (8 mL), pyrazoleboronic acid (166 mg, 1.48 mmol; 2 eq) is added under argon followed by sodium carbonate (314 mg; 2.96 mmol; 4 eq) and tetrakis(triphenylphosphine)palladium (257 mg; 0.22 mmol; 0.3 eq). The solution is allowed to stir for 17 hours at 130° C. until the reaction is complete on TLC. The crude mixture is cooled to room temperature, diluted with ethyl acetate (50 mL), washed once with a saturated solution of sodium hydrogenocarbonate (90 mL) and three times with brine (3×25 mL). The resulting organic phase is dried over sodium sulfate, filtered and concentrated under vacuum to afford a crude brown powder. This solid is purified by chromatography on silica gel (gradient dichloromethane/methanol 98:2→95:5) to afford the title compound as an orange powder. Recristallization of this solid from ethyl acetate at 0-5° C. afforded the pure title compound (88 mg; 0.22 mmol; 30%) after filtration, washing with diethyl ether and drying of the resulting beige powder.

$^1$H NMR (DMSO-$d_6$), δ (ppm): 13.43 (s, 1H), 8.05-7.95 (m, 2H), 7.77 (broad s, 1H), 7.65 (s, 1H), 7.45 (s, 1H), 7.06 (d, J=8.4 Hz, 1H), 6.66 (s, 1H), 4.62 (t, J=6.8 Hz, 1H), 3.65 (q, J=6.8 Hz, 2H), 3.55 (q, J=6.8 Hz, 2H), 1.84 (qt, J=6.8 Hz, 2H)

ESI-MS m/z 393 (M+H)$^+$

Example 52

3-(8-bromo-7-trifluoromethyl-imidazo[1,2-a]qui-
noxalin-4-ylamino)-propan-1-ol

Step 1: Synthesis of 1-bromo-5-fluoro-4-nitro-2-(trifluoromethyl)benzene

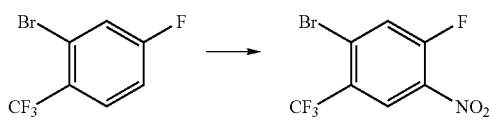

To a stirred mixture of 2-bromo-4-fluorotrifluoromethyl-benzene (33.7 g, 0.1387 mol) in sulfuric acid (98%, 34 mL) at 5° C. under nitrogen is added dropwise a mixture of sulfuric acid (98%, 10.1 mL) with fuming nitric acid (6.7 mL). The mixture is warmed up to room temperature for 2 hours and cooled down to 5° C. before adding water (60 mL). The resulting mixture is extracted twice with ethyl acetate (10 mL). The combined organic phases are washed with a saturated solution of sodium hydrogencarbonate (60 mL), water (60 mL) and dried over sodium sulfate. Concentration affords the title compound as a yellow solid (37.1 g, 92.9%)

$^1$H NMR (DMSO-d$_6$), δ (ppm): 8.50 (d, J=7.4 Hz, 1H), 8.42 (d, J=8.4 Hz, 1H)

Step 2: Synthesis of 1-[5-bromo-2-nitro-4-(trifluoromethyl)phenyl]-1H-imidazole

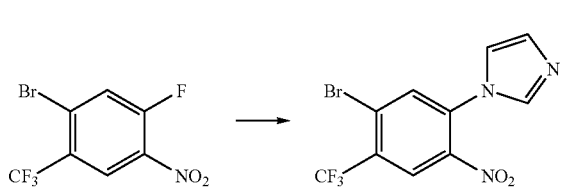 [SMILES: O=[N+]([O-])c1cc(C(F)(F)F)c(Br)cc1F ; O=[N+]([O-])c1cc(C(F)(F)F)c(Br)cc1-n1ccnc1]

A mixture of 1-bromo-5-fluoro-4-nitro-2-(trifluoromethyl)benzene (16.0 g, 0.0556 mol), imidazole (4.0 g, 0.0588 mol) and N,N-diisopropylethylamine (10.1 mL, 0.0582 mol) in acetonitrile (160 mL) is stirred under nitrogen for 1.5 hour at 80° C. After concentration of the reaction mixture, the residue is partitioned between water and ethyl acetate. The aqueous phase is extracted with ethyl acetate, the combined organic phases are washed in turn with a saturated solution of ammonium chloride, brine and dried over sodium sulfate. Concentration and purification by cake filtration over silica gel, eluting with a mixture of ethyl acetate and cyclohexane from 2/8 to 1/1 affords the title compound as a yellow solid (16.1 g, 86.2%)

Melting point: 149.4-157.0° C.

$^1$H NMR (DMSO-d$_6$), δ (ppm): 8.58 (s, 1H), 8.43 (s, 1H), 8.07 (s, 1H), 7.53 (s, 1H), 7.16 (s, 1H)

Step 3: Synthesis of 4-bromo-2-(1H-imidazol-1-yl)-5-(trifluoromethyl)aniline

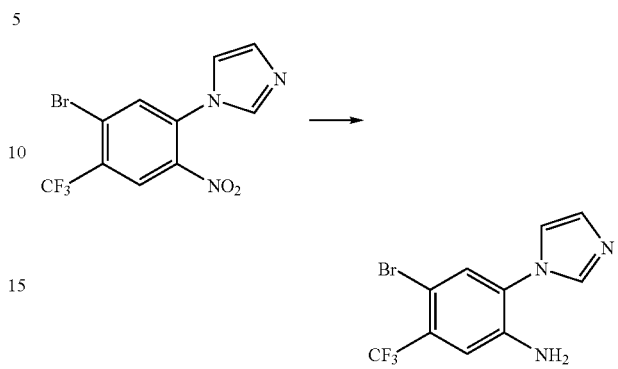

1-[5-bromo-2-nitro-4-(trifluoromethyl)phenyl]-1H-imidazole (15.50 g, 0.0461 mol) is stirred with SnCl$_2$.2H$_2$O (51.77 g, 0.2274 mol) in ethanol (78 mL) at 80° C. for 2 hours. After cooling down to room temperature, the mixture is concentrated and partitioned between water (200 mL) and ethyl acetate (250 mL). Sodium hydrogencarbonate powder is added to adjust the pH to 8. The milky suspension is filtrated, the cake is washed with ethyl acetate and the combined organic phases are washed with water and dried over sodium sulfate. Concentration affords the title compound as a pale yellow solid (12.70 g, 90.0%)

$^1$H NMR (DMSO-d$_6$), δ (ppm): 7.88 (s, 1H), 7.55 (s, 1H), 7.41 (s, 1H), 7.35 (s, 1H), 7.14 (s, 1H), 5.72 (s, 2H)

Step 4: Synthesis of 8-bromo-7-(trifluoromethyl)imidazo[1,2-a]quinoxalin-4(5H)-one

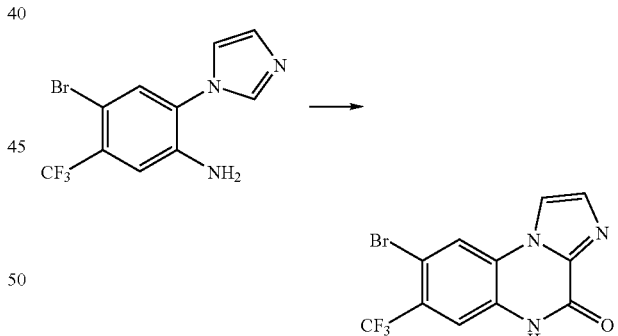

4-Bromo-2-(1H-imidazol-1-yl)-5-(trifluoromethyl) aniline (12.65 g, 0.0413 mol) is stirred under nitrogen with N,N-carbonyldiimidazole (13.8 g, 0.0825 mol) at 135° C. for 7 hours. After being cooled down to room temperature, the mixture is filtered to yield a grey solid, which is suspended in ethyl acetate (500 mL) and stirred at reflux for 10 minutes. After filtration at room temperature, the solid is washed with ethyl acetated (200 mL) and dried under vacuum to afford the title compound as a grey powder (9.5 g, 69.2%)

$^1$H NMR (DMSO-d$_6$), δ (ppm): 12.11 (s, 1H), 8.75 (s, 1H), 8.69 (d, J=1.1 Hz, 1H), 7.77 (s, 1H), 7.66 (d, J=1.3 Hz, 1H)

Step 5: Synthesis of 8-bromo-4-chloro-7-(trifluoromethyl)imidazo[1,2-a]quinoxaline

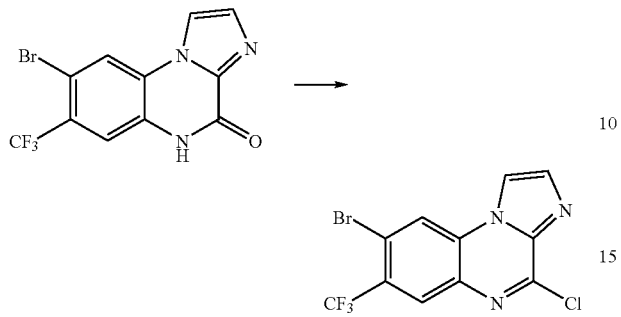

8-Bromo-7-(trifluoromethyl)imidazo[1,2-a]quinoxalin-4 (5H)-one (9.4 g, 0.0283 mol) is stirred under nitrogen with N,N-dimethylaniline (14.5 mL, 0.1123 mol) and phosphoryl chloride (190 mL, 2.0119 mol) at reflux (120° C.) for 1.5 hour. After cooling down to room temperature, the mixture is slowly poured in a mixture of water (2 L) and sodium hydroxide 5N (1 L) below 10° C. The mixture is extracted four times with ethyl acetate (200 mL) and the combined organic phases are washed with water (200 mL), dried over sodium sulfate and concentrated to about 100 mL. Cyclohexane (500 mL) is added at room temperature. The mixture is cooled to 0-5° C. and filtered. The cake is washed with cyclohexane and dried under vacuum to afford the title compound as a yellow solid (7.98 g, 80.4%)

$^1$H NMR (DMSO-d$_6$), δ (ppm): 9.1 (s, 1H), 8.44 (s, 1H), 7.98 (d, J=1.1 Hz, 1H)

Step 6: Synthesis of 3-(8-bromo-7-trifluoromethyl-imidazo[1,2-a]quinoxalin-4-ylamino)-propan-1-ol

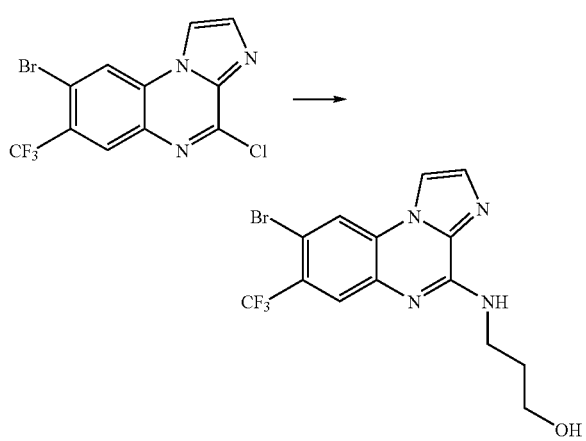

8-Bromo-4-chloro-7-(trifluoromethyl)imidazo[1,2-a]quinoxaline (7.8 g, 0.0222 mol) is stirred under nitrogen with 3-propanolamine (4.2 mL, 0.0540 mol) in 1,4-dioxane (156 mL) at 95° C. for 2 hours. The reaction mixture is then cooled down to room temperature and concentrated. The residue is partitioned between a saturated ammonium chloride aqueous solution (150 mL) and ethyl acetate (150 mL). The aqueous phase is extracted twice with ethyl acetate (50 mL) and the combined organic phases are dried over sodium sulfate. The organic solution is concentrated to about 100 mL and cyclohexane (300 mL) is added at room temperature. The mixture is filtered at 0-5° C. and the cake is washed three times with cyclohexane (50 mL) and dried under vacuum to afford the title compound as a yellow solid (7.7 g, 88.9%)

Melting point: 148.2-160.8° C.

$^1$H NMR (DMSO-d$_6$), δ (ppm): 8.75 (d, J=1.3, 1H), 8.70 (s, 1H), 8.19 (t, J=5.5, 1H), 7.87 (s, 1H), 7.68 (d, J=1.13, 1H), 4.63 (t, J=5.0, 1H), 3.61 (m, 2H), 3.52 (m, 2H), 1.82 (q, J=6.4 Hz, 2H)

Example 53

3-({8-[(pyridin-2-ylamino)methyl]-7-(trifluoromethyl)imidazo[1,2-a]quinoxalin-4-yl}amino)propan-1-ol

Step 1: Synthesis of 3-{[7-(trifluoromethyl)-8-vinylimidazo[1,2-a]quinoxalin-4-yl]amino}propan-1-ol

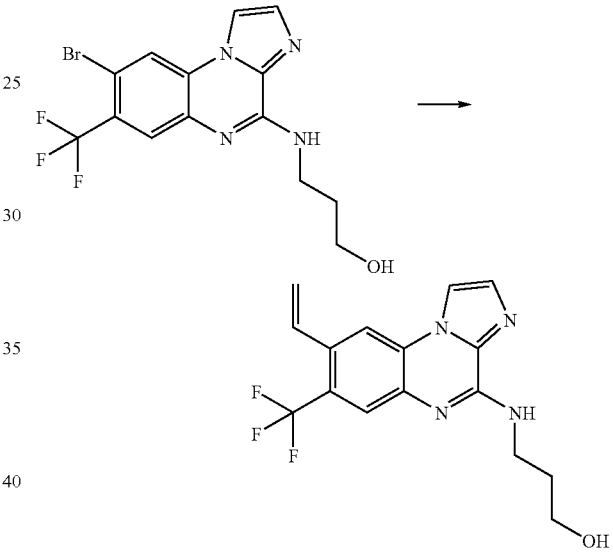

A solution of 3-(8-bromo-7-trifluoromethyl-imidazo[1,2-a]quinoxalin-4-ylamino)-propan-1-ol prepared as in example 52 (1 g; 2.57 mmol; 1 eq), 1,1'bis(diphenylphosphino) ferrocene)palladium dichloride. Dichloromethane complex (210 mg; 0.257 mmol; 0.1 eq), vinylboronic acid pinacol ester 4,4,5,5-tetramethyl-2-vinyl-1,3,2-dioxaborolane (700 µl; 4.1 mmol; 1.6 eq), potassium carbonate (1.42 g; 10.28 mmol; 4 eq) in acetonitrile (12 ml) and water (4 ml) is stirred 24 h at 65° C. under argon. The conversion being slow the reaction mixture is stirred for 3 additional days at 65° C. under argon with daily addition of 1,1'bis(diphenylphosphino) ferrocene) palladium dichloride. dichloromethane complex (105 mg; 0.129 mmol; 0.05 additional eq) and vinylboronic acid pinacol ester 4,4,5,5-tetramethyl-2-vinyl-1,3,2-dioxaborolane (500 µl; 2.9 mmol; 1.1 additional eq). Concentration, partition (ethyl acetate/water), extraction of the aqueous phase (ethyl acetate), reunion of the organic phases, drying (magnesium sulphate) and purification by flash chromatography on silica gel (gradient of methanol 0 to 20% in dichloromethane) followed by trituration in methanol afforded the title compound (118 mg; 0.351 mmol; 14%) as a pale yellow powder.

ESI-MS m/z 337 (M+H)+

Step 2: Synthesis of 4-[(3-hydroxypropyl)amino]-7-(trifluoromethyl)imidazo[1,2-a]quinoxaline-8-carbaldehyde

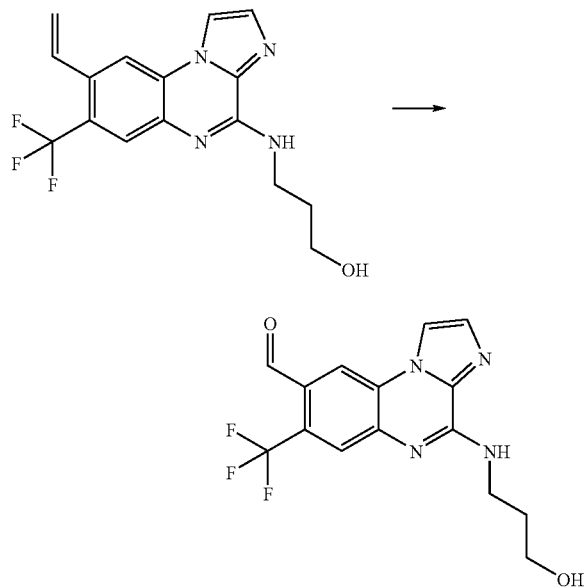

A solution of 3-{[7-(trifluoromethyl)-8-vinylimidazo[1,2-a]quinoxalin-4-yl]amino}propan-1-ol (110 mg; 0.32 mmol; 1 eq), osmium tetroxide (2.5% in tert-butanol, 166 mg; 0.016 mmol; 0.05 eq), N-methylmorpholine oxide (76 mg; 0.654 mmol; 2 eq) in acetone (3 ml) and water (0.33 ml) is stirred at 30° C. during 3 days. A suspension of sodium periodate (280 mg; 1.31 mmol; 4 eq) in water (1.6 ml) is then added and the resulting reaction mixture is stirred at 30° C. during 16 h. Partition (aqueous sodium sulfite/ethyl acetate), extraction of the aqueous phase (ethyl acetate), reunion of the organic phases, drying (magnesium sulphate) and purification by prep CCM on silicagel (dichloromethane/methanol 95:5) affords the title product as an off-white powder (64 mg; 0.19 mmol; 59%).

ESI-MS m/z 339 (M+H)+

Step 3: Synthesis of 3-({8-[(pyridin-2-ylamino)methyl]-7-(trifluoromethyl)imidazo[1,2-a]quinoxalin-4-yl}amino)propan-1-ol

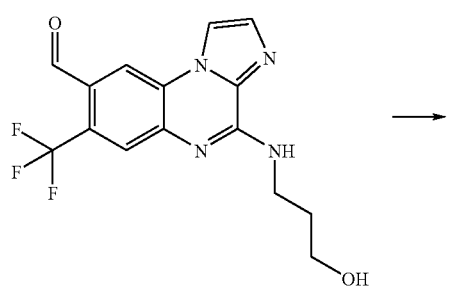

-continued

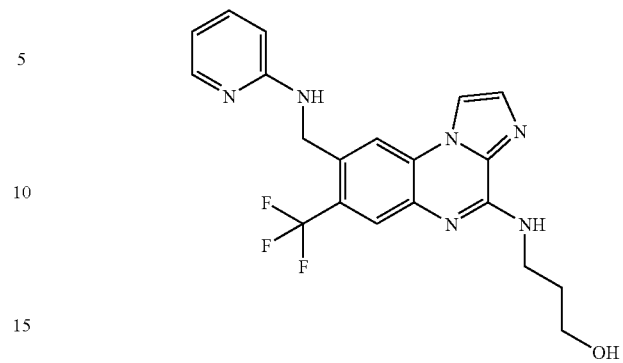

To a solution of 4-[(3-hydroxypropyl)amino]-7-(trifluoromethyl)imidazo[1,2-a]quinoxaline-8-carbaldehyde (25 mg; 0.07 mmol; 1 eq), 2-aminopyridine (20 mg; 0.21 mmol; 3 eq) and titanium tetraisopropoxide (60 mg; 0.21 mg; 3 eq) in anhydrous tetrahydrofuran (0.2 ml) with a few 4A molecular sieves stirred under Ar at rt for 5 h is added sodium borohydride (3 mg; 0.07 mmol; 1 eq). The resulting reaction mixture is then stirred under Ar at rt for 16 h. Partition (aqueous ammonium chloride/ethyl acetate), filtration over Celite, extraction of the aqueous phase (ethyl acetate), reunion of the organic phases, drying (magnesium sulphate) and purification by prep CCM on silicagel (dichloromethane/methanol 95:5) affords the title product (7.4 mg; 0.018 mmol; 25%).

$^1$H NMR (DMSO-$d_6$), δ (ppm): 8.48 (s, 1H), 8.26 (s, 1H), 8.02-7.97 (m, 2H), 7.84 (s, 1H), 7.65 (s, 1H), 7.42 (t, J=7.5 Hz, 1H), 7.04-6.96 (m, 1H), 6.62 (d, J=8.3 Hz, 1H), 6.53 (t, J=7.0 Hz, 1H), 4.72 (d, J=5.1 Hz, 2H), 4.69-4.58 (m, 1H), 3.63 (t, J=5.9 Hz, 2H), 3.53 (t, J=5.4 Hz, 2H), 1.83 (qt, J=6.45 Hz, 2H)

ESI-MS m/z 417 (M+H)+

Example 54

3-{[1-(1H-pyrazol-5-yl)-7-(2-[trifluoromethyl]phenyl)imidazo[1,2-a]quinoxalin-4-yl]amino}propan-1-ol

Step 1: Synthesis of 3-({1-iodo-7-[2-(trifluoromethyl)phenyl]imidazo[1,2-a]quinoxalin-4-yl}amino)propan-1-ol

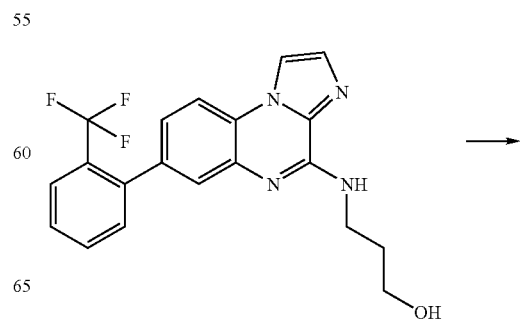

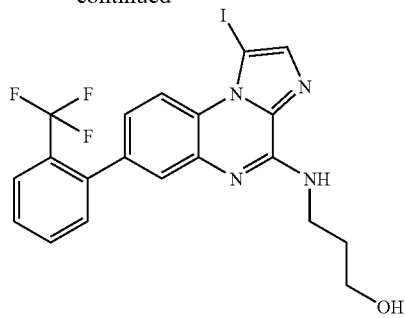

To a mixture protected from light of Selectfluor (103 mg; 0.29 mmol; 1.4 eq) and iodine (63 mg; 0.248 mmol; 1.2 eq) in acetonitrile (1.8 ml) stirred for 10 min under argon is added 3-({7-[2-(trifluoromethyl)phenyl]imidazo[1,2-a]quinoxalin-4-yl}amino) propan-1-ol (80 mg; 0.207 mmol; 1 eq) prepared as in example 5. The reaction mixture is stirred at rt overnight. Filtration of solid side-products, concentration, dissolution in ethyl acetate, washing with brine, aqueous sodium carbonate and water, drying (magnesium sulphate) and purification by prep CCM on silicagel (dichloromethane/methanol 95:5) affords the title product as an orange oil (88 mg; 0.17 mmol; 82%).

ESI-MS m/z 513 (M+H)+

Step 2: Synthesis of 3-{[1-(1H-pyrazol-5-yl)-7-(2-[trifluoromethyl]phenyl)imidazo[1,2-a]quinoxalin-4-yl]amino}propan-1-ol

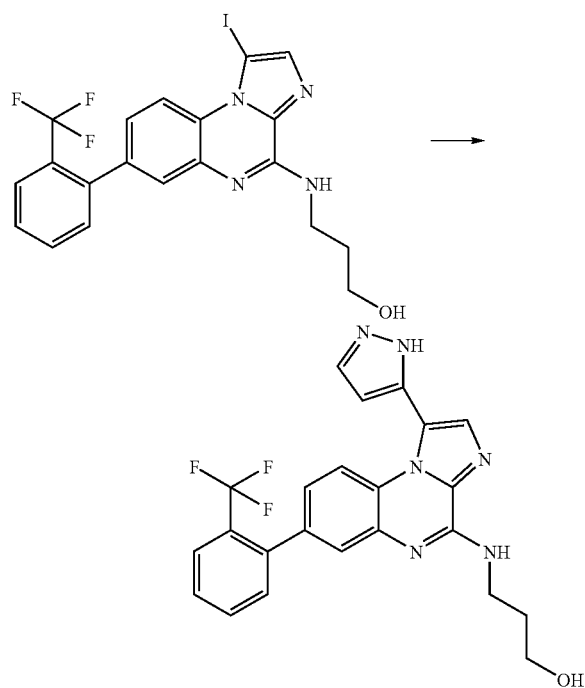

A solution of 3-({1-iodo-7-[2-(trifluoromethyl)phenyl] imidazo[1,2-a]quinoxalin-4-yl}amino)propan-1-ol (42 mg; 0.082 mmol; 1 eq), 1,1'bis(diphenylphosphino) ferrocene) palladium dichloride. dichloromethane complex (20.1 mg; 0.025 mmol; 0.3 eq), 1H-pyrazole-5-boronic acid (18.3 mg; 0.164 mmol; 2 eq) and sodium carbonate (26 mg; 0.246 mmol; 3 eq) in anhydrous dimethylformamide (0.37 ml) is stirred under argon at 100° C. for 4 h. Partition (aqueous sodium hydrogenocarbonate/ethyl acetate), filtration over Celite, extraction of the aqueous phase (ethyl acetate), reunion of the organic phases, drying (magnesium sulphate) and purification by prep CCM on silicagel (dichloromethane/methanol 95:5) affords the title product (15 mg; 0.033 mmol; 39%) as an off-white solid.

$^1$H NMR (DMSO-$d_6$), δ (ppm): 13.44 (s, 1H), 8.05 (s, 1H), 7.84 (d, J=7.8 Hz, 2H), 7.74-7.61 (m, 4H), 7.46 (d, J=11.7 Hz, 2H), 6.97 (d, J=9.3 Hz, 1H), 6.68 (s, 1H), 4.67 (t, J=5.4 Hz, 1H), 3.64 (q, J=6.5 Hz, 2H), 3.54 (q, J=5.9 Hz, 2H), 1.87-1.81 (m, 2H)

ESI-MS m/z 453 (M+H)+

Example 55

3-[1-(5-Methyl-2H-1,2,4]triazol-3-yl)-7-trifluoromethoxy-imidazo[1,2-a]quinoxalin-4-ylamino]-propan-1-ol Step 1: Synthesis of 4-(3-Hydroxy-propylamino)-7-trifluoromethoxy-imidazo[1,2-a]quinoxaline-1-carbonitrile

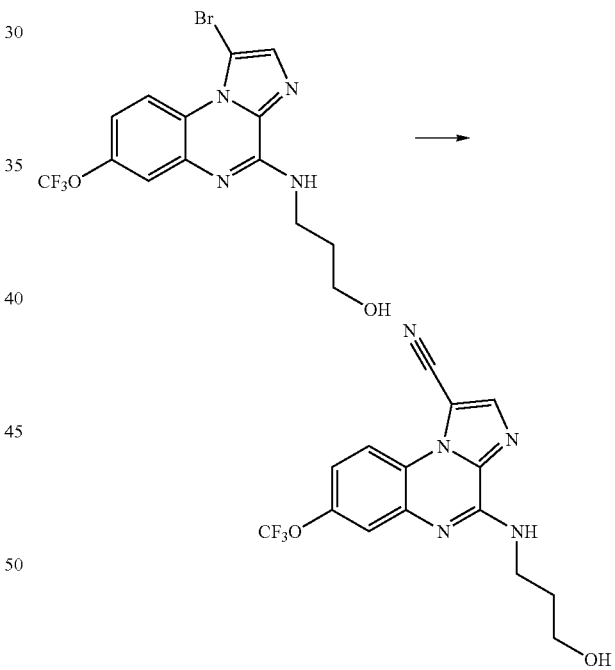

To a stirred solution of 3-(1-Bromo-7-trifluoromethoxy-imidazo[1,2-a]quinoxalin-4-ylamino)-propan-1-ol (1.00 g; 2.47 mmol; 1 eq) prepared as in example 51 step 2 in degassed N-methylpyrrolidone (10 mL) are successively added under argon tetrakis-triphenylphosphine palladium (570 mg; 0.49 mmol; 0.2 eq) and copper cyanide (885 mg; 9.90 mmol; 4 eq). The resulting solution is then heated at 160° C. for 3 hours until reaction is complete on TLC. The mixture is then quenched with an aqueous solution saturated with sodium hydrogenocarbonate (50 mL) and the resulting basic solution (pH>8) is extracted with ethyl acetate (100 mL). The organic layer is separated, washed with an aqueous solution saturated with sodium hydrogenocarbonate (50 mL), dried over sodium sulfate, filtered and concentrated under vacuum to afford a brown oil. Chromatography of this crude oil on silica gel (gradient of ethyl acetate/cyclohexane from 1:9 to 5:5) afforded the title compound contaminated by 21% of residual triphenylphosphine oxide. Therefore, the mixture was further purified by a second column chromatography (chloroform/ethyl acetate 7:3) yielding the pure title compound (424 mg; 1.21 mmol; 49%).

$^1$H NMR (CD$_3$OD), δ (ppm): 8.55 (d, J=9.2 Hz, 1H), 8.24 (s, 1H), 7.54 (d, J=2.2 Hz, 1H), 7.25 (dd, J=9.2 Hz, J=2.2 Hz, 1H), 3.75 (t, J=6.4 Hz, 2H), 3.72 (t, J=6.4 Hz, 2H), 1.96 (qt, J=6.6 Hz, 2H)

Step 2: Synthesis of 3-[1-(5-Methyl-2H-[1,2,4]triazol-3-yl)-7-trifluoromethoxy-imidazo[1,2-a]quinoxalin-4-ylamino]-propan-1-ol

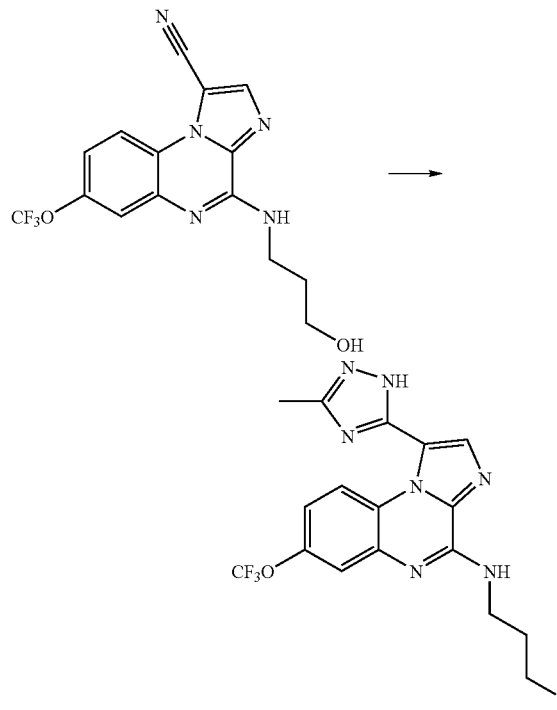

To a stirred solution of compound 4-(3-Hydroxy-propylamino)-7-trifluoromethoxy-imidazo[1,2-a]quinoxaline-1-carbonitrile (50 mg; 0.142 mmol; 1 eq) in n-butanol (570 μL) are successively added under argon acetic hydrazide (90% grade; 14 mg; 0.171 mmol; 1.2 eq) and potassium carbonate (30 mg; 0.214 mmol; 1.5 eq). The resulting solution is then heated at 180° C. for 2 hours until the starting material has been completely consumed on TLC. The reaction is evaporated under vacuum and the resulting crude residue is purified on silica gel (dichloromethane/methanol 95:5) yielding the pure title compound (5 mg; 0.012 mmol; 8%) as a white powder.

$^1$H NMR (CD$_3$OD), δ (ppm): 7.92 (d, J=9.2 Hz, 1H), 7.78 (s, 1H), 7.53 (d, J=2.0 Hz, 1H), 7.03 (dd, J=9.2 Hz, J=2.0 Hz, 1H), 3.79 (t, J=6.2 Hz, 2H), 3.74 (t, J=6.2 Hz, 2H), 2.59 (s, 3H), 1.98 (qt, J=6.2 Hz, 2H)

APPI-MS m/z 408 (M+H)$^+$

Example 56

3-{[8-(benzylamino)-7-(trifluoromethyl)imidazo[1,2-a]quinoxalin-4-yl]amino}propan-1-ol Step 1: Synthesis of N-benzyl-5-(1H-imidazol-1-yl)-4-nitro-2-(trifluoromethyl)aniline

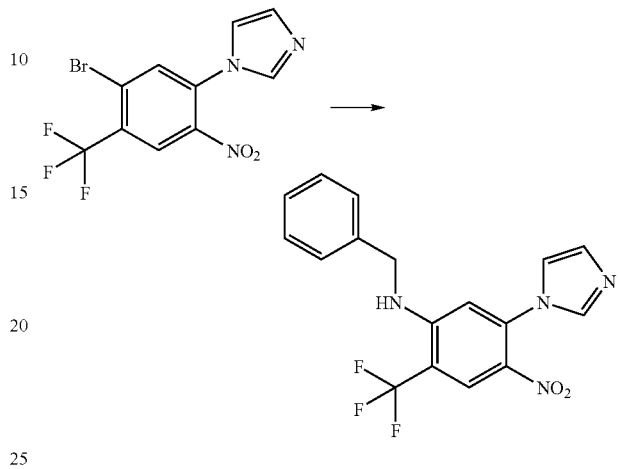

A solution of 1-[5-bromo-2-nitro-4-(trifluoromethyl)phenyl]-1H-imidazole (580 mg; 1.73 mmol; 1 eq) prepared as in example 52 step 2, benzylamine (210 μl; 1.9 mmol; 1.1 eq) and diisopropylethylamine (331 μl; 1.9 mmol; 1.1 eq) in anhydrous acetonitrile is stirred at 60° C. for 16 h. Concentration, partition (ethyl acetate/aqueous ammonium chloride), extraction of the aqueous phase (ethyl acetate), reunion of the organic phases, drying (magnesium sulfate), concentration and purification by prep CCM on silicagel (dichloromethane/ethyl acetate 50:50) affords the title product (200 mg; 0.552 mmol; 32%) as a yellow solid.

ESI-MS m/z 363 (M+H)+

Step 2: Synthesis of N-benzyl-5-(1H-imidazol-1-yl)-2-(trifluoromethyl)benzene-1,4-diamine

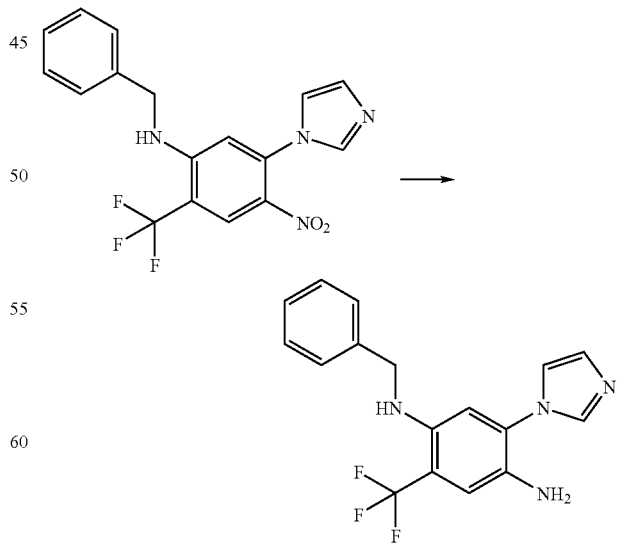

A solution of N-benzyl-5-(1H-imidazol-1-yl)-4-nitro-2-(trifluoromethyl)aniline (190 mg; 0.52 mmol; 1 eq) and tin chloride dihydrate (591 mg; 2.62 mmol; 5 eq) in ethanol (2 ml) is stirred under argon at 80° C. for 4 h. Concentration, partition (ethyl acetate/aqueous sodium hydrogenocarbonate), addition of solid sodium hydrogenocarbonate to adjust the pH around 8, filtration over Celite, extraction of the cake solid with ethyl acetate, reunion of the organic phases, additional washings (aqueous ammonium chloride, brine), drying (magnesium sulfate) and concentration affords the title product (165 mg; 0.50 mmol; 96%) as a yellow solid.

ESI-MS m/z 333 (M+H)+

Step 3: Synthesis of 8-(benzylamino)-7-(trifluoromethyl)imidazo[1,2-a]quinoxalin-4(5H)-one

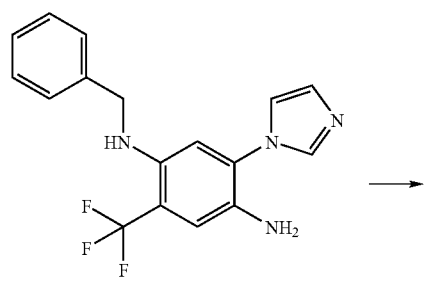

A solution of N-benzyl-5-(1H-imidazol-1-yl)-2-(trifluoromethyl)benzene-1,4-diamine (160 mg; 0.48 mmol; 1 eq) and carbonyl diimidazole (156 mg; 0.96 mmol; 2 eq) in 1,2-dichlorobenzene (20 ml) is stirred under argon at reflux for 3 h. Concentration, filtration over a small silicagel pad with ethyl acetate as eluent and purification by prep CCM on silicagel (ethyl acetate) affords the title product (72 mg; 0.2 mmol; 42%) as a pale yellow solid.

ESI-MS m/z 359 (M+H)+

Step 4: Synthesis of N-benzyl-4-chloro-7-(trifluoromethyl)imidazo[1,2-a]quinoxalin-8-amine

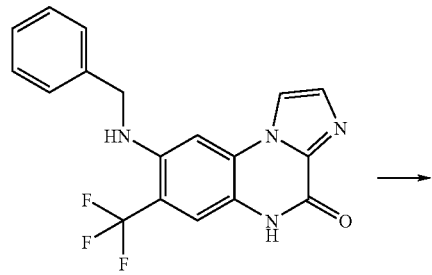

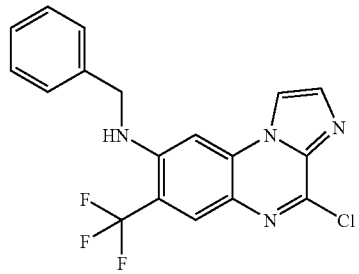

A solution of 8-(benzylamino)-7-(trifluoromethyl)imidazo[1,2-a]quinoxalin-4(5H)-one (72 mg; 0.2 mmol; 1 eq) and N,N'-dimethylaniline (0.2 ml) in phosphoryl chloride (2 ml) is stirred at 135° C. under argon for 2 h. Concentration, partition (ice water/ethyl acetate), extraction of the aqueous phase (ethyl acetate), reunion of the organic phases, drying (magnesium sulfate), concentration and purification by prep CCM on silicagel (dichloromethane/methanol 90:10) affords the title product (35 mg; 0.093 mmol; 47%) as a yellow solid.

ESI-MS m/z 377 and 379 (M+H)+

Step 5: Synthesis of 3-{[8-(benzylamino)-7-(trifluoromethyl)imidazo[1,2-a]quinoxalin-4-yl]amino}propan-1-ol

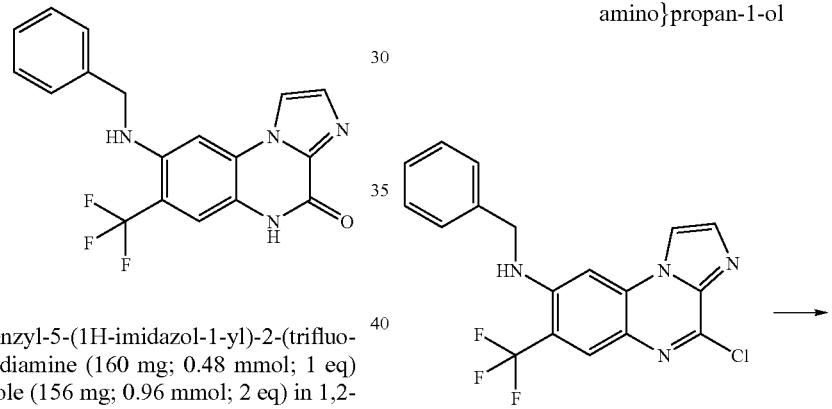

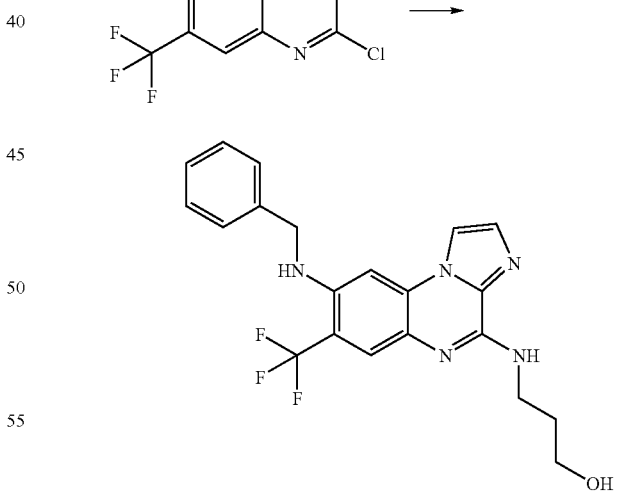

A solution of N-benzyl-4-chloro-7-(trifluoromethyl)imidazo[1,2-a]quinoxalin-8-amine (30 mg; 0.079 mmol; 1 eq), 3-propanolamine (20 μl; 0.264 mmol; 3.3 eq) and diisopropylethylamine (15 μl; 0.088 mmol; 1.1 eq) in anhydrous 1,4-dioxane (0.5 ml) is stirred under argon at 100° C. for 16 h. Partition (ethyl acetate/aqueous ammonium chloride), washings of the organic phase (twice with aqueous ammonium chloride, once with brine), drying (magnesium sulfate) and concentration affords the title product (28 mg; 0.067 mmol; 86%) as a white solid.

$^1$H NMR (DMSO-$d_6$), δ (ppm): 8.42 (s, 1H), 7.62 (s, 1H), 7.58 (s, 1H), 7.48 (d, J=6.9 Hz, 2H), 7.41 (t, J=5.6 Hz, 1H), 7.32 (t, J=7.3 Hz, 2H), 7.24 (s, 1H), 7.20 (t, J=7.3 Hz, 1H), 6.23 (t, J=6.7 Hz, 1H), 4.63-4.58 (m, 3H), 3.58-3.48 (m, 4H), 1.78 (qt, J=6.4 Hz, 2H)

ESI-MS m/z 416 (M+H)+

Example 57

3-[(7,8-difluoroimidazo[1,2-a]quinoxalin-4-yl)amino]propan-1-ol

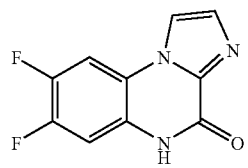 

A mixture of 7,8-difluoroimidazo[1,2-a]quinoxalin-4 (5H)-one (Eur. J. Med. Chem. 1998, 33, 943) (20 mg, 0.090 mmol), hexamethyldisilazane (66 μL, 0.31 mmol), ammonium sulphate (2.4 mg, 0.018 mmol) and 3-aminopropan-1-ol (34 μL, 0.45 mmol) was stirred under argon at 120° C. overnight. The reaction mixture was allowed to cool down to room temperature and the white residue was diluted in ethyl acetate and water. A white precipitate was filtered off and the filtrate was washed with brine. The organic phase was dried over sodium sulfate, filtered and evaporated. The crude product was purified by preparative TLC (silica gel, dichloromethane/methanol 90/10) to afford the title compound as white crystals (4.5 mg, 18%)

$^1$H NMR (CD$_3$OD), δ (ppm): 8.29 (d, J=1.2 Hz, 1H), 7.99 (dd, J=7.7 and 10.9 Hz, 1H), 7.58 (d, J=1.2 Hz, 1H), 7.48 (dd, J=7.9 and 11.9 Hz, 1H), 3.74 (t, J=6.7 Hz, 2H), 3.71 (t, J=6.1 Hz, 2H), 1.95 (qt, J=6.4 Hz, 2H)

ESI-MS m/z 279 (M+H)$^+$.

Example 58

Phosphoric acid mono-{3-[1-(2H-pyrazol-3-yl)-7-trifluoromethyl-imidazo[1,2-a]quinoxalin-4-ylamino]-propyl}ester, disodium salt Step 1: Synthesis of 3-{7-trifluoromethyl-1-[2-(2-trimethylsilanyl-ethoxymethyl)-2H-pyrazol-3-yl]-imidazo[1,2-a]quinoxalin-4-ylamino}propan-1-ol 3-(1-Bromo-7-trifluoromethyl-imidazo[1,2-a]quinoxalin-4-ylamino)-propan-1-ol prepared as in example 2 was converted in 54% yield to the title compound using the general procedure described for Suzuki couplings. The pyrazole boronic acid was prepared according to the procedure described in example 39. Product was purified by silica gel chromatography (ethyl acetate/diethyl ether 2:8).

$^1$H NMR (CD$_3$OD), δ (ppm): 7.93 (broad s, 1H), 7.83 (d, J=1.8 Hz, 1H), 7.71 (s, 1H), 7.26 (d, J=8.8 Hz, 1H), 7.10 (d, J=8.8 Hz, 1H), 6.80 (d, J=1.8 Hz, 1H), 5.29 (s, 2H), 3.84 (t, J=8.6 Hz, 2H), 3.76 (q, J=6.2 Hz, 2H), 3.41 (t, J=6.2 Hz, 2H), 2.00 (qt, J=6.2 Hz, 2H), 0.52 (t, J=8.6 Hz, 2H), −0.17 (s, 9H)

Step 2: Synthesis of phosphoric acid dibenzyl ester 3-{7-trifluoromethyl-1-[2-(2-trimethylsilanyl-ethoxymethyl)-2H-pyrazol-3-yl]imidazo[1,2-a]quinoxalin-4-ylamino}-propyl ester

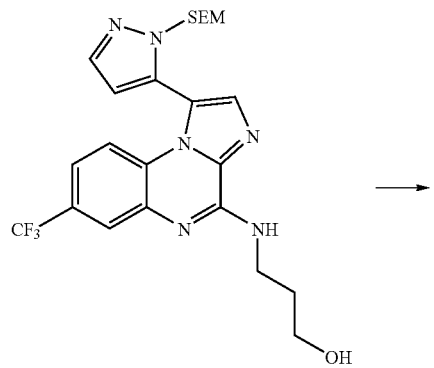

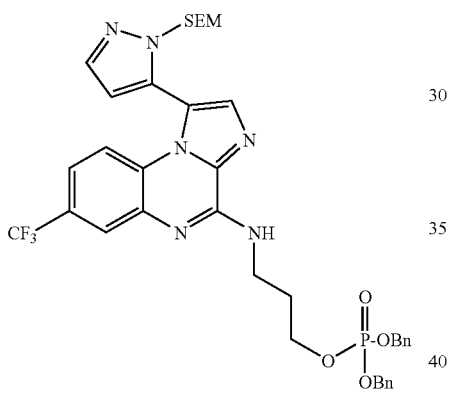

Step 3: Synthesis of phosphoric acid dibenzyl ester 3-[1-(2H-pyrazol-3-yl)-7-trifluoromethyl-imidazo[1,2-a]quinoxalin-4-ylamino]-propyl ester

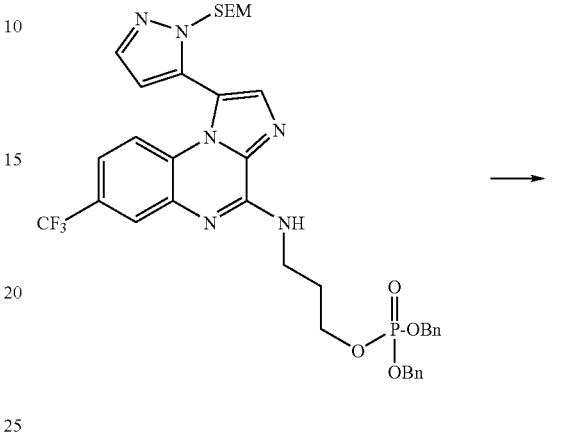

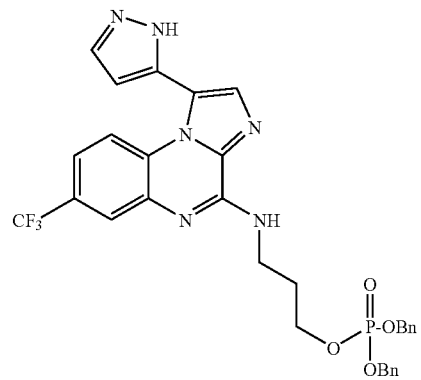

To a stirred solution of 3-{7-trifluoromethyl-1-[2-(2-trimethylsilanyl-ethoxymethyl)-2H-pyrazol-3-yl]imidazo[1,2-a]quinoxalin-4-ylamino}propan-1-ol (771 mg; 1.52 mmol; 1.0 eq) in anhydrous tetrahydrofuran (50 mL) at −40° C. is added potassium tert-butoxide (188 mg; 1.67 mmol; 1.1 eq). The resulting yellow solution is stirred for 10 minutes at −40° C., and tetra benzyl pyrophosphate (899 mg; 1.67 mmol; 1.1 eq) is added. After 90 minutes stirring at −40° C., the reaction mixture is quenched by addition of a saturated solution of ammonium chloride (50 mL) and water (15 mL). The aqueous phase is extracted twice with ethyl acetate (2×60 mL). The combined organic phases are dried over sodium sulphate, filtered and concentrated under vacuum. Purification by silica gel chromatography (elution with a mixture chloroform/ethyl acetate 1/1) afforded the title compound (966 mg; 1.26 mmol; 83%) as a pale yellow oil.

$^1$H NMR (CDCl$_3$), δ (ppm): 7.98 (broad s, 1H), 7.89 (d, J=1.6 Hz, 1H), 7.61 (s, 1H), 7.40-7.30 (m, 10H), 7.21 (dd, J=8.8 Hz, J=1.8 Hz, 1H), 7.02 (d, J=8.8 Hz, 1H), 6.75-6.50 (m, 1H), 6.63 (d, J=1.6 Hz, 1H), 5.27 (s, 2H), 5.10 (d, J=8.2 Hz, 2H), 5.09 (d, J=8.2 Hz, 2H), 4.20 (q, J=6.4 Hz, 2H), 3.79 (q, J=6.4 Hz, 2H), 3.48 (t, J=8.6 Hz, 2H), 2.08 (qt, J=6.4 Hz, 2H), 0.52 (t, J=8.6 Hz, 2H), −0.10 (s, 9H)

To a stirred solution of phosphoric acid dibenzyl ester 3-{7-trifluoromethyl-1-[2-(2-trimethylsilanyl-ethoxymethyl)-2H-pyrazol-3-yl]-imidazo[1,2-a]quinoxalin-4-ylamino}-propyl ester (966 mg; 1.26 mmol; 1.0 eq) in absolute ethanol (7 mL) at 0° C., is added a 4N solution of hydrogen chloride in isopropanol (3.5 mL). The solution is stirred for 5 minutes at 0° C., warmed-up to room temperature and stirred for two additional hours. The reaction mixture is basified with an aqueous solution saturated with sodium hydrogenocarbonate (35 mL). The aqueous layer is extracted three times with ethyl acetate (3×40 mL). The combined organic phases are dried over sodium sulphate, filtered and concentrated under vacuum. Purification by two successive silica gel chromatography (elution with ethyl acetate) afforded the title compound (392 mg; 0.61 mmol; 48%) as a colourless oil.

$^1$H NMR (CD$_3$OD), δ (ppm): 7.96 (m, 1H), 7.89 (m, 1H), 7.61 (m, 2H), 7.35-7.20 (m, 11H), 6.66 (d, J=2.2 Hz, 1H), 5.05 (s, 2H), 5.01 (s, 2H), 4.20 (q, J=6.4 Hz, 2H), 3.78 (t, J=6.4 Hz, 2H), 2.10 (qt, J=6.4 Hz, 2H)

APPI-MS m/z 637 (M+H)$^+$

Step 4: Synthesis of Phosphoric acid mono-{3-[1-(2H-pyrazol-3-yl)-7-trifluoromethyl-imidazo[1,2-a]quinoxalin-4-ylamino]-propyl}ester, disodium salt

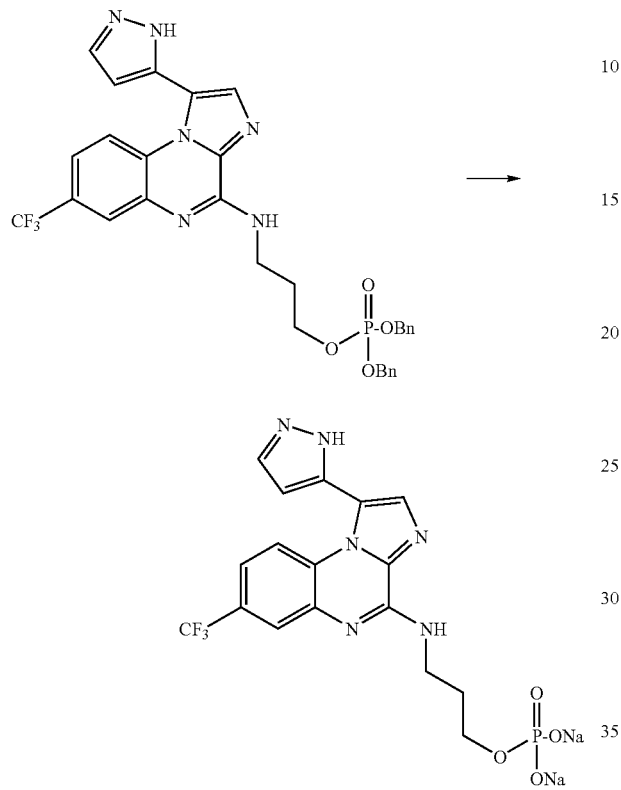

To a stirred solution of phosphoric acid dibenzyl ester 3-[1-(2H-pyrazol-3-yl)-7-trifluoromethyl-imidazo[1,2-a]quinoxalin-4-ylamino]-propyl ester (392 mg; 0.61 mmol; 1.0 eq) in absolute ethanol (61 mL) is added under argon Pd/C 10% (39 mg; 10% w). The reaction mixture is purged with hydrogen and then stirred for two hours under an atmospheric pressure of hydrogen. The catalyst is removed by filtration over Celite and washed with ethanol (3×30 mL). Concentration under vacuum afforded the free phosphoric acid (246 mg; 0.54 mmol; 88%) as a white solid.

To a stirred solution of the previously obtained phosphoric acid (100 mg; 0.22 mmol; 1 eq) in methanol (15 mL) is added, under argon, sodium methoxide (23.7 mg; 0.44 mmol; 2 eq) at room temperature. After 16 hours stirring, methanol is removed under vacuum and the resulting crude residue is re-dissolved in a minimum volume of water. Then acetonitrile is added until precipitation of the title compound. The white precipitate is collected by centrifugation of the resulting heterogeneous solution and then triturated twice in acetonitrile. The resulting white slurry obtained after removal of the solvent is re-dissolved in water and freeze-dried to afford the title compound as a white powder (99 mg; 0.20 mmol; 90%).

$^1$H NMR (D$_2$O), δ (ppm): 8.00 (d, J=1.8 Hz, 1H), 7.65 (s, 1H), 7.50 (s, 1H), 8.00 (d, J=8.6 Hz, 1H), 7.14 (d, J=8.6 Hz, 1H), 6.72 (d, J=1.8 Hz, 1H), 3.91 (q, J=6.8 Hz, 2H), 3.57 (t, J=6.8 Hz, 2H), 1.97 (qt, J=6.8 Hz, 2H)

Not detected in APPI/EI/IC NH$_3$

Example 59

3-[(7-fluoroimidazo[1,2-a]quinoxalin-4-yl)amino] propyl (2R)-2-aminopropanoate bis trifluoracetic acid salt Step 1: Synthesis of 3-[(7-fluoroimidazo[1,2-a]quinoxalin-4-yl)amino]propyl (2R)-2-[(tert-butoxycarbonyl)amino]propanoate

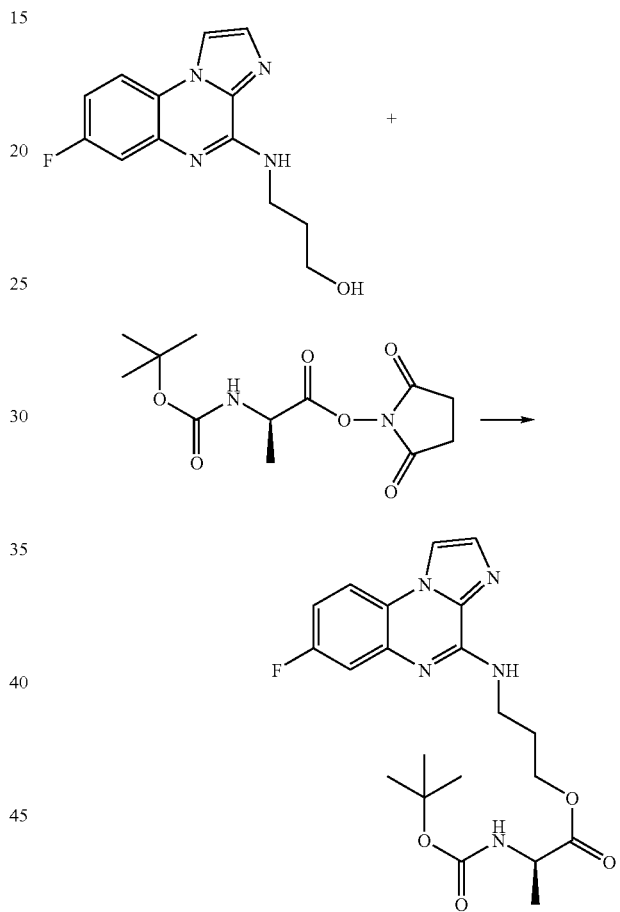

To a solution of commercially available (Peakdale) 3-[(7-fluoroimidazo[1,2-a]quinoxalin-4-yl)amino]propan-1-ol (20 mg, 0.08 mmol) and 1,8-diazabicyclo[5.4.0]undec-7-ene (12 µL, 0.08 mmol) in anhydrous dimethylformamide (600 µL) under argon was added dropwise a solution of tert-butyl {(1R)-2-[(2,5-dioxopyrrolidin-1-yl)oxy]-1-methyl-2-oxoethyl}carbamate (22 mg, 0.08 mmol) in anhydrous dimethylformamide (200 µL). The mixture was stirred at 60° C. for 65 h, then diluted with cold water and extracted four times with chloroform and once with chloroform/isopropanol (5:1). The combined organic layers were washed with brine, dried over sodium sulfate, filtered and evaporated. The crude product was purified by preparative TLC (silica, dichloromethane/methanol 20/1) to afford the title compound as a colorless oil (4 mg, 12%).

ESI-MS m/z 432 (M+H)$^+$.

Step 2: Synthesis of 3-[(7-fluoroimidazo[1,2-a]qui-noxalin-4-yl)amino]propyl (2R)-2-aminopropanoate bis trifluoracetic acid salt

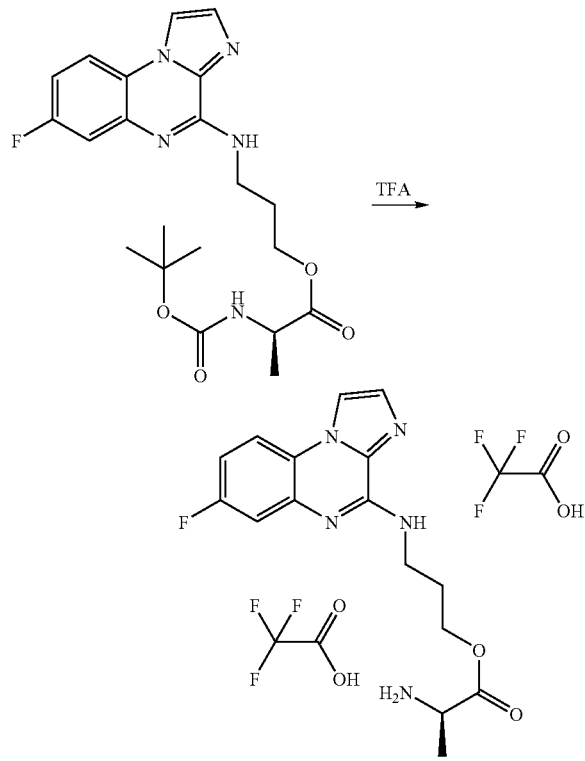

To a solution of 3-[(7-fluoroimidazo[1,2-a]quinoxalin-4-yl)amino]propyl (2R)-2-[(tert-butoxycarbonyl)amino]propanoate (4 mg, 0.0093 mmol) in water (150 μL) cooled at 0° C. was added trifluoroacetic acid (150 μL). The mixture was allowed to warm to room temperature over 3 h under stirring and then concentrated under vacuum to yield a colorless gum. Triturating in chloroform and diethyl ether afforded the title compound as a white solid (3.2 mg, 61%).

$^1$H NMR (D$_2$O), δ (ppm): 8.40 (s, 1H), 8.02 (dd, J=9.1 and 4.9 Hz, 1H), 7.79 (s, 1H), 7.59 (dd, J=9.4 and 2.3 Hz, 1H), 7.35 (dt, J=8.9 and 2.4 Hz, 1H), 4.47 (t, J=6.0 Hz, 2H), 4.23 (q, J=7.3 Hz, 1H), 3.89 (t, J=6.6 Hz, 2H), 2.28 (qt, J=6.2 Hz, 2H), 1.56 (d, J=7.3 Hz, 3H)

PART B

Methods for Assessing Inhibitory Activity of the Compounds

The compounds effect on DltA enzyme has been based on the measure of the inhibition of DltA activity in vitro.

A new method to measure DltA enzymatic activity in vitro was established and optimized in order to perform a reliable and easy assessment of the compounds effect, and in an HTS format.

To this end, a recombinant protein Dlta was expressed and purified after cloning of the gene of *S. agalatiae* as described below:

Cloning of dltA Gene from *S. agalatiae* and Expression of Protein DltA

The dltA gene was PCR amplified from chromosomal DNA of *S. agalactiae* NEM316 using Pfu polymerase (Promega®) and primers F-dltA having sequence SEQ ID N°1 CACCATGATACATGATATGATTAAAA-CAATTGAGCATTTTGC and R-dltA having sequence SEQ ID N°2 TCACTTGTTTACCTCGCTCATAAGACC. Purified PCR product was cloned into prokaryotic expression vector plasmid pET100 (Invitrogen®) so as to generate a recombinant so as to generate a recombinant N-terminal His-tag fusion DltA protein. The resulting plasmid was introduced into *E. coli* BL21 (DE3) Star (Invitrogen, Carlsbad, Calif.) as a recipient, following manufacturer's instruction. For protein expression, overnight culture was used to inoculate fresh Luria broth (LB) medium supplemented with ampicillin (100 μg/ml. Bacteria were grown at 37° C. under aerobic conditions and isopropyl-beta-D-thiogalactopyranoside (IPTG) (Qbiogene, Vista, Calif.) was added to 1 mM when DO$_{600}$ of the bacterial culture had reached 0.5. After a further incubation for 3 hours, cells were harvested by centrifugation.

Purification of the recombinant DltA protein was performed by affinity chromatography on nickel-nitrilotriacetic acid (Ni-NTA) column following manufacturer's instructions (Qiagen). Pellet was resuspended in buffer L (50 mM NaH$_2$PO$_4$, 300 mM NaCl) containing lyzozyme (1 mg/ml final) and incubated for one hour in ice. The bacterial suspension was sonicated (6 cycles of 30 sec separated by one minute of cooling on ice) (Branson Sonifier). The supernatant was collected by centrifugation and added to Ni-NTA agarose beads. The washing and elution steps were performed using buffer L containing increase concentration of imidazole, as a competitor of polyhistidine Tag. Elution was checked by a 12% SDS-PAGE.

Fractions containing recombinant DltA protein were adjusted to 50% glycerol and stored at −20° C. until use. The protein concentrations were determined using the Bradford protein assay (Pierce, Rockford, Ill.).

Methods 1: DltA HTS Assays

DltA is a D-Alanine:D-Alanyl carrier protein ligase presenting close similarities with the adenylation domains of the non ribosomal peptide synthetases. It catalyses the ATP activated coupling of D-Alanine to DltC, a small phosphopantetheinyl protein (acyl carrier protein like). The product, the thioester D-Ala-DltC is thought to be the ultimate donor of D-Ala in the D-Alanisation of the lipoteichoic acid. Measure of DltA activity has been described in the literature, but these experiments were essentially radioactivity-based and required the protein DltC as natural substrate of the enzyme ((1)—*Journal of Biological Chemistry*. 1971, Vol. 246, 24, p. 6136-6143; (2)—*Journal of Bacteriology*, 1994, p. 681-690; (3)—*Journal of Bacteriology*, 1996, p. 3869-3876; (4)—*Journal of Bacteriology*, 2001, p. 2051-2058; (5)—*FEBS Journal*, 2005, 272, p. 2993-3003)

The assay described below makes use of dithiothreitol (DTT) instead of DltC as reactive thiol in the catalyzed reaction. In fact, the inventors have shown that DTT, but also Coenzyme A and N-Acetylcysteamine are all thiols able to replace efficiently DltC. In addition, contrary to the prior art, radioactivity is not used: all the assays are based either on luminescent ATP detection, or on fluorescent AMP detection. They are easily amenable to miniaturized formats and fast readouts as required by HTS.

DltA Luminescent Assay

The assay buffer "AB" contains 50 mM Hepes pH8.0, 10 mM MgCl$_2$, 50 mM KCl, 0.012% Triton-X100. The following components are added in a white polystyrene Costar plate up to a final volume of 30 μL: 3 μL DMSO, or inhibitor dissolved in DMSO and 27 μL DltA enzyme and DTT in AB. After 30 min of pre-incubation at room temperature, 30 μL of Substrates mix in AB are added in each well to a final volume of 60 μL. This reaction mixture is then composed of 10 nM DltA (produced in house from *S. agalactiae*), 0.5 mM D-Alanine (Sigma), 0.5 μM ATP (Sigma) and 1 mM DTT (Biochemika) in assay buffer. After 90 min of incubation at room temperature, 30 μL of the revelation mix are added to a final volume of 90 μL, including the following constituents at the respective final concentrations: 2 nM luciferase (Sigma), 30 μM D-luciferin (Sigma), 100 μM N-acetylcysteamine (Aldrich). Luminescence intensity is immediately measured on an Analyst-HT (Molecular Devices) and converted into inhibition percentages. For $IC_{50}$ (Inhibitory Concentration 50%) determinations, the inhibitor is added at 6 to 10 different concentrations, and the related inhibitions are fitted to a classical langmuir equilibrium model using XLFIT (IDBS).

DltA Fluorescent Assay

Figure 2:
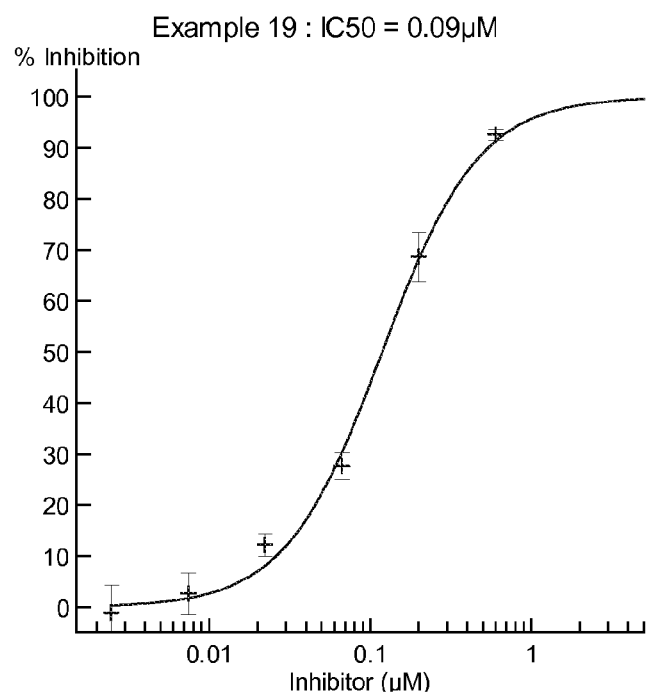
FIG. 2 shows an example of a dose-response curve of the quinoxaline derivative of example 19 on the DltA enzyme activity (fluorescent assay).

The assay buffer "AB" contains 50 mM Hepes pH8.0, 10 mM $MgCl_2$, 50 mM KCl, 0.012% Triton-X100. The following components are added in a black polystyrene Costar plate up to a final volume of 50 μL: 5 μL DMSO, or inhibitor dissolved in DMSO and 45 μL DltA enzyme and DTT in AB. After 30 min of pre-incubation at room temperature, 50 μL of Substrates-revelation mix in AB are added in each well to a final volume of 100 μL. This reaction mixture is then composed of 5 nM DltA (produced in house from *S. agalactiae*), 0.5 mM D-Alanine (Sigma), 10 μM ATP (Sigma), 1 mM DTT (Biochemika), 10 nM Adenylate kinase (produced in house), 5 u/mL Pyruvate Kinase (Sigma), 50 μM phosphoenolpyruvate (Sigma), 5 u/mL Lactate deshydrogenase (Sigma) and 3 μM NADH (Sigma) in assay buffer. Fluorescence intensity of NADH ($\lambda_{ex}$=360 nm, $\lambda_{em}$=520 nm) is immediately measured kinetically by a Fluostar Optima (BMG). Inhibition percentages are derived from fitted initial velocities. For $IC_{50}$ determinations, the inhibitor is added at 6 to 10 different concentrations, and the related inhibitions are fitted to a classical langmuir equilibrium model using XLFIT (IDBS). FIG. 2 represents the data obtained using this method.

The capacity of compounds to inhibit DltA enzymatic activity was assessed using the DltA HTS assays described in method 1.

In the following table 1 the results of DltA inhibition by the derivatives of examples 1-37 are presented to illustrate the invention. They are expressed as $IC_{50}$ (μM) values of the derivatives. The most potent molecules are the one with the lowest $IC_{50}$ (μM) values.

TABLE 1

| Molecules | | $IC_{50}$ (μM) |
| --- | --- | --- |
| Example 1 | [structure] | 3.2 |
| Example 2 | [structure] | 2.5 |
| Example 3 | [structure] | 0.62 |

TABLE 1-continued

| Molecules | IC$_{50}$ (μM) |
|---|---|
| Example 4 | 6.6 |
| Example 5 | 0.56 |
| Example 6 | 6.5 |
| Example 7 | 2.2 |
| Example 8 | 0.12 |

TABLE 1-continued
| Molecules | IC$_{50}$ (µM) |
|---|---|
| Example 9 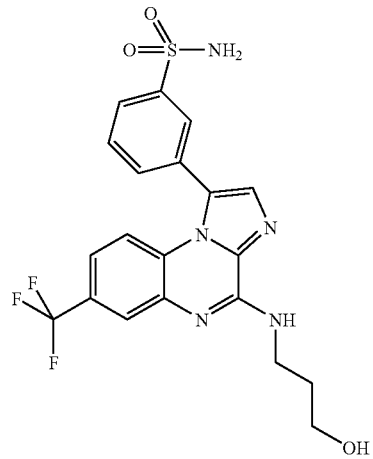 [SMILES: NS(=O)(=O)c1cccc(-c2cnc3c(NCCCO)nc4cc(C(F)(F)F)ccc4n23)c1] | 0.69 |
| Example 10 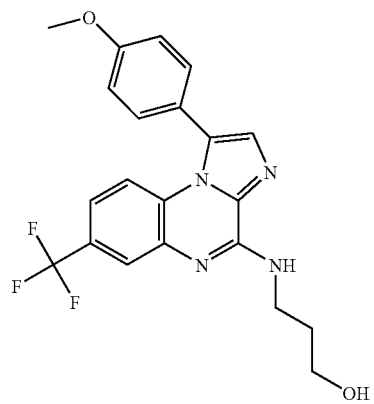 [SMILES: COc1ccc(-c2cnc3c(NCCCO)nc4cc(C(F)(F)F)ccc4n23)cc1] | 0.23 |
| Example 11 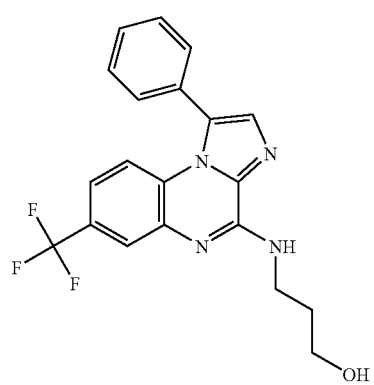 [SMILES: OCCCNc1nc2cc(C(F)(F)F)ccc2n2c(-c3ccccc3)cnc12] | 0.73 |

TABLE 1-continued
| Molecules | | IC$_{50}$ (μM) |
|---|---|---|
| Example 12 | 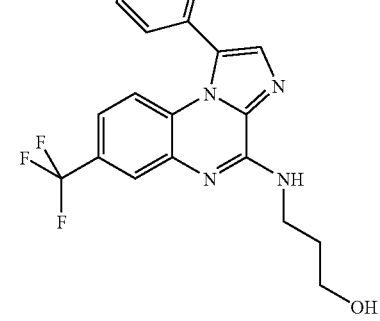 | 0.087 |
| Example 13 | 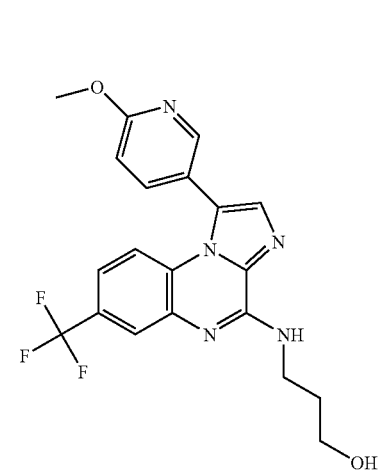 | 0.48 |
| Example 14 | 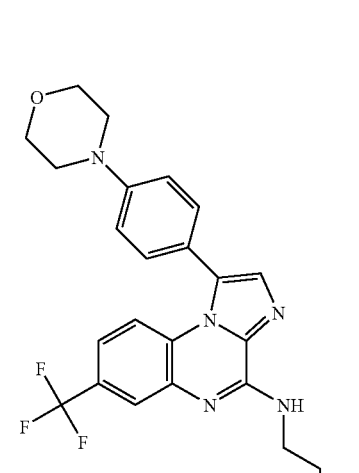 | 0.46 |

TABLE 1-continued

| Molecules | IC$_{50}$ (μM) |
|---|---|
| Example 15 | 0.2 |
| Example 16 | 0.52 |
| Example 17 | 0.51 |
| Example 18 | 0.24 |

TABLE 1-continued

| Molecules | IC$_{50}$ (µM) |
|---|---|
| Example 19 | 0.009 |
| Example 20 | 0.86 |
| Example 21 | 0.27 |
| Example 22 | 1 |

TABLE 1-continued
| Molecules | IC$_{50}$ (μM) |
|---|---|
| Example 23 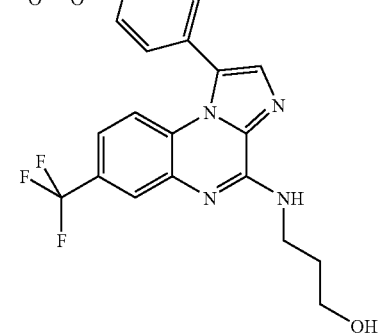 | 0.21 |
| Example 24 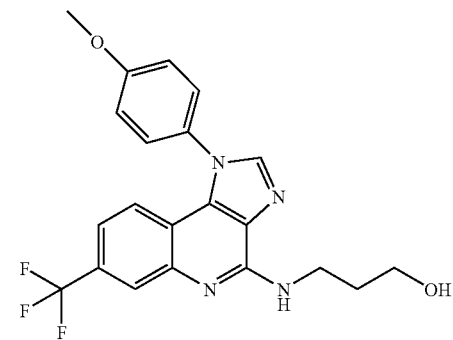 [SMILES: COc1ccc(-n2cnc3c(NCCCO)nc4cc(C(F)(F)F)ccc4c32)cc1] | 3.9 |
| Example 25 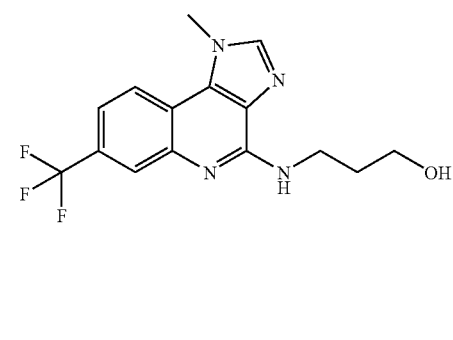 [SMILES: Cn1cnc2c(NCCCO)nc3cc(C(F)(F)F)ccc3c21] | 17 |
| Example 26 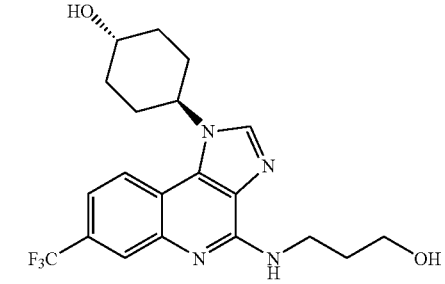 | 20 |

TABLE 1-continued
| Molecules | IC$_{50}$ (μM) |
|---|---|
| Example 27 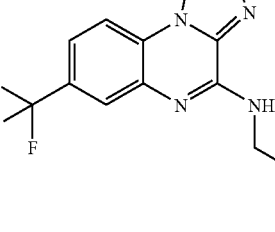 | 2.6 |
| Example 28 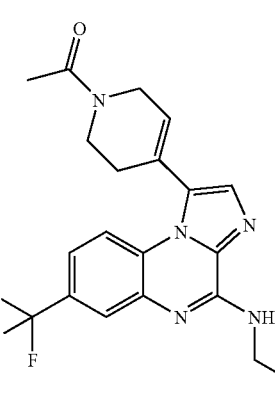 | 0.65 |
| Example 29 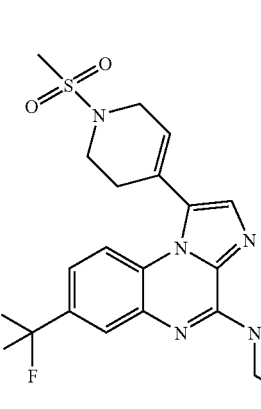 | 0.41 |
| Example 31 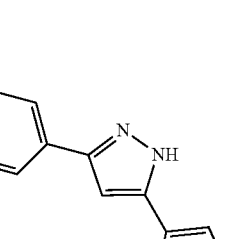 | 0.79 |

TABLE 1-continued
| Molecules | IC$_{50}$ (µM) |
|---|---|
| Example 32 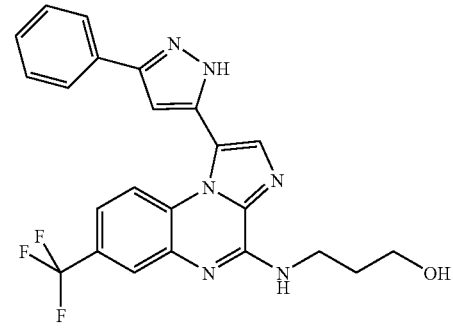 [SMILES: OCCCNc1nc2cc(C(F)(F)F)ccc2n2c(-c3cc(-c4ccccc4)n[nH]3)cnc12] | 0.042 |
| Example 33 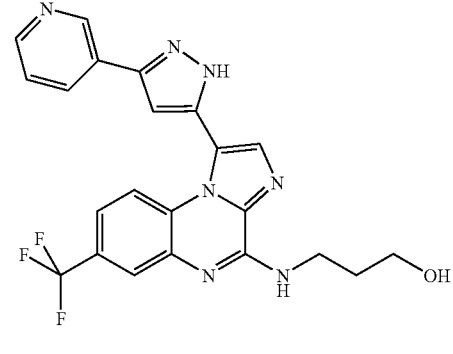 [SMILES: OCCCNc1nc2cc(C(F)(F)F)ccc2n2c(-c3cc(-c4cccnc4)n[nH]3)cnc12] | 0.025 |
| Example 34 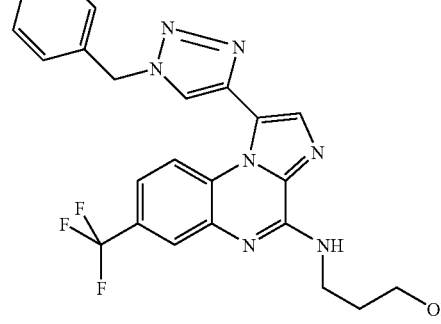 | 0.58 |
| Example 35 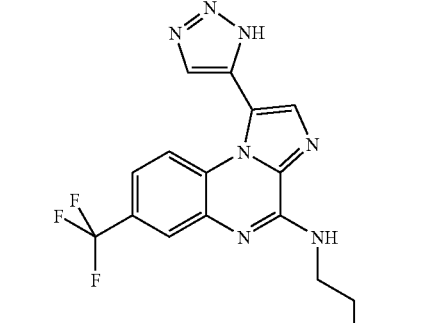 | 0.27 |

TABLE 1-continued

| Molecules | IC$_{50}$ (μM) |
|---|---|
| Example 36 | 0.049 |
| Example 37 | 0.16 |
| Example 38 | 0.0135 |
| Example 39 | 0.0135 |

TABLE 1-continued

| Molecules | IC$_{50}$ (μM) |
|---|---|
| Example 40 | 0.057 |
| Example 41 | 4.6 |
| Example 42 | 1.1 |
| Example 43 | 1.2 |

TABLE 1-continued
| Molecules | IC$_{50}$ (μM) |
|---|---|
| Example 44 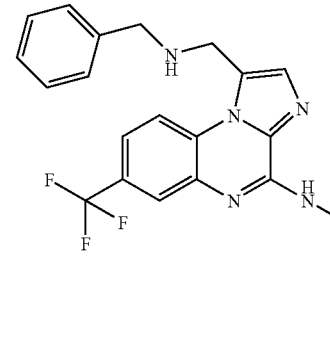 | 6.1 |
| Example 45 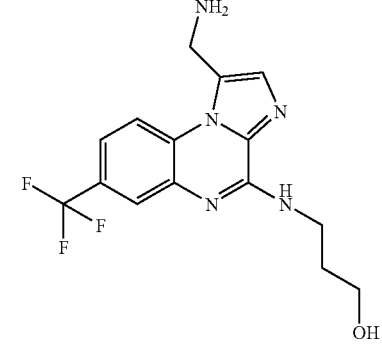 [SMILES: NCc1cnc2c(NCCCO)nc3cc(C(F)(F)F)ccc3n12] | 5.5 |
| Example 46 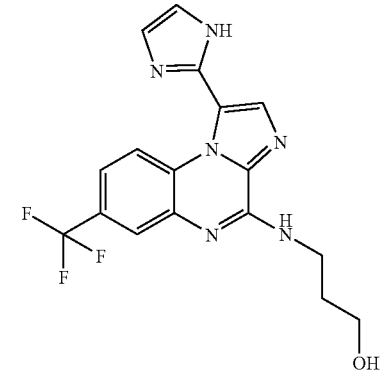 [SMILES: OCCCNc1nc2cc(C(F)(F)F)ccc2n2c(-c3ncc[nH]3)cnc12] | 3.5 |
| Example 47 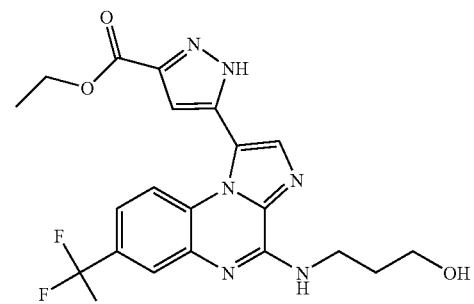 | 0.035 |

TABLE 1-continued
| Molecules | | IC$_{50}$ (μM) |
|---|---|---|
| Example 48 | 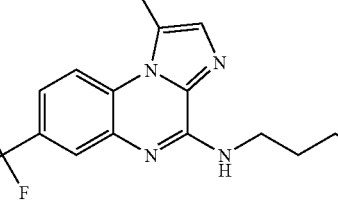 | 5 |
| Example 49 | 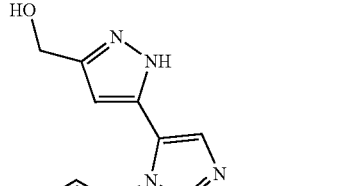 | 0.016 |
| Example 50 | 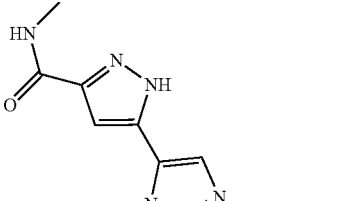 | 0.038 |
| Example 51 | 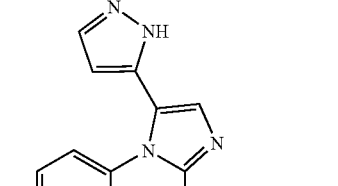 | 0.009 |
| Example 52 | 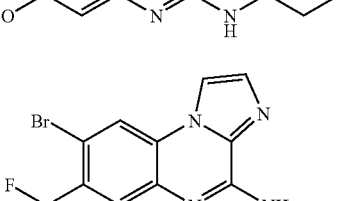 | 8.7 |

TABLE 1-continued
| Molecules | | IC$_{50}$ (μM) |
|---|---|---|
| Example 53 | 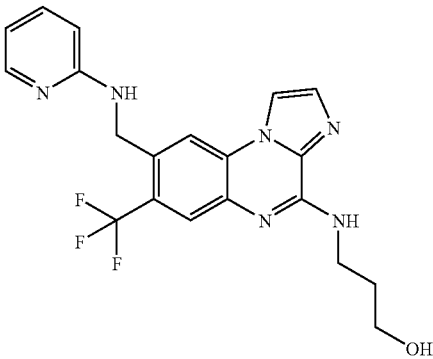 [SMILES: OCCCNc1nc2cc(C(F)(F)F)c(CNc3ccccn3)cc2n2ccnc12] | 0.51 |
| Example 54 | 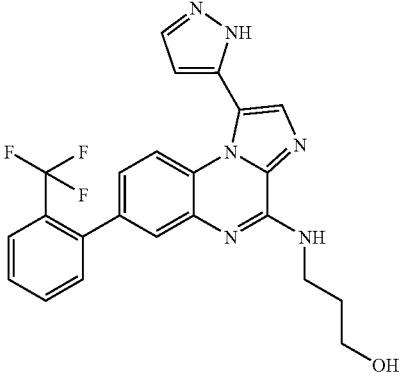 [SMILES: OCCCNc1nc2cc(-c3ccccc3C(F)(F)F)ccc2n2c(-c3ccn[nH]3)cnc12] | 0.022 |
| Example 55 | 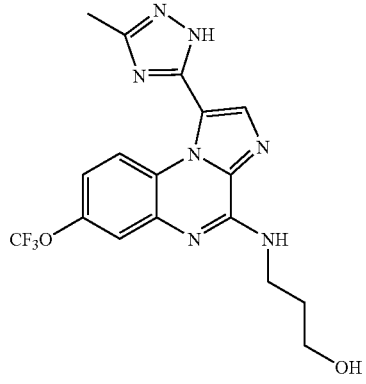 | 0.025 |
| Example 56 | 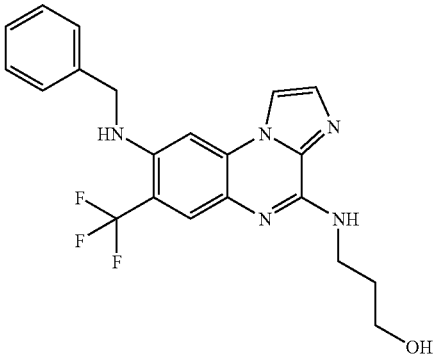 [SMILES: OCCCNc1nc2cc(C(F)(F)F)c(NCc3ccccc3)cc2n2ccnc12] | 0.81 |

TABLE 1-continued

| Molecules | | IC$_{50}$ (µM) |
|---|---|---|
| Example 57 | [Structure: 7,8-difluoro-imidazo[1,2-a]quinoxaline with NH-CH$_2$CH$_2$CH$_2$-OH substituent at position 4] | 57 |
| Example 58 | [Structure: 8-CF$_3$-imidazo[1,2-a]quinoxaline with 1H-pyrazol-3-yl substituent and NH-CH$_2$CH$_2$CH$_2$-O-P(=O)(ONa)(ONa) substituent at position 4] | 19 |

The effects of the Dlta Inhibitor molecules on bacterial multiplication were then assessed in an in vitro assay using the method 2 as described below.

Method to Measure the Efficacy of Molecules in Inhibiting Bacteria Proliferation In Vitro:

This method is based on the measurement of the bacterial phenotypic changes induce by DltA inhibition and in particular the bacterium sensitivity to the lytic effect of cationic peptides in presence of the compounds and is called sensitization of bacteria to cationic peptide.

The peptide used was colistin which mimicks the effect of antibacterial cationic peptide of innate immunity. In common with other polymixins, colistin is rapidly bactericidal and exerts its effect by acting as a cationic detergent, causing disruption of the integrity of the bacterial cell membrane, with leakage of intracellular contents and cell death. Colistin is not active on wild type strain Gram-positive bacteria at concentration up to 1024 µg/ml (on S. agalactiae strain NEM316 and on S. aureus strain 54.316, colistin has a MIC≧1024 µg/ml). By contrast, the inventors have determined that a dose of 32 µg/ml of colistin can inhibit totally the growth of a dltA defective mutant of S. agalactiae without effect on the wild type strain growth.

The method was standardized as an in vitro assay, necessary to determine the activity of the enzyme inhibitors in the bacterial cell, as a surrogate of activity in vivo.

DltA inhibitor molecules when in presence of the bacterial cell are able to inhibit the d-alanylation of LTA and render the bacteria sensitive to an antibacterial peptide or a peptide mimicking its effect, resulting in the inhibition of bacterial growth. In the mean time DltA inhibitor molecules do not inhibit the growth in the absence of said peptide.

The readout of the assay is called Minimum antivirulent concentration (MAC) and represents the minimal dose of compound for which no visible bacterial growth is observed in the presence of colistin at a subinhibitory concentration. MAC assay is described in Method 3 hereinafter.

Furthermore to verify that molecules do not have a direct lethal effect on the bacterial cell, they were assessed in a standard antibacterial assay by measuring their Minimum Inhibitory Concentration (MIC).

Alternatively, one can determine the Antivirulence Effective Concentration 50% (AEC$_{50}$) instead of the MAC, as described in method 2.

Method 2: Assay for Antivirulence Effective Concentration 50% (AEC$_{50}$): Determination of Compounds Activity for Sensitization of Bacteria to Cationic Peptide (Colistin)

The Gram positive bacteria, S. agalactiae NEM316 WT and S. aureus CIP 54.146 are grown on tryptic soy agar (TSA) broth over-night at 37° C. with air enriched with 5% CO$_2$.

Ten to fifteen colonies isolated from over-night growth on agar are then added to 10 ml of TS media to produce a standard suspension of organisms. This pre-culture is incubated at 37° C. with constant shaking during two to three hours to reach the exponential phase. This suspension is diluted to obtain an inoculum of 1 E+05 UFC/ml. Viable counts are obtained by plating 10 to 1000-fold dilutions of the suspension on TSA.

According to our standardized conditions, the final volume in the well is 100 µl in a 96-well microplate. Compounds are tested in a range of 3.125 to 50 µM. Each well contains 25 µl of compound diluted in TS, 25 µl of TS (microplate without colistin) or 25 µl of colistin then 50 µl of bacterial suspension. Final concentration of colistin is 32 µg/ml for S. agalactiae and 256 µg/ml for S. aureus. Final concentration of DMSO is 1%.

The microplates are then incubated during 5 hours for S. agalactiae and 5.5 hours for S. aureus at 37° C. with 5% CO$_2$.

After shaking the microplates 5 minutes, $OD_{600}$ of microplates is read on Multiskan EX apparatus (Thermo).

Positive growth control wells for each organism are prepared with and without colistin and DMSO 1% final concentration. S. agalactiae NEM316 Δdlt is used in control wells to verify the effect of the colistin on a sensitive strain.

The % of growth inhibition is calculated, in both conditions: with and without colistin, for each concentration of compound by comparing the OD of the well containing the compound to the positive growth control well.

Figure 3:
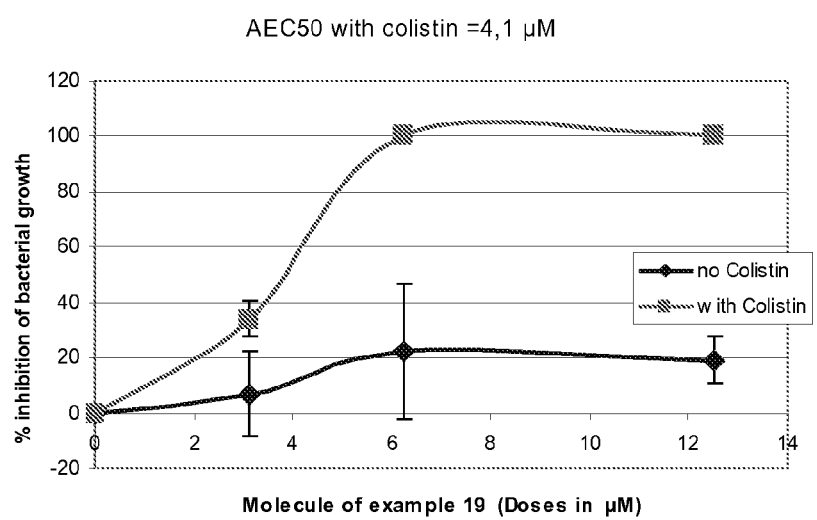
FIG. 3 shows the effect of the quinoxaline derivative of example 19 on the inhibition of bacterial growth. The dose response curve with squares shows the inhibition percentage of S. agalactiae bacterial growth as function of concentration of the quinoxaline derivative of example 19 and in presence of colistin. The dose response curve with diamonds shows the inhibition percentage of S. agalactiae bacterial growth as function of concentration of the quinoxaline derivative of example 19 and in absence of colistin.

The Antivirulence Effective Concentration 50% ($AEC_{50}$), determined by the software XL-Fit, is the interpolated concentration of compound for 50% of growth inhibition. FIG. 3 illustrate the data obtained using this assay with an inhibitor molecule, i.e. the effect of DltA inhibitor on S. agalactiae NEM316 wt bacterial multiplication in vitro after 5 h in presence or absence of 32 μg/mL colistin Antivirulence molecules are capable of inhibiting bacterial growth in presence of an antibacterial peptide or a peptide mimicking its effect ($AEC_{50}$<50 μM) and do not inhibit the growth in the absence of said peptide ($AEC_{50}$>50 μM). This was also demonstrated in standard MIC assay well known from the one skilled in the art.

Method 3: Assay for Minimal Antivirulent Concentration (MAC) and Minimal Inhibitory Concentration (MIC): Determination of Compounds Activity for Sensitization of Bacteria to Cationic Peptide (Colistin)

The Gram positive bacteria S. agalactiae NEM316 WT are grown on tryptic soy agar (TSA) broth over-night at 37° C. with air enriched with 5% $CO_2$. Ten to fifteen colonies isolated from over-night growth on agar are then added to 10 ml of TS media to produce a standard suspension of organisms. This pre-culture is incubated at 37° C. with constant shaking during two to three hours to reach the exponential phase. This suspension is diluted to obtain a final inoculum of 1E+04 CFU/ml. Viable counts are obtained by plating 10 to 1000-fold dilutions of the suspension on TSA.

According to our standardized conditions, the final volume in the well is 100 μl in a 96-well microplate. Compounds are tested in a range of 1 to 32 μg/mL. Each well contains 2 μl of compound diluted in 100% DMSO, 48 μl of TS (microplate without colistin) or 48 μl of colistin in TS (final concentration of colistin is 32 μg/ml for S. agalactiae), then 48 μl of bacterial suspension (final inoculum of 1 E+04 CFU/ml). Final concentration of DMSO is 2%. Positive growth control wells for each organism are prepared with and without colistin and DMSO 2% final concentration. S. agalactiae NEM316 Δdlt is used in control wells to verify the effect of the colistin on a sensitive strain.

The microplates are then incubated overnight at 37° C. with 5% $CO_2$. Visible bacterial growth is finally quantified by unaided eye.

The MIC of each compound is derived from the experiment in absence of colistin and is defined as the minimal concentration of compound for which no bacterial visible growth is observed.

The MAC of each compound is derived from the experiment in presence of colistin and is defined as the minimal concentration of compound for which no bacterial visible growth is observed.

Antivirulent molecules are characterized by the capacity to inhibit bacterial growth in presence of an antibacterial peptide or a peptide mimicking its effect (MAC<32 μg/mL) and without the capacity to inhibit the growth in the absence of said peptide (MIC>32 μg/mL).

In the following Table 2 a summary of each compounds activities in vitro is given to illustrate the invention. In the table 2 are presented in the first column the result of the inhibition of DltA enzymatic activity in vitro measured by the $IC_{50}$ (μM) in the HTS assay, then in the second column the value of MAC (μg/mL) representing the inhibition of bacterial growth (S. agalactiae wt strain) in presence of colistin. Finally in the right column are the value of the MIC determination on S. agalactiae wt strain (SAG wt)., to measure a potential direct antibacterial activity of the molecules.

These data indicate that DltA enzyme inhibitors present various degree of activity on the bacterial cells as measured by MAC determination and that none of the examples tested have a direct antibacterial effect as reflected by the high MIC values.

TABLE 2

| Molecules | IC50 (μM) | MAC (μg/ml) | MIC SAG wt (μg/ml) |
|---|---|---|---|
| Example 16 | 0.52 | 8 | >32 |
| Example 19 | 0.009 | 2 | >32 |
| Example 35 | 0.27 | 2 | >32 |
| Example 36 | 0.049 | 4 | >32 |
| Example 39 | 0.0135 | 8 | >32 |
| Example 47 | 0.035 | 8 | >32 |
| Example 50 | 0.038 | 8 | >32 |
| Example 51 | 0.009 | 2 | >32 |

PART C

Assessing the Antibacterial Activity of Compounds in the Host.

The inventors demonstrated that the inhibitors of DltA could be useful in rendering invading bacteria sensitive to killing by the innate immunity mechanism of the host, making the bacteria avirulent and allowing the eradication or prevention of the infection and that the molecules could be useful as antibacterial compounds with a new mechanism of action when compared to current antibiotic treatment.

The effect of DltA inhibitors on the bacteria during an infection was assessed by injecting the molecules at different doses in group of mice that have received an infective dose of bacteria.

Description of Experimental Models Used to Assess the Efficacy of Inhibitors In Vivo:

Briefly, in vivo studies were performed using 4-5-week-old female BALB/c@Rj nice. S. agalactiae strain NEM316 bacteria were grown to exponential phase in broth culture. 200 μl of a bacterial suspension of $3.10^7$ CFU/ml were administered by intravenous injection to groups of six mice ($6.10^6$ CFU/mouse). Exact inoculums counts were determined by plating 10-fold dilutions of the suspension on TH agar plates immediately after inoculation.

The compounds to be assessed are dissolved and diluted to obtain different concentration in a solution containing solutol; and 400 μl of each compound solution is injected intraperinonaly immediately after infection of the mouse.

At 48 hours post-infection, mice were sacrificed and the abdominal cavities of the mice were aseptically opened, and the livers and spleen were removed. Organs were homogenized with a tissue homogenizer (Heidolph) in 1 ml of sterile

```
                         SEQUENCE LISTING

<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Primers

<400> SEQUENCE: 1
caccatgata catgatatga ttaaaacaat tgagcatttt gc                         42

<210> SEQ ID NO 2
<211> LENGTH: 27
<212> TYPE: DNA
<213> ORGANISM: Artificial sequence
<220> FEATURE:
<223> OTHER INFORMATION: Primers

<400> SEQUENCE: 2
tcacttgttt acctcgctca taagacc                                          27
```

For *S. aureus*, the infection was carried out in a similar manner except that bacteria were injected i.p at the dose of 5.106 UFC/ml in a volume of 200 μl. At 48 h post infection, organs were removed and bacteraemia determined by the number of UFC/mg recovered.

The antibacterial effect obtained with different concentrations of compounds is measured by the level of bacteraemia observed at 48 H.

All animal experiments were carried out in accordance with institutional guidelines. Examples of the results obtained with derivatives of formula (I) in an in vivo assay with the experimental model of systemic infection by *S. agalactiae* NEM316 are presented on FIGS. 1 A to D.

The graphs represent the average value of the organ bacteremia that is determined by the number of UFC/mg of organs (spleen) at 48 h post infection, obtained for each group of mice that have received different concentration of compounds (expressed in mg/kg).

Results are presented as the mean value of two independents experiments.

In FIG. 1C the results represent the effect of different concentration of the molecule of example 16 and the effect obtained with the treatment by telithromycin at 10 mg/kg that was used as an antibacterial reference compound in that experiment.

These results demonstrate for the first time that the DltA inhibitors are indeed able to affect the bacterial multiplication in the host as shown by the diminution (by one to two log 10) of the value of the bacteremia observed with the presence of the compounds when compared to the bacteremia observed without the presence of the compounds (the 0 mg/mkg dose). The in vivo antibacterial effect of the compounds increases with the doses. The effective concentration of compound of example 19 is 10 mg/kg dose and it illustrates the potency of such molecules as antibacterial.

These results demonstrate that in vivo the effect of compounds able to inhibit DltA function can induce a decrease in bacterial multiplication and demonstrate an antibacterial effect at doses comparable to the effective doses of classical antibiotics.

The invention claimed is:

1. An imidazolo-heteroaryl derivative of formula (I)

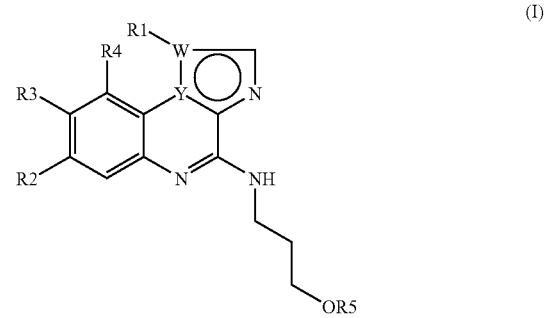

(I)

wherein,

Y=N and W is C or

Y=C and W=N,

R1 is $C_1$-$C_{10}$alkyl, $C_2$-$C_{10}$alkenyl, $C_2$-$C_{10}$alkynyl, $CO_2R_a$, $COR_a$, $CONR_aR_b$; $CR_a$=$NOR_b$, $S(O)_nR_a$, phenyl or heterocycle, all being optionally substituted by one or several identical or different R, or R1 is H, halogen or CN;

$R_2$ is $C_1$-$C_{10}$alkyl, $C_2$-$C_{10}$alkenyl, $C_2$-$C_{10}$alkynyl $OR_a$, $S(O)_nR_a$, phenyl or heterocycle, all being optionally substituted by one or several identical or different R, or R2 is H or halogen;

$R_3$ is $C_1$-$C_{10}$alkyl, $C_2$-$C_{10}$alkenyl, $C_2$-$C_{10}$alkynyl, $CO_2R_a$, $COR_a$, $CR_a$, $NR_aR_b$, $NR_aCOR_b$, $CONR_aR_b$, $CR_a$=$NOR_b$, $S(O)_nR_a$, $SO_2NR_aR_b$, phenyl or heterocycle, all being optionally substituted by one or several identical or different R, or R3 is H, halogen or CN;

R4 is $C_1$-$C_{10}$alkyl, $C_2$-$C_{10}$alkenyl, $C_2$-$C_{10}$alkynyl, phenyl or heterocycle all being optionally substituted by one or several identical or different R, or R4 is H, halogen or CN;

R5 is H, $COR_a$, $CO_2R_a$, $P(O)(OH)_2$ or $COCHR_aNR_bR_c$;

$R_a$, $R_b$ and $R_c$ identical or different are selected from the group consisting of H, $C_1$-$C_{10}$alkyl, $C_2$-$C_{10}$alkenyl, $C_2$-$C_{10}$alkynyl, phenyl and heterocycle;

R is selected from the group consisting of $C_1$-$C_{10}$alkyl, $C_2$-$C_{10}$alkenyl, $C_2$-$C_{10}$alkynyl, phenyl, heterocycle, $CO_2R_a$, $COR_a$, $CONR_aR_b$, $OCOR_a$, $OR_a$, $NR_aR_b$, $CR_a$=$NOR_b$, $NR_aCORb$, $NR_aCOOR_b$, $OCONR_aR_b$, $NR_aCONR_bR_c$, $NR_aSO_2R_b$, $S(O)_nR_a$, and $SO_2NR_aR_b$, all being optionally substituted by one or several identical or different R', or R is halogen; CN or $NO_2$, Ra, Rb and Rc are such as described above;

R' is selected from the group consisting of $C_1$-$C_{10}$alkyl, $CO_2R''$, $COR''$, $CONR''R'''$, $OCOR''$, $OR''$, $NR''R''OR''$=$NOR''NR''COR'''$, $NR''COOR'''$, $OCONR''R'''$, $NR''C0NR''R''NR''SO_2R''S(O)_nR''$, $SO_2NR''R''$ halogen, CN and $NO_2$;

R'' and R''' being identical or different are H or $C_1$-$C_{10}$alkyl or form together a 3 to 6 membered nitrogenous heterocycle;

n is 0, 1 or 2;

with the proviso that R5 is not H, when R2=F or $SO_2CH_3$; R1, R3 and R4=H; and W=C, and with the proviso that R1, R2, R3, R4 and R5 are not all H when W is C and Y is N, or a pharmaceutically acceptable salt thereof.

2. The derivative of claim 1, wherein Y=N and W is C and R1 is selected from the group consisting of H, halogen, $C_1$-$C_{10}$alkyl, $C_2$-$C_{10}$alkenyl, $C_2$-$C_{10}$alkynyl, $CO_2R_a$, $COR_a$, $CONR_aR_bS(O)_nR_a$ phenyl, R substituted phenyl, 5 or 6-membered heterocycle, and R substituted heterocycle.

3. The derivative of claim 1, wherein Y=C and W is N and R1 is selected from the group consisting of H, $C_1$-$C_{10}$alkyl, R substituted alkyl, phenyl and R substituted phenyl.

4. The derivative of claim 2, wherein R1 is H.

5. The derivative of claim 2, wherein R1 is $C_1$-$C_{10}$alkyl.

6. The derivative of claim 2, wherein R1 is $C_2$-$C_{10}$alkenyl.

7. The derivative of claim 2, wherein R1 is $C_2$-$C_{10}$alkynyl.

8. The derivative of claim 2, wherein R1 is an halogen selected between Br and I.

9. The derivative of claim 2, wherein R1 is phenyl.

10. The derivative of claim 2, wherein R1 represents a phenyl group substituted by R which is selected from the group consisting of $C_1$-$C_{10}$alkyl-CO—NH—, $NH_2$—$SO_2$—, $C_1C_{10}$alkyl-O—$C_1$-$C_{10}$alkyl-$SO_2$—NH, non aromatic heterocycle, $C_1$-$C_{10}$alkyl-NH—CO—, HO—$C_1C_{10}$-alkyl-, and $NH_2$—$C_{10}$alkyl-, or R1 is a phenyl group substituted by two R.

11. The derivative of claim 2, wherein R1 is an heterocycle selected from the group consisting of pyrazolyl, triazolyl, pyridyl, and pyrimidinyl.

12. The derivative of claim 2, wherein R1 is an aromatic or non aromatic heterocycle substituted by R which is selected from the group consisting of $C_1$-$C_{10}$alkyl-O—, $NH_2$, $C_1$-$C_{10}$alkyl-CO—, $C_1$-$C_{10}$alkyl-$SO_2$—, $C_1$-$C_{10}$alkyl-O—$C_6H_4$—, phenyl, pyridyl, $C_6H_4$—$CH_2$— and $R_aOOC$—.

13. The derivative of claim 2, wherein R1 is CHO.

14. The derivative of claim 2, wherein R1 is $COOR_a$—.

15. The derivative of claim 2, wherein R1 is $COOR_aR_b$—.

16. The derivative of claim 2, wherein R1 is $S(O)_nR_a$—.

17. The derivative of claim 3, wherein R1 is H, or $C_1$-$C_{10}$ alkyl substituted by R.

18. The derivative of claim 3, wherein R1 represents a phenyl group substituted or not by R.

19. The derivative according to claim 2, wherein R3 is H, $NR_aR_b$, halogen, or $C_1$-$C_{10}$alkyl.

20. The derivative according to claim 2, wherein R4 is H or a phenyl substituted by R.

21. The derivative according to claim 2, wherein R2 is $CF_3$—, $CF_3O$—$CF_3$—$C_6H_4$—, $CH_3S$—, $CH_3$—$CH_2$—S—, Br or H.

22. The derivative according to claim 2, wherein R5 is H.

23. The derivative according to claim 2, wherein R5 is $COR_a$, $CO_2Ra$, $P(O)(OH)_2$ or $COCHR_aNR_bR_c$.

24. The derivative of claim 1, wherein

R1=H, Br, $CH_2$=CH—, phenyl, phenyl substituted by $CH_3$—CO—NH—, $NH_2$—SO, $CH_3O$—, $CH_3$—$SO_2$—NH—, morpholino, $CH_3$—NH—CO—, $HOCH_2$—, $NH_2$—$CH_2$—, both $NH_2$— and $CH_3$—O—, or R1 is pyrazolyl, pyrazolyl substituted by $CH_3$—O—$C_6H_4$—, pyridyl substituted by $CH_3$—O—, triazolyl, triazolyl substituted by $C_6H_4$—$CH_2$—, pyrimidinyl substituted by $NH_2$ or piperazinyl substituted by $CH_3SO_2$—, or $CH_3CO$;

R2=$CF_3$, $CF_3$—$C_6H_4$—, $CF_3$—O—;

R3=R4=R5=H;

Y=N and W=C;

said derivative having an $IC_{50}$ lower than or equal to 2.5 μM.

25. The derivative of claim 1, further characterized by the following properties: it is able to inhibit the activity of de DltA enzyme, it is able to render resistant bacteria sensitive to antibacterial cationic peptides and peptides mimicking said cationic peptides in vitro, and it is active in preventing bacterial multiplication in an experimental model of infection in mice model by rendering the bacteria avirulent.

26. A composition comprising at least a derivative of formula (I) as defined in claim 1, for use as drug.

27. The composition of claim 26 for use as antibacterial agent to treat Gram-positive bacterial infections in human and animals due to bacteria of a genus selected from the group consisting of *Staphylococcus, Bacillus, Listeria, Enterococcus, Streptococcus, Mycobacterium, Bacteroides* and *Clostridium*.

28. A pharmaceutical composition comprising an effective amount of at least one derivative of formula (I) as defined in claim 1, in combination with a pharmaceutically acceptable carrier.

29. A pharmaceutical composition comprising an effective amount of at least one derivative of formula (I) as defined in claim 1, in combination with an antibacterial molecule and a pharmaceutically acceptable carrier.

30. The pharmaceutical composition according to claim 28, which is formulated to be administered under oral, injectable, or parenteral routes, with individual doses appropriate for the patient to be treated.

31. The composition of claim 27 for use as antibacterial agent to treat Gram-positive bacterial infections in human and animals due to bacteria selected from the group consisting of *Staphylococcus aureus, Enterococcus faecalis, Enterococcus faecium, Mycobacterium tuberculosis, Streptococcus pyogenes, Streptococcus pneumoniae, Streptococcus agalactiae, Bacteroides fragilis*, and *Clostridium difficile*.

* * * * *

UNITED STATES PATENT AND TRADEMARK OFFICE
CERTIFICATE OF CORRECTION

PATENT NO.        : 8,513,250 B2                                                    Page 1 of 1
APPLICATION NO. : 12/450348
DATED             : August 20, 2013
INVENTOR(S)       : Escaich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Fifteenth Day of September, 2015

Michelle K. Lee
*Director of the United States Patent and Trademark Office*